United States Patent
Ichimura et al.

(10) Patent No.: US 6,790,974 B2
(45) Date of Patent: Sep. 14, 2004

(54) BIS(AMINOSTYRYL) NAPHTHALENE COMPOUND, SYNTHESIS INTERMEDIATE THEREOF, AND PROCESS FOR PRODUCTION THEREOF

(75) Inventors: Mari Ichimura, Kanagawa (JP); Tadashi Ishibashi, Kanagawa (JP); Shinichiro Tamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 10/389,787

(22) Filed: Mar. 17, 2003

(65) Prior Publication Data

US 2003/0204115 A1 Oct. 30, 2003

Related U.S. Application Data

(62) Division of application No. 10/231,419, filed on Aug. 29, 2002, which is a division of application No. 09/680,386, filed on Oct. 5, 2000, now Pat. No. 6,492,557.

(30) Foreign Application Priority Data

Oct. 6, 1999 (JP) .......................................... P11-285255

(51) Int. Cl.[7] ................................................. C07C 9/40
(52) U.S. Cl. ...................................... 558/156; 558/158
(58) Field of Search ............................ 558/70, 87, 156, 558/155, 158; 568/9

(56) References Cited

U.S. PATENT DOCUMENTS 3,627,758 A * 12/1971 Weber et al. .................. 544/79
5,130,603 A * 7/1992 Tokailin et al. ............. 313/504

FOREIGN PATENT DOCUMENTS

CH 555 424 * 1/1975

OTHER PUBLICATIONS

CA:100:138490 abs of Bulletin des Societes Belges by Brison et al 92(10) pp 901–12 1983.*

* cited by examiner

*Primary Examiner*—Jean F. Vollano
(74) *Attorney, Agent, or Firm*—Sonnenschein, Nath & Rosenthal LLP

(57) ABSTRACT

A bis(aminostyryl)naphthalene compound represented by the general formula [I] or the like below.

General Formula [I]

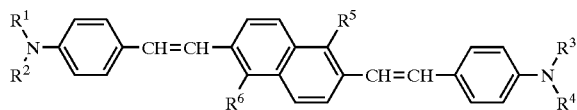

(where $R^2$ and $R^3$ each denotes an unsubstituted aryl group; $R^1$ and $R^4$ each denotes an aryl group having a specific substituent such as methoxy group; and $R^5$ and $R^6$ each denotes a cyano group or the like.)

A process for producing a bis(aminostyryl)naphthalene compound represented by the general formula [I] by condensation of, for example, 4-(N,N-diarylamino)benzaldehyde with diphosphonic ester or diphosphonium.

The bis(aminostyryl)naphthalene compound emits intense yellow or red light. The process permits efficient production of the bis(aminostyryl)naphthalene compound.

4 Claims, 8 Drawing Sheets

BIS(AMINOSTYRYL) NAPHTHALENE COMPOUND, SYNTHESIS INTERMEDIATE THEREOF, AND PROCESS FOR PRODUCTION THEREOF

RELATED APPLICATION DATA

The present application claims priority to Japanese Application No. P11-285255, filed Oct. 6, 1999, and is a divisional of U.S. application Ser. No. 10/231,419, filed Aug. 29, 2002, which is a divisional of U.S. application Ser. No. 09/680,386 filed Oct. 5, 2000, now U.S. Pat. No. 6,492,557, all three of which are incorporated herein by reference to the extent permitted by law.

BACKGROUND OF THE INVENTION

The present invention relates to a bis(aminostyryl) naphthalene compound, a synthesis intermediate thereof, and a process for production thereof, the naphthalene compound being suitable for use as an organic luminescent material which emits light of desired color.

Organic electroluminescent elements (EL elements) nowadays are attracting attention as a component suitable for flat panel displays emitting light spontaneously, responding at high seeds, and being independent of viewing angles. This has aroused attention to organic luminescent materials as a constituent of EL elements. One advantage of organic luminescent materials is that they have desired optical properties according to their molecular design. Therefore, it is possible to produce luminescent materials emitting any of three primary colors (red, blue, and green). Combination of these luminescent materials will realize full-color organic electroluminescent elements.

A bis(aminostyryl)benzene compound represented by the general formula [A] below emits intense light of color from blue to red in the visible region depending on substituents introduced therein. Therefore, it will find use in various applications, not limited to use as a material for organic electroluminescent elements. It is capable of sublimation and hence it offers the advantage of forming a uniform amorphous film by vacuum deposition. At present, it is possible to predict to some extent the optical properties of a material by means of molecular orbital calculations. However, it is most important to develop a process for efficient production of a material necessary for practical use.

General Formula [A]

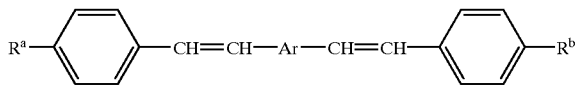

(where Ar denotes an aryl group which may has a substituents, and $R^a$ and $R^b$ may be identical or different, each denoting a hydrogen atom, saturated or unsaturated hydrocarbon group, aryl group which may have a substituent, cyano group, halogen atom, nitro group, trifluoromethyl group, amino group, or alkoxyl group.)

A large number of compounds represented by the general formula [A] have been produced so far as the organic luminescent material. Most of them emit light of blue to green, and a few of them emitting yellow to red light have been reported. [Institute of Electric Information and Communication, Report on Technical Researches, Organic Electronics, 17, 7 (1992); Inorganic and Organic Electroluminescence 96 Berlin, 101 (1996); etc.] Any process for their efficient production has never been established.

SUMMARY OF THE INVENTION

The present invention was completed in view of the foregoing. It is an object of the present invention to provide a compound which is suitable as an organic luminescent material to emit intense light of yellow to red colors, a synthesis intermediate thereof, and a process for efficient production thereof.

DETAILED DESCRIPTION OF THE PREFERRED EMBODIMENTS

Figure 1:
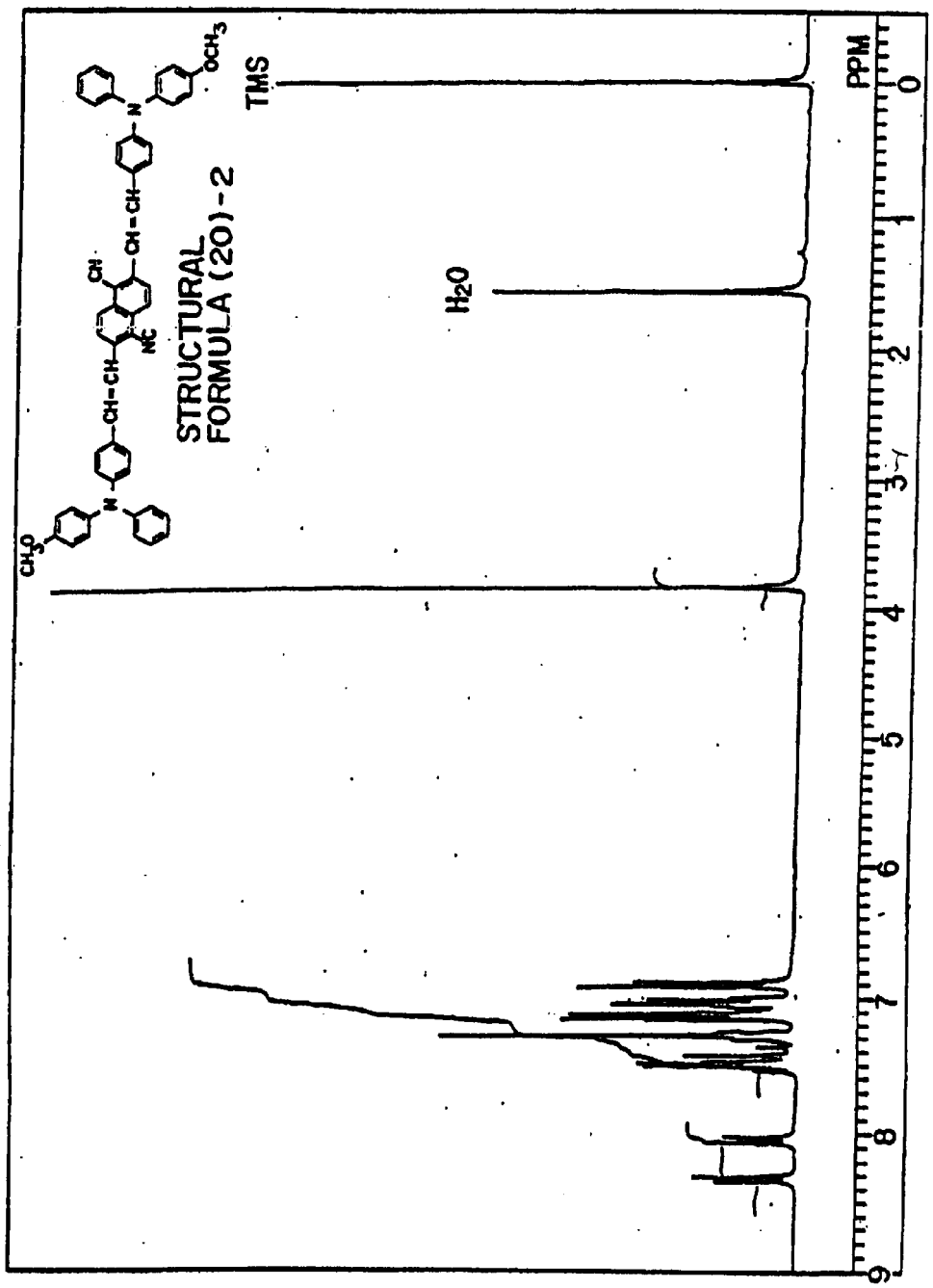
FIG. 1 is a $^1$HNMR spectral atlas of bis(aminostyryl) naphthalene compound (represented by the structural formula (20)-2) according to the present invention.

The present inventors carried out extensive studies to solve the above-mentioned problems. As the result, it was found that a bis(aminostyryl)naphthalene compound represented by the general formula [I], [II], [III], or [IV] below emits intense light and hence can be used as a luminescent material for yellow to red colors. In addition, the present inventors established a process for its efficient production. These findings led to the present invention.

First, the present invention is directed to a bis-(aminostyryl)naphthalene compound represented by the general formula [I], [II], [III], or [IV] below. This compound will be referred to as "the compound of the present invention" hereinafter.

General Formula [I]

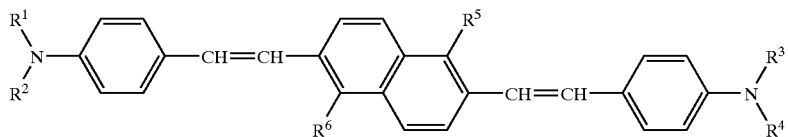

(where $R^2$ and $R^3$ each denotes an unsubstituted aryl group, and $R^1$ and $R^4$ each denotes an aryl group represented by the general formula (1) below.)

General Formula (1)

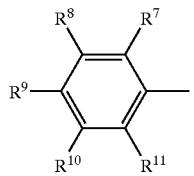

(where $R^7$, $R^8$, $R^9$, $R^{10}$ and $R^{11}$ are identical or different groups, at least one of them being a saturated or unsaturated hydrocarbon oxy group, hydrocarbon group, or hydrocarbon amino group having at least one carbon; and $R^5$ and $R^6$ are identical or different groups, at least one of them being a hydrogen atom, cyano group, nitro group, trifluoromethyl group, or halogen atom (such as F, Cl, Br, and I.) [The same shall apply hereinafter.]

General Formula [II]

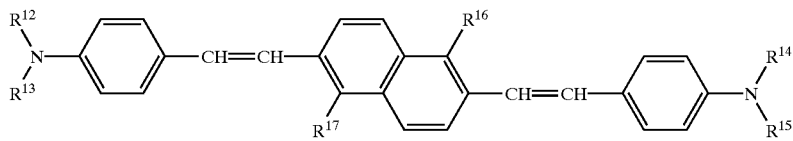

(where $R^{12}$, $R^{13}$, $R^{14}$, and $R^{15}$ are identical or different groups, each denoting an aryl group represented by the general formula (2) below.)

General Formula (2)

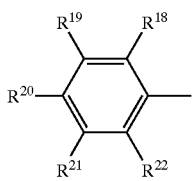

(where $R^{18}$, $R^{19}$, $R^{20}$, $R^{21}$, and $R^{22}$ are identical or different groups, at least one of them being a saturated or unsaturated hydrocarbon oxy group, hydrocarbon group, or hydrocarbon amino group having at least one carbon; and $R^{16}$ and $R^{17}$ are identical or different groups, at least one of them being a hydrogen atom, cyano group, nitro group, trifluoromethyl group, or halogen atom.)

General Formula [III]

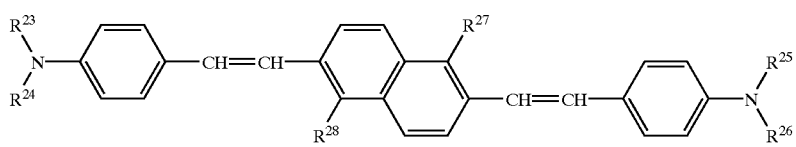

(where at least one of $R^{23}$, $R^{24}$, $R^{25}$, and $R^{26}$ denotes an aryl group represented by the general formula (3) below, with the remainder being an unsubstituted aryl group.)

General Formula (3)

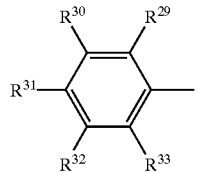

(where $R^{29}$, $R^{30}$, $R^{31}$, $R^{32}$, and $R^{33}$ are identical or different groups, at least one of them being a saturated or unsaturated hydrocarbon oxy group, hydrocarbon group, or hydrocarbon amino group; and $R^{27}$ and $R^{28}$ are identical or different groups, at least one of them being a hydrogen atom, cyano group, nitro group, trifluoromethyl group, or halogen atom.)

General Formula [IV]

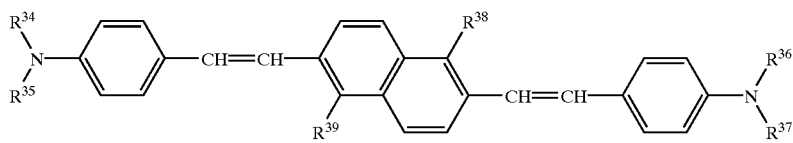

(where $R^{35}$ and $R^{36}$ are identical or different groups, each denoting an aryl group represented by the general formula (4) below.)

General Formula (4)

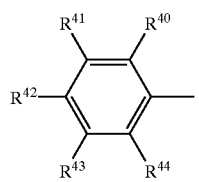

(where $R^{40}$, $R^{41}$, $R^{42}$, $R^{43}$, and $R^{44}$ are identical or different groups, each denoting hydrogen or at least one of them being a saturated or unsaturated hydrocarbon oxy group, hydrocarbon group, or hydrocarbon amino group having at least one carbon; and $R^{34}$ and $R^{37}$ are identical or different groups, at least one of them being an aryl group represented by the general formula (5) below.)

General Formula (5)

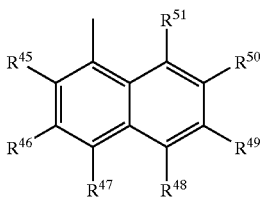

(where $R^{45}$, $R^{46}$, $R^{47}$, $R^{48}$, $R^{49}$, $R^{50}$, and $R^{51}$ are identical or different groups, each denoting a hydrogen atom or at least one of them being a saturated or unsaturated hydrocarbon oxy group, hydrocarbon group, or hydrocarbon amino group having at least one carbon; and $R^{38}$ and $R^{39}$ are identical or different groups, at least one of them being a hydrogen atom, cyano group, nitro group, trifluoromethyl group, or halogen atom.)

The compound of the present invention can be effectively used as an organic luminescent material which emits light ranging from yellow to red in color. In addition, it has a high glass transition point and a high melting point. It is electrically, thermally, and chemically stable. It readily assumes an amorphous glass state and hence it permits vapor deposition.

The compound of the present invention should preferably be one which is represented by the general formula (6) below.

General Formula (6)

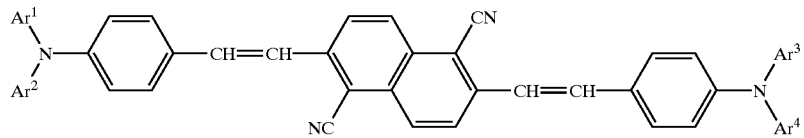

(where $Ar^1$, $Ar^2$, $Ar^3$, and $Ar^4$ are identical or different, each denoting an aryl group which may have a substituent, the aryl group with a substituent being one which is selected from aryl groups represented by the general formula (7), (8), (9), (10), (11), (12), (12'), or (12") below.

General formula (7)

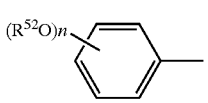

General formula (8)

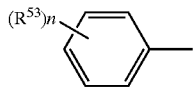

General formula (9)

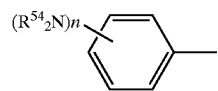

General formula (10)

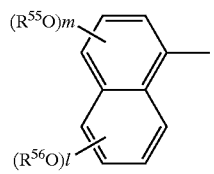

General formula (11)

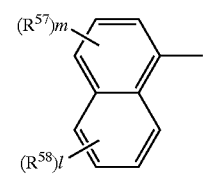

General formula (12)

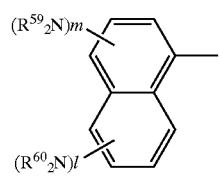

General formula (12′)

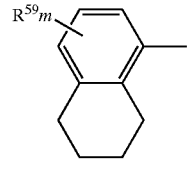

General formula (12″)

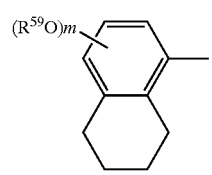

(where $R^{52}$, $R^{53}$, and $R^{54}$ each denotes a saturated or unsaturated hydrocarbon group having one or more carbons (preferably 6 or less carbons, an unsubstituted group has 0 carbon, the same shall apply hereinafter); $R^{55}$, $R^{56}$, $R^{57}$, $R^{58}$, $R^{59}$, and $R^{60}$ are identical or different, each denoting a saturated or unsaturated hydrocarbon group having one or more carbons (preferably 6 or less carbons, an unsubstituted group has 0 carbon, the same shall apply hereinafter); n is an integer of 0 to 6; m is an integer of 0 to 3; and l is an integer of 0 to 4.)

To be concrete, the compound of the present invention should preferably be one which is represented by the general formula (13), (13'), (14), (15), (16), (17), (18), (18'), or (19) below.

General Formula (13)

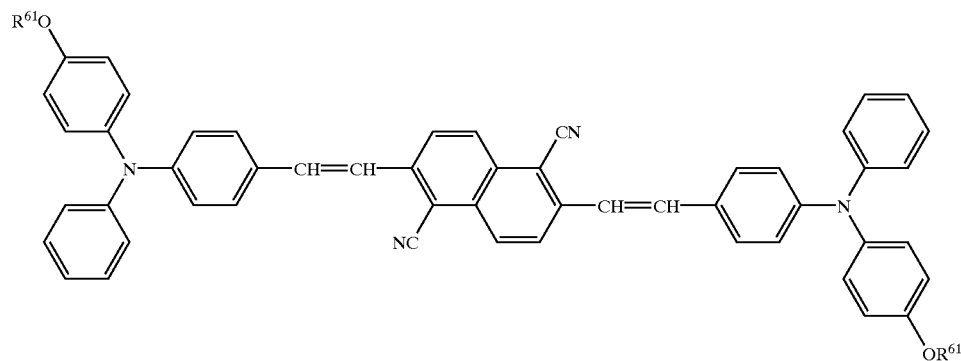

(where $R^{61}$ denotes a saturated or unsaturated hydrocarbon group having 1 to 6 carbon atoms.)
General Formula (13')
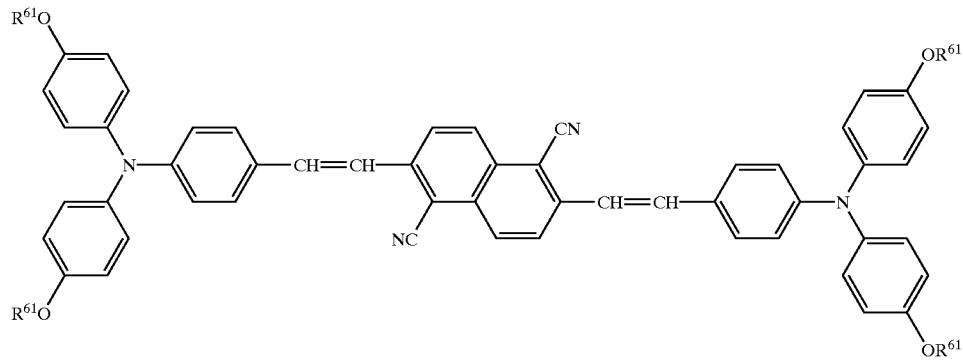
(where $R^{61}$ denotes a saturated or unsaturated hydrocarbon group having 1 to 6 carbon atoms.)
General Formula (14)
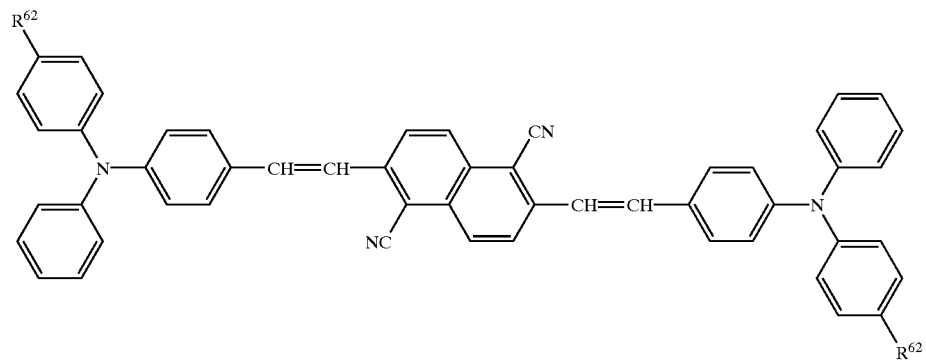
(where $R^{62}$ denotes a saturated or unsaturated hydrocarbon group having 1 to 6 carbon atoms.)
General Formula (15)
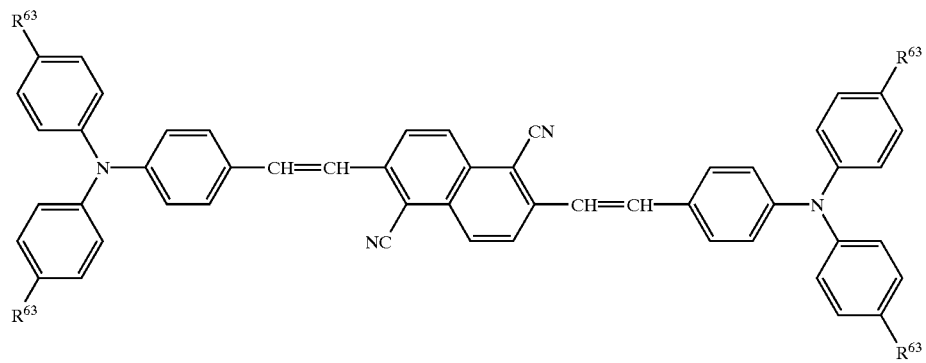

(where $R^{63}$ denotes a saturated or unsaturated hydrocarbon group or hydrocarbon oxy group having 1 to 6 carbon atoms.)
General Formula (16)
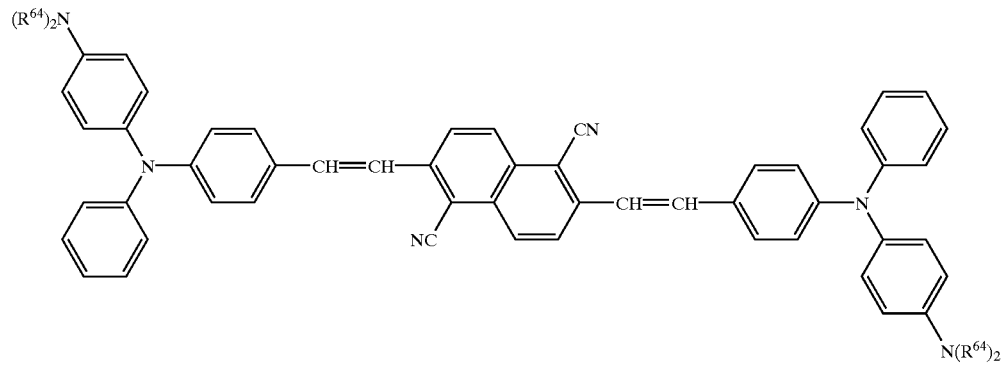
(where $R^{64}$ denotes a saturated or unsaturated hydrocarbon group having 1 to 6 carbon atoms.)
General Formula (17)
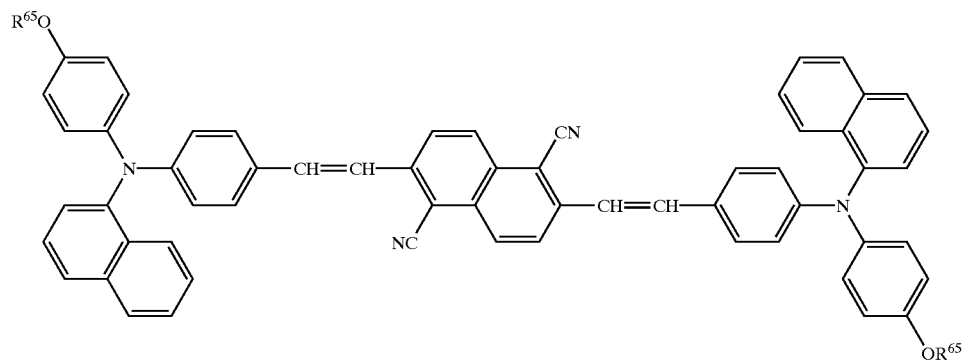
(where $R^{65}$ denotes a saturated or unsaturated hydrocarbon group having 1 to 6 carbon atoms.)
General Formula (18)
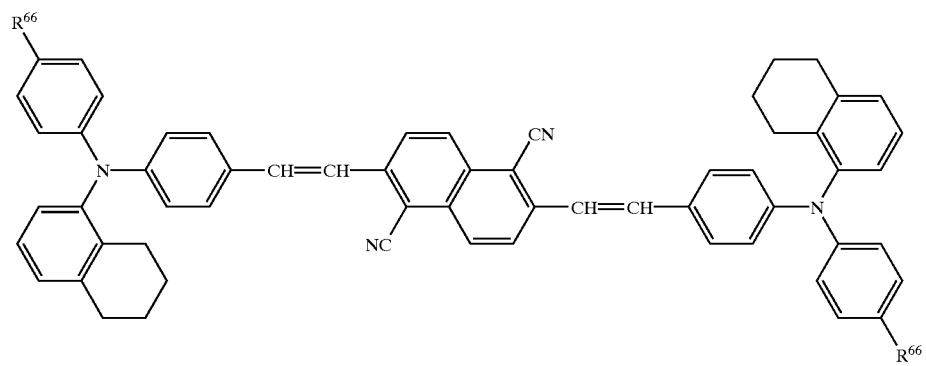

(where $R^{66}$ denotes a saturated or unsaturated hydrocarbon group having 1 to 6 carbon atoms.)

General Formula (18')

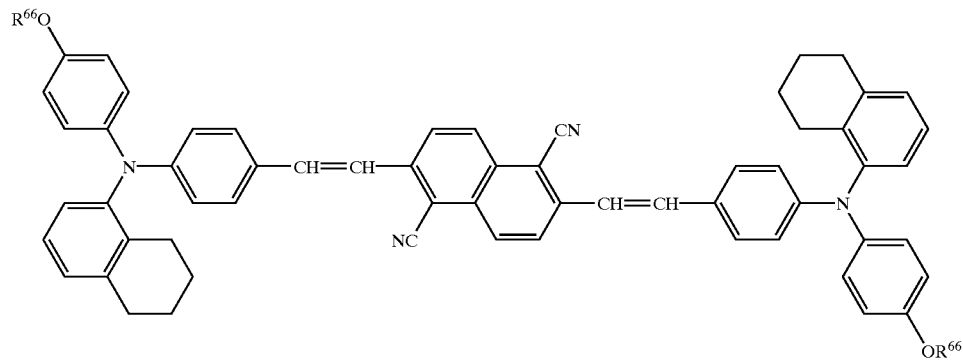

(where $R^{66}$ denotes a saturated or unsaturated hydrocarbon group having 1 to 6 carbon atoms.)

General Formula (19)

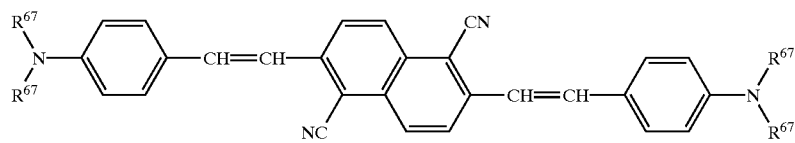

(where $R^{67}$ denotes a saturated or unsaturated hydrocarbon group having 1 to 6 carbon atoms.)

The compound of the present invention is exemplified by those which are represented by the structural formula (20)-1, (20)-2, (20)-3, (20)-4, (20)-5, (20)-6, (20)-7, (20)-8, (20)-9, (20)-10, (20)-11, (20)-12, (20)-12', (20)-13, (20)-14, or (20)-15.

Structural formula (20)-1

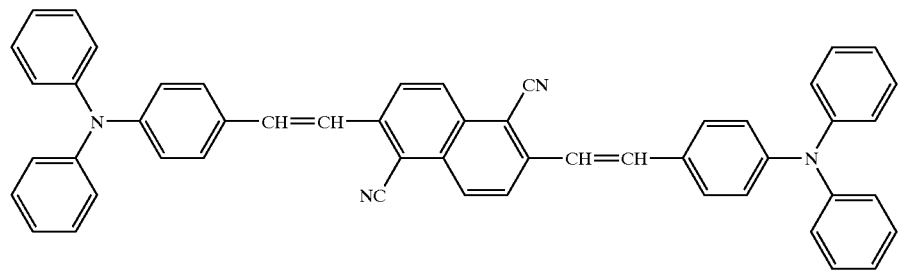

Structural formula (20)-2

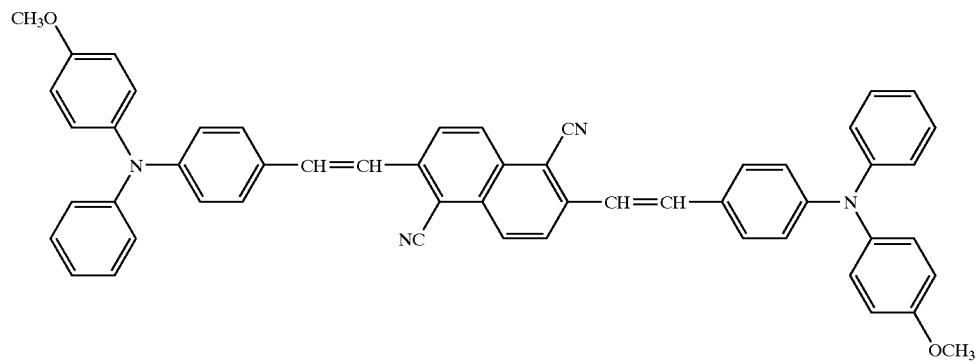

Structural formula (20)-3
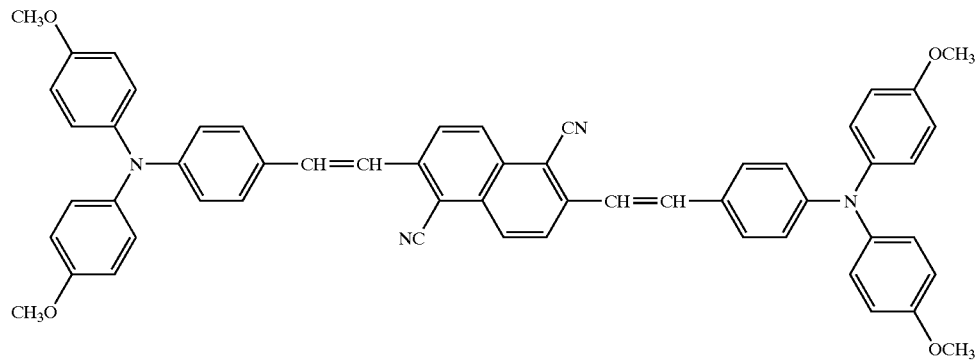
Structural formula (20)-4
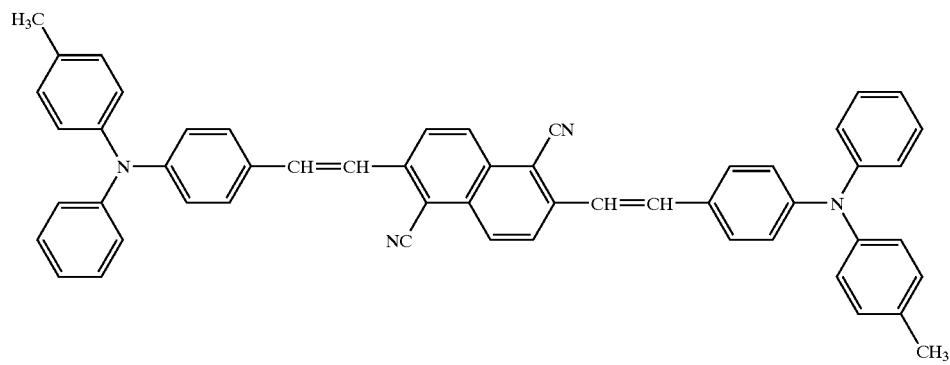
Structural formula (20)-5
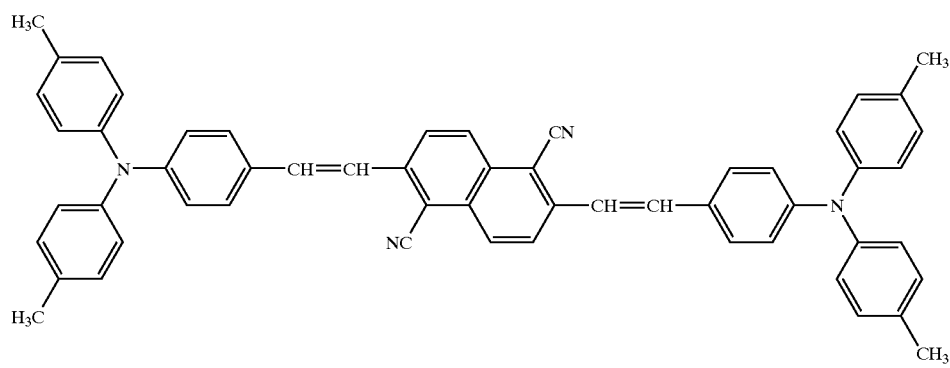
Structural formula (20)-6
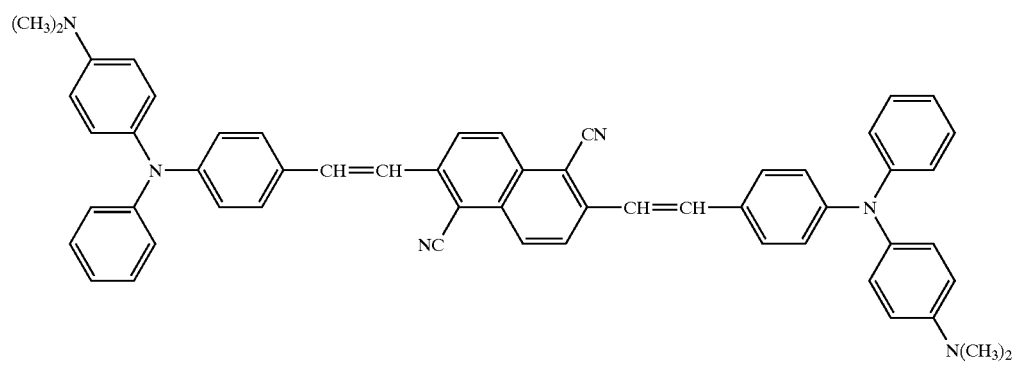

-continued
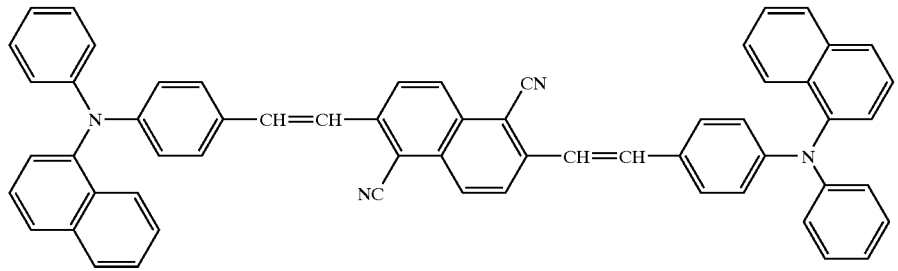
Structural formula (20)-7
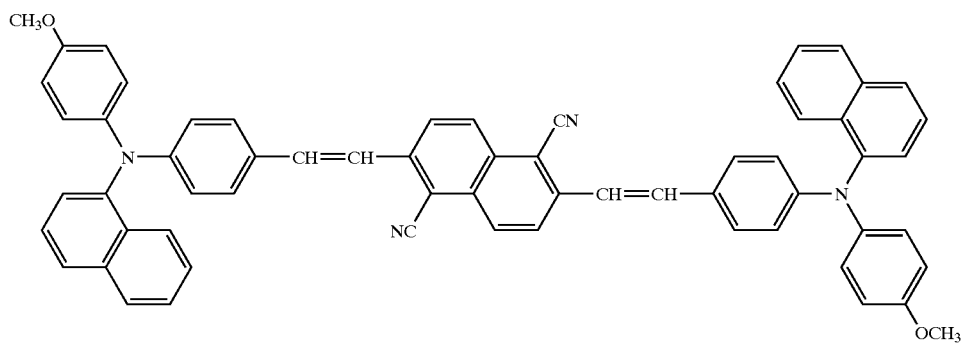
Structural formula (20)-8
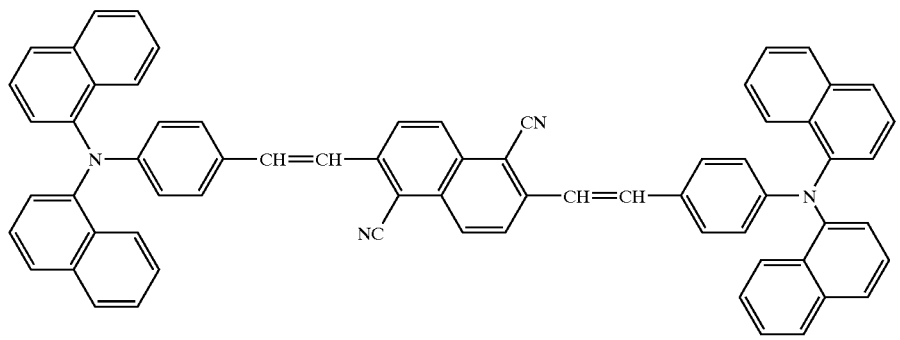
Structural formula (20)-9
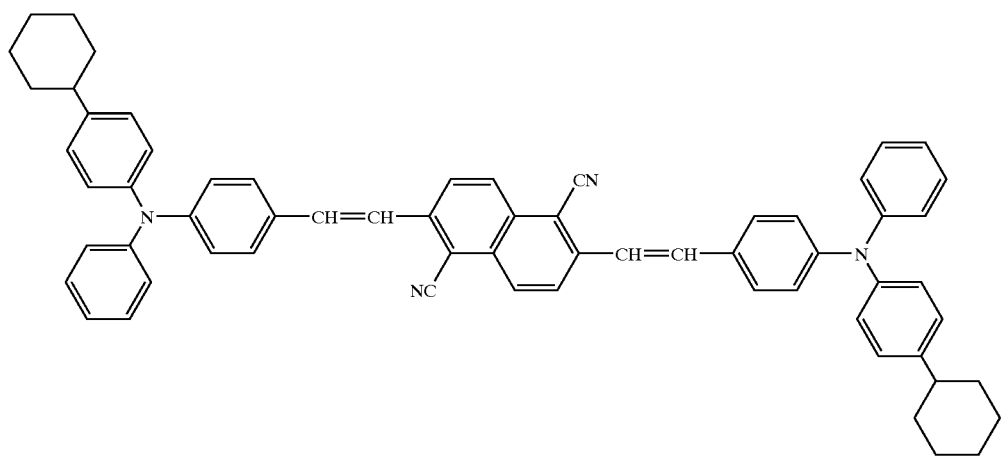
Structural formula (20)-10

Structural formula (20)-11
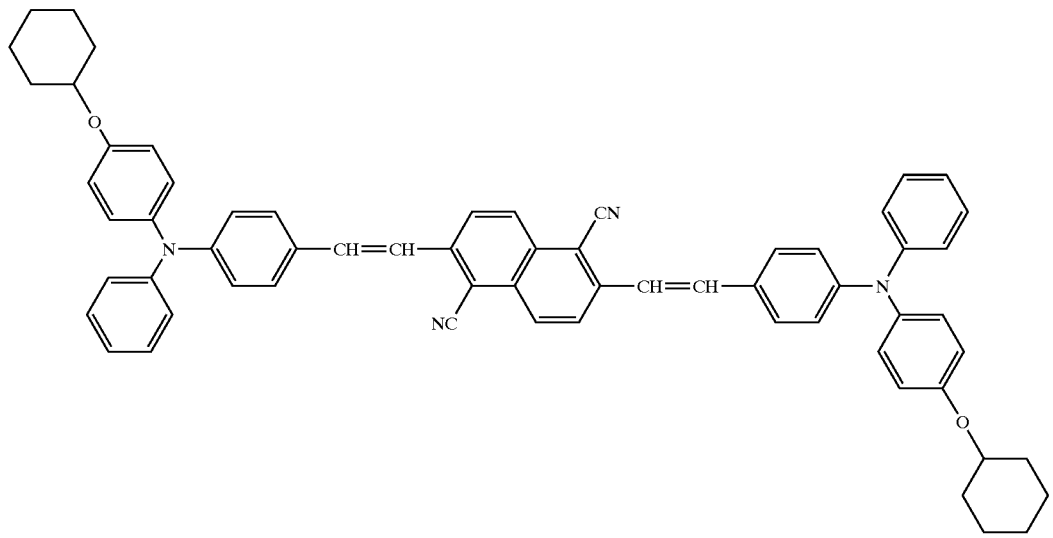
Structural formula (20)-12
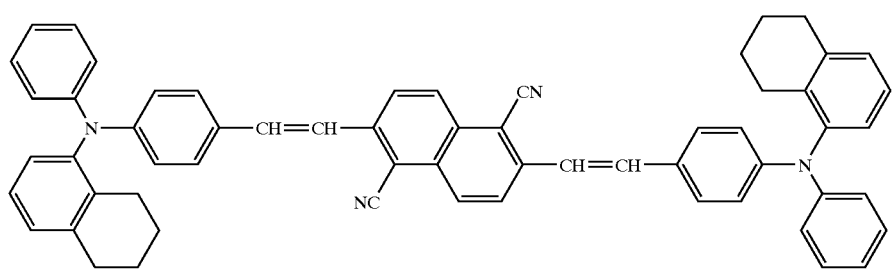
Structural formula (20)-12'
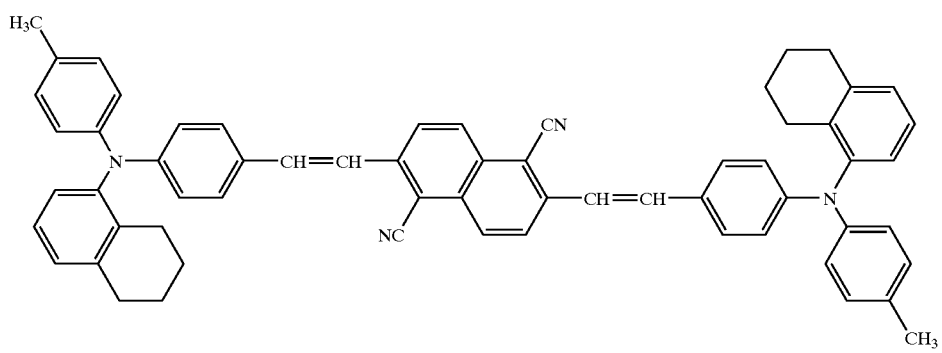
Structural formula (20)-13
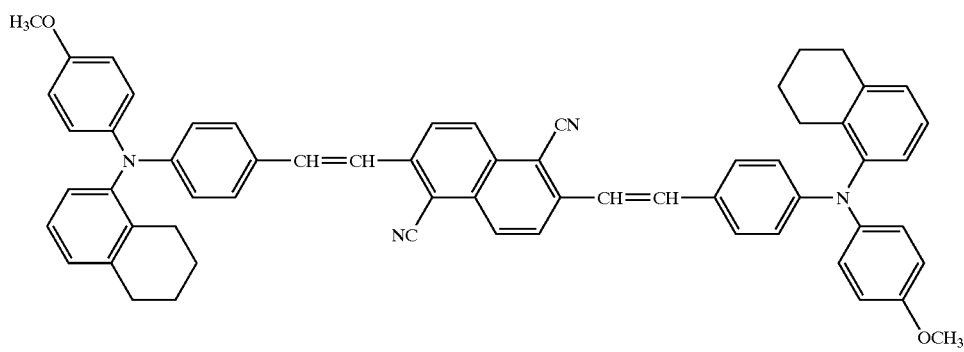

-continued

Structural formula (20)-14

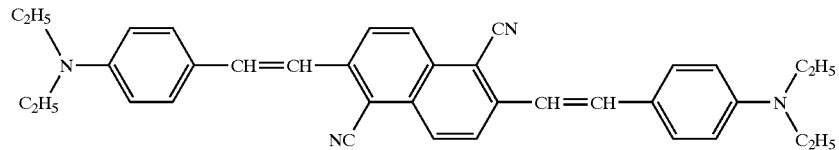

Structural formula (20)-15

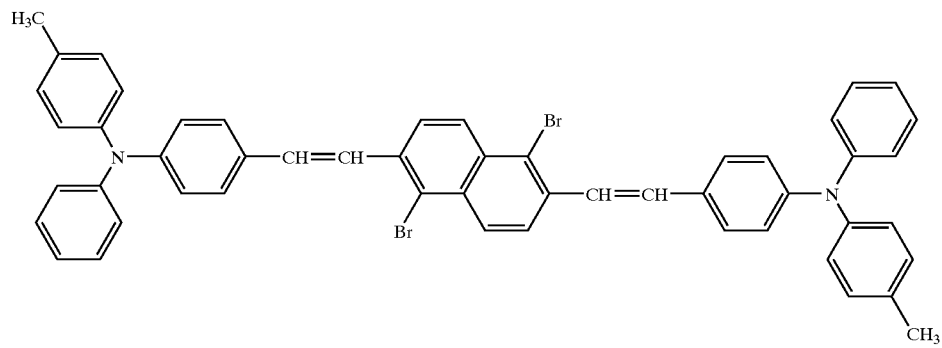

The compound of the present invention should preferably be one which is represented by the general formula below.
General Formula (21)

General formula (21)

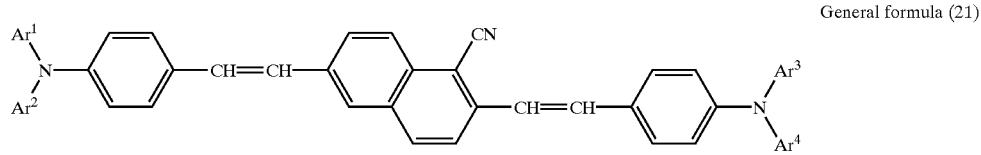

(where $Ar^1$, $Ar^2$, $Ar^3$, and $Ar^4$ are identical or different, each denoting an aryl group which may have a substituent, the aryl group with a substituent being one which is selected from aryl groups represented by the general formula (7), (8), (9), (10), (11), (12), (12'), or (12") below.

General formula (7)

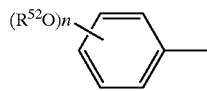

General formula (8)

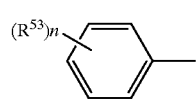

General formula (9)

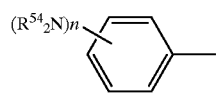

General formula (10)

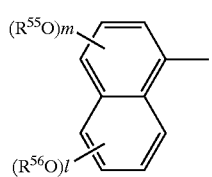

-continued

General formula (11)

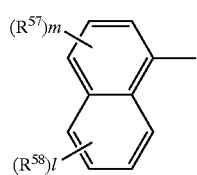

General formula (12)

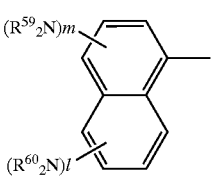

General formula (12')

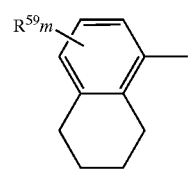

-continued

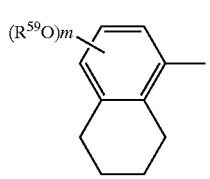

General formula (12″)

(where $R^{52}$, $R^{53}$, and $R^{54}$ each denotes a saturated or unsaturated hydrocarbon group having one or more carbons; $R^{55}$, $R^{56}$, $R^{57}$, $R^{58}$, $R^{59}$, and $R^{60}$ are identical or different, each denoting a saturated or unsaturated hydrocarbon group having one or more carbons; n is an integer of 0 to 6; m is an integer of 0 to 3; and l is an integer of 0 to 4.))

To be more concrete, the compound of the present invention should preferably be one which is represented by the general formula (22), (23), (24), (25), (26), (27), (27'), or (28) below.

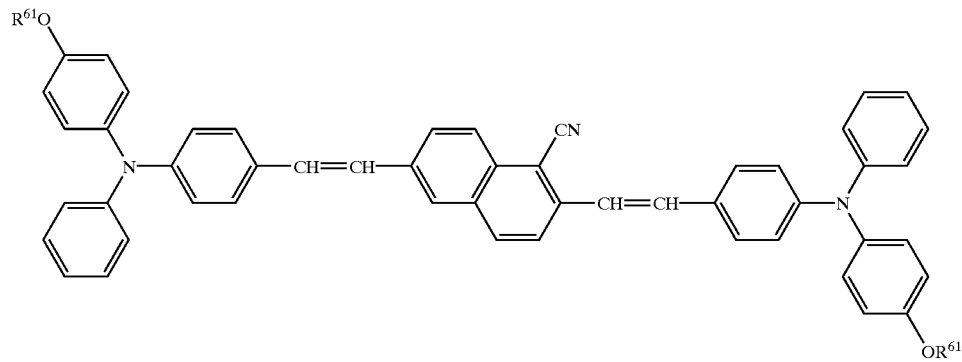

General formula (22)

(where $R^{61}$ denotes a saturated or unsaturated hydrocarbon group having 1 to 6 carbon atoms.)

General Formula (23)

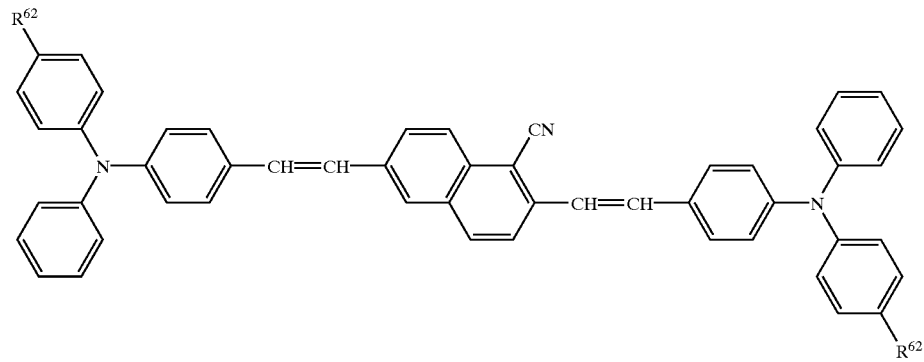

General formula (23)

(where $R^{62}$ denotes a saturated or unsaturated hydrocarbon group having 1 to 6 carbon atoms.)

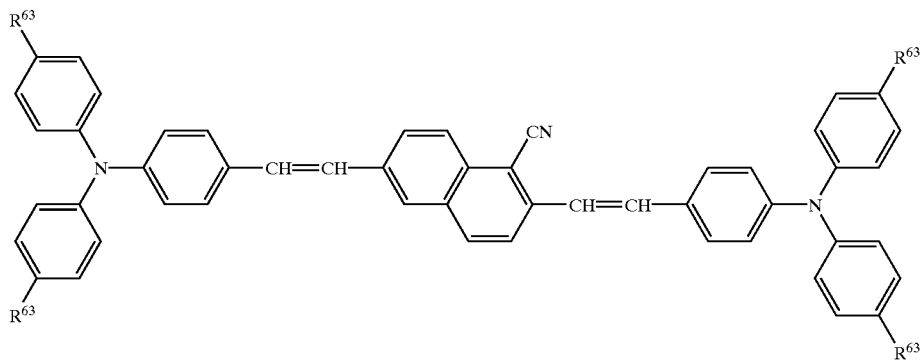
General formula (24)
(where $R^{63}$ denotes a saturated or unsaturated hydrocarbon group or hydrocarbon oxy group having 1 to 6 carbon atoms.)
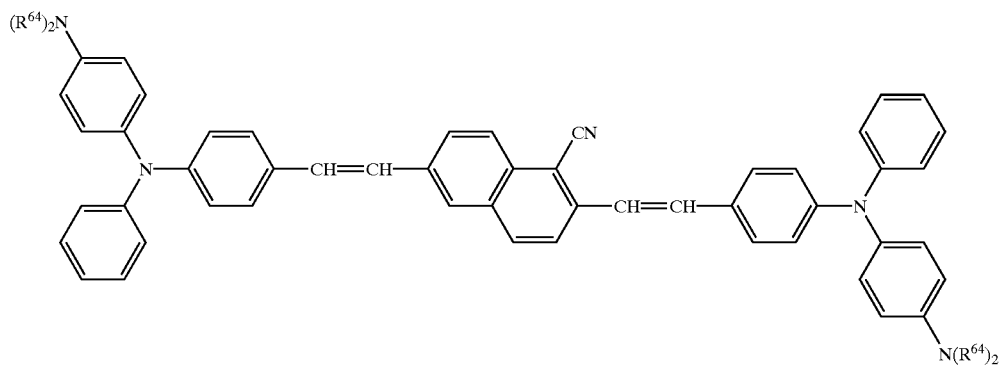
General formula (25)
(where $R^{64}$ denotes a saturated or unsaturated hydrocarbon group having 1 to 6 carbon atoms.)
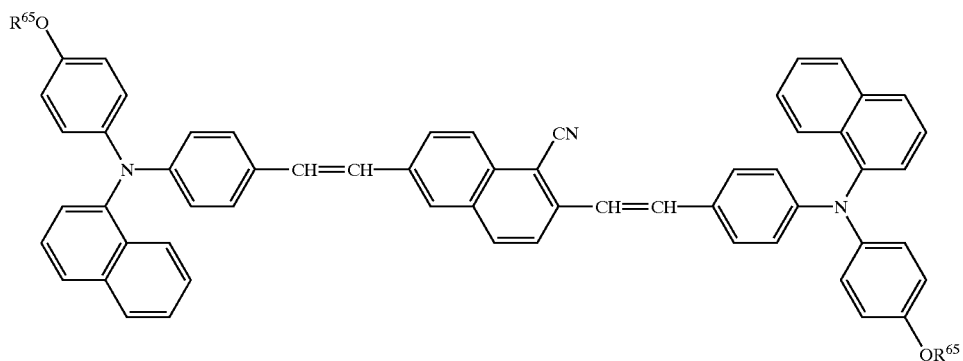
General formula (26)
(where $R^{65}$ denotes a saturated or unsaturated hydrocarbon group having 1 to 6 carbon atoms.)

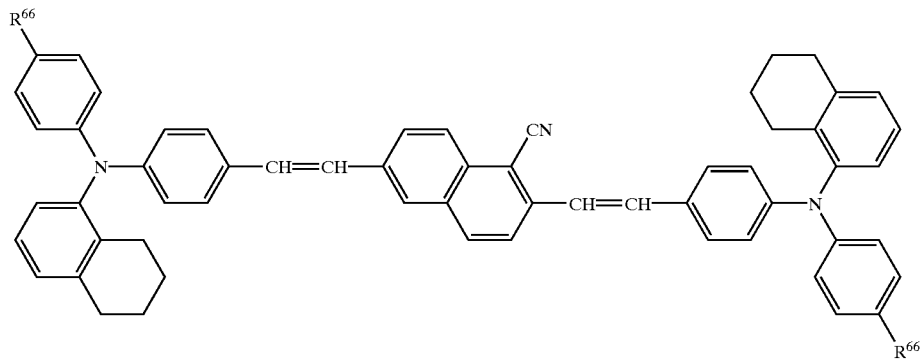

General formula (27)

(where $R^{66}$ denotes a saturated or unsaturated hydrocarbon group having 1 to 6 carbon atoms.)

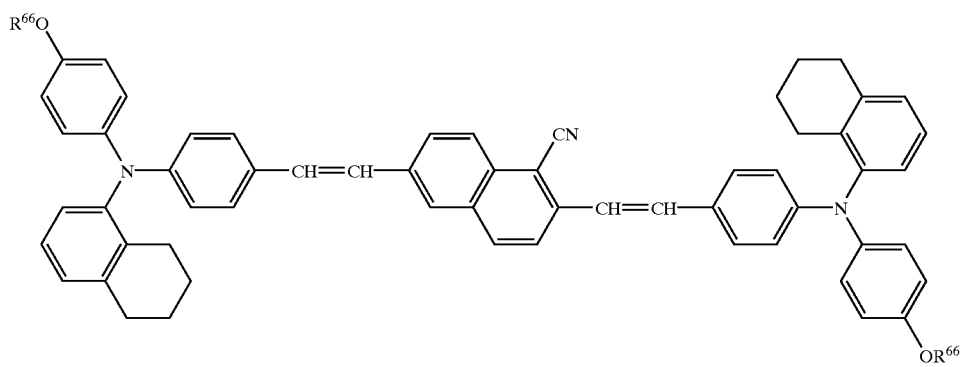

General formula (27')

(where $R^{66}$ denotes a saturated or unsaturated hydrocarbon group having 1 to 6 carbon atoms.)

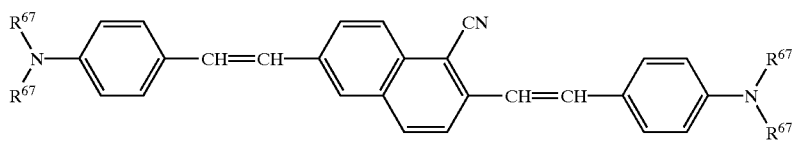

General formula (28)

(where $R^{67}$ denotes a saturated or unsaturated hydrocarbon group having 1 to 6 carbon atoms.)

The compound of the present invention is exemplified by those which are represented by the structural formula (29)-1, (29)-2, (29)-3, (29)-4, (29)-5, (29)-6, (29)-7, (29)-8, (29)-9, (29)-10, (25)-11, (29)-12, (29)-12', (29)-13, (29)-14, or (29)-15 below.

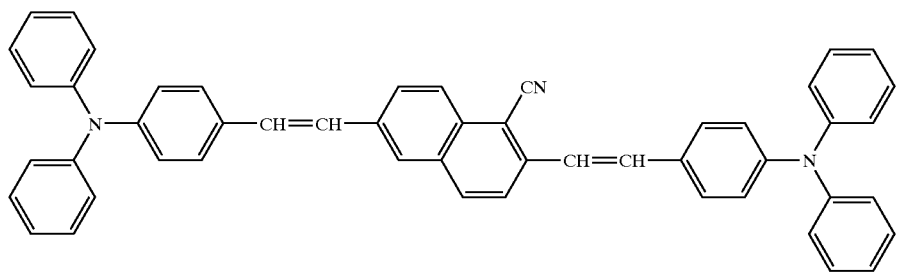

Structural formula (29)-1

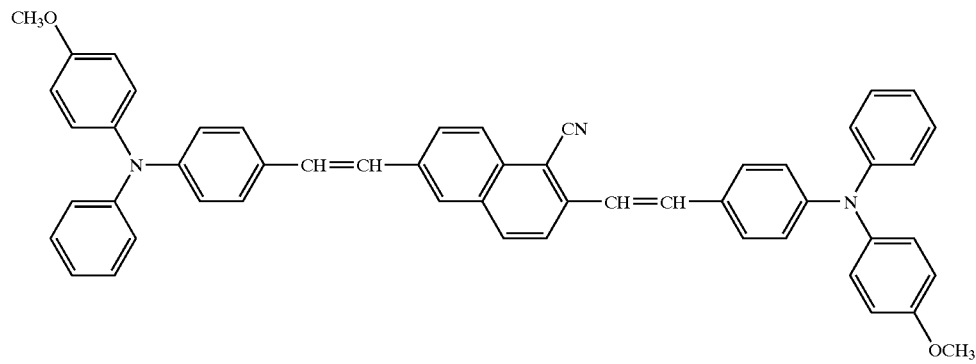
Structural formula (29)-2
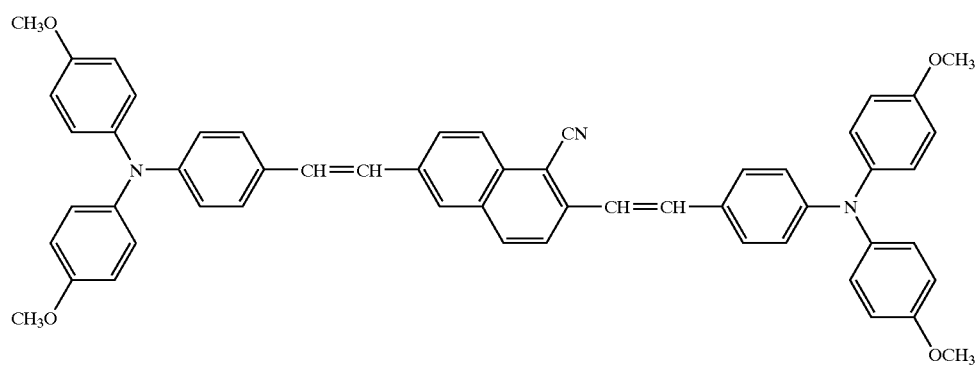
Structural formula (29)-3
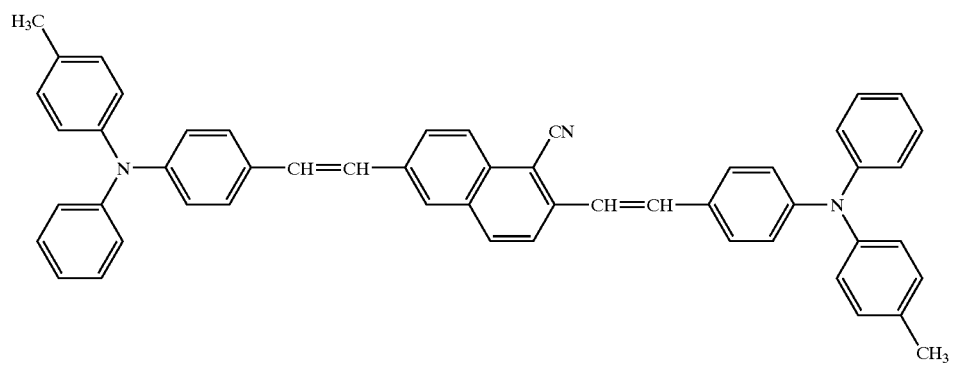
Structural formula (29)-4
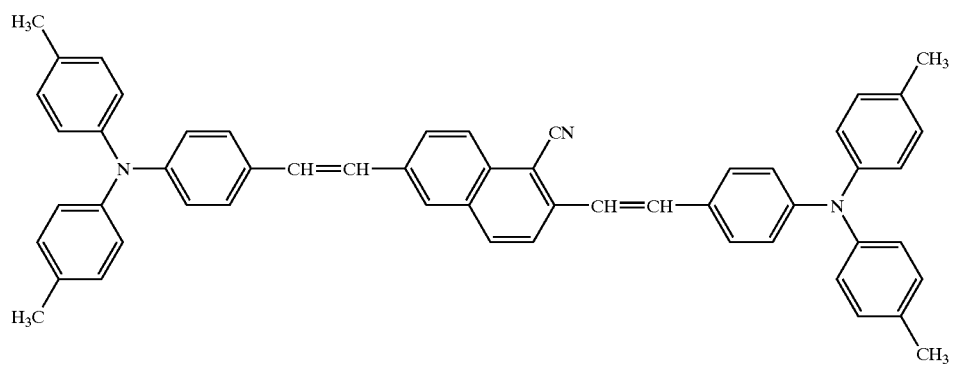
Structural formula (29)-5

Structural formula (29)-6
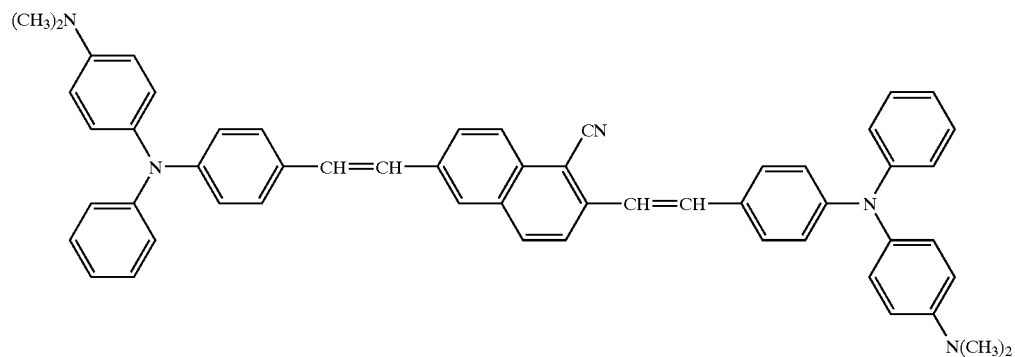
Structural formula (29)-7
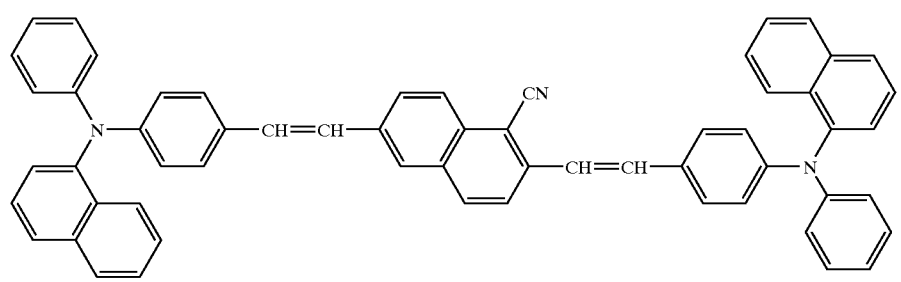
Structural formula (29)-8
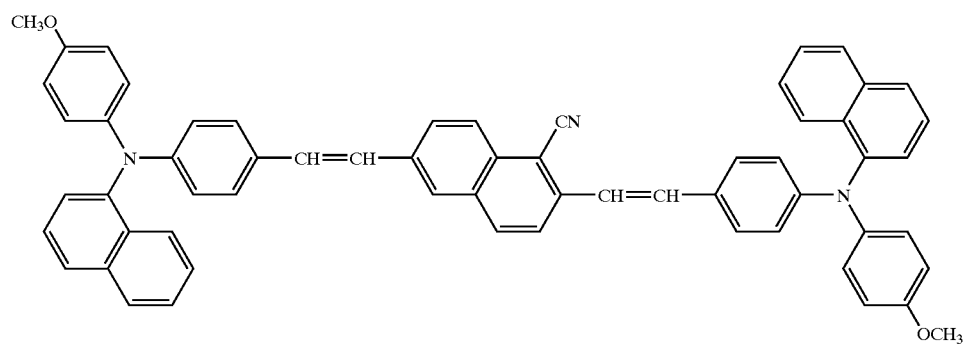
Structural formula (29)-9
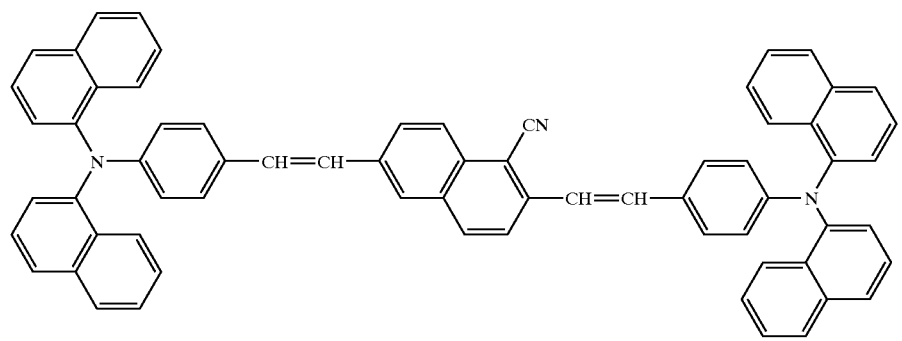

Structural formula (29)-10
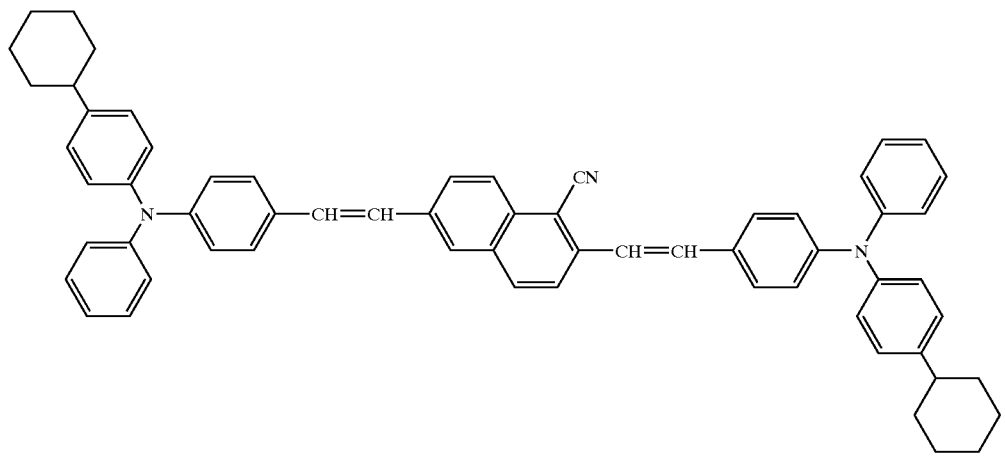
Structural formula (29)-11
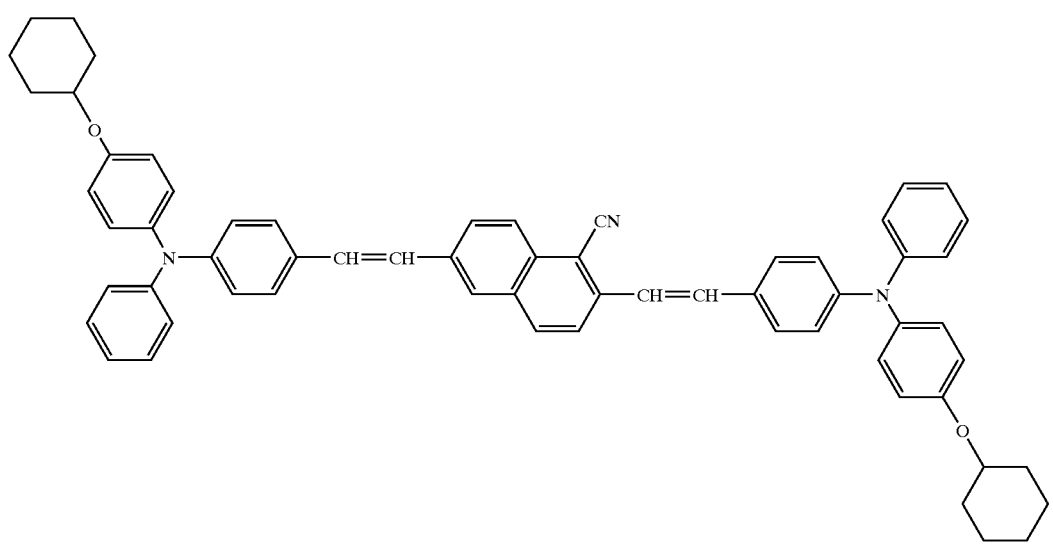
Structural formula (29)-12
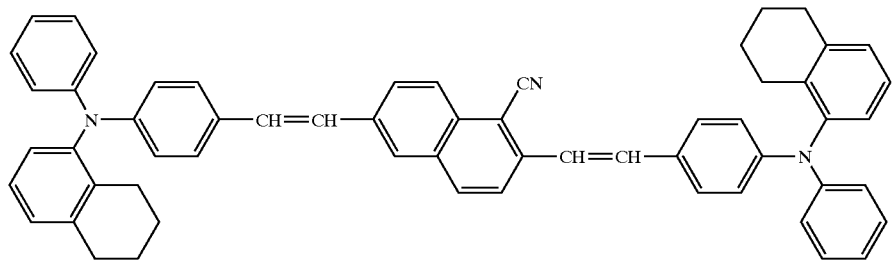
Structural formula (29)-12'
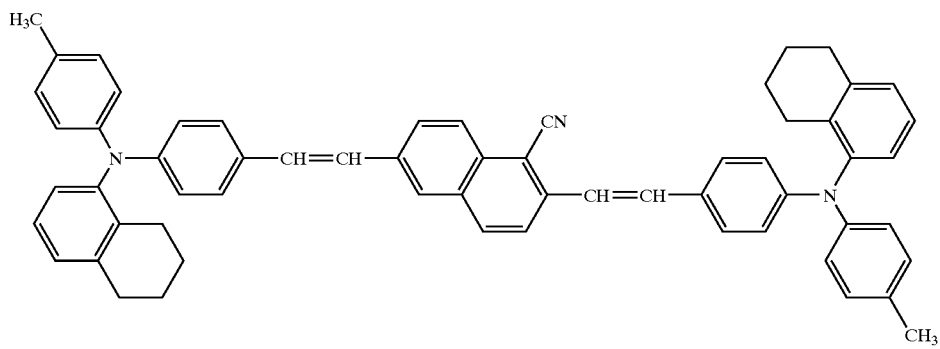

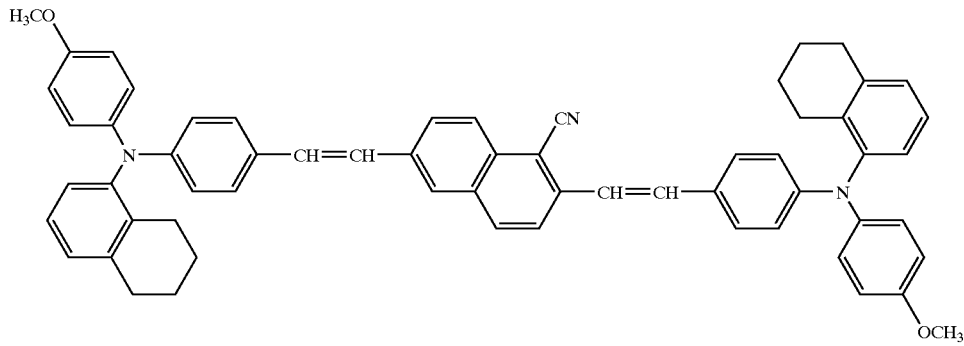

Structural formula (29)-13

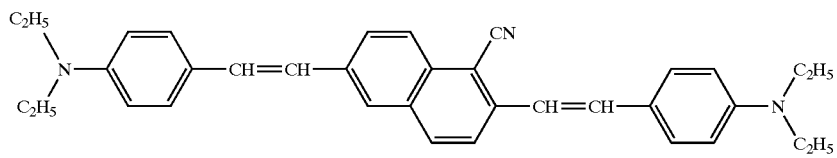

Structural formula (29)-14

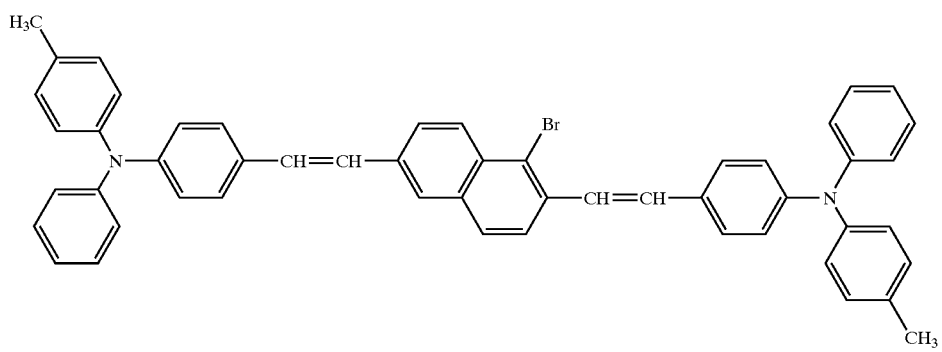

Structural formula (29)-15

The compound of the present invention should preferably be one which is represented by the general formula (30) below.

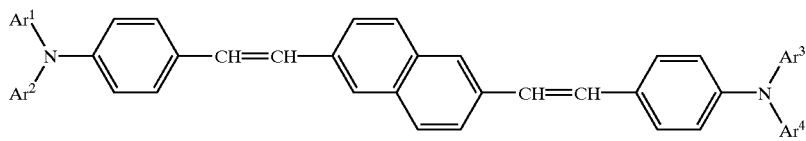

General formula (30)

(where $Ar^1$, $Ar^2$, $Ar^3$, and $Ar^4$ are identical or different, each denoting an aryl group which may have a substituent, the aryl group with a substituent being one which is selected from aryl groups represented by the general formula (7), (8), (9), (10), (11), (12), (12'), or (12") below.

General formula (7)

(R$^{52}$O)$n$—

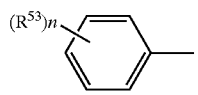

General formula (8)

(R$^{53}$)$n$—

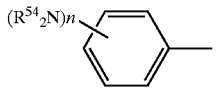

General formula (9)

(R$^{54}_2$N)$n$—

General formula (12)

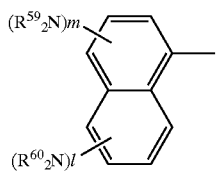

General formula (12′)

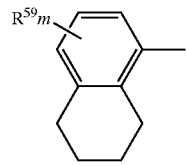

General formula (12″)

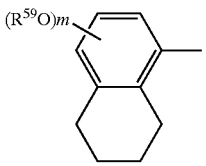

(where $R^{52}$, $R^{53}$, and $R^{54}$ each denotes a saturated or unsaturated hydrocarbon group having one or more carbons; $R^{55}$, $R^{56}$, $R^{57}$, $R^{58}$, $R^{59}$, and $R^{60}$ are identical or different, each denoting a saturated or unsaturated hydrocarbon group having one or more carbon atoms; n is an integer of 0 to 6; m is an integer of 0 to 3; and l is an integer of 0 to 4.)

To be more concrete, the compound of the present invention should preferably be one which is represented by the general formula (31), (32), (33), (34), (35), (36), (36′), or (37) below.

General formula (31)

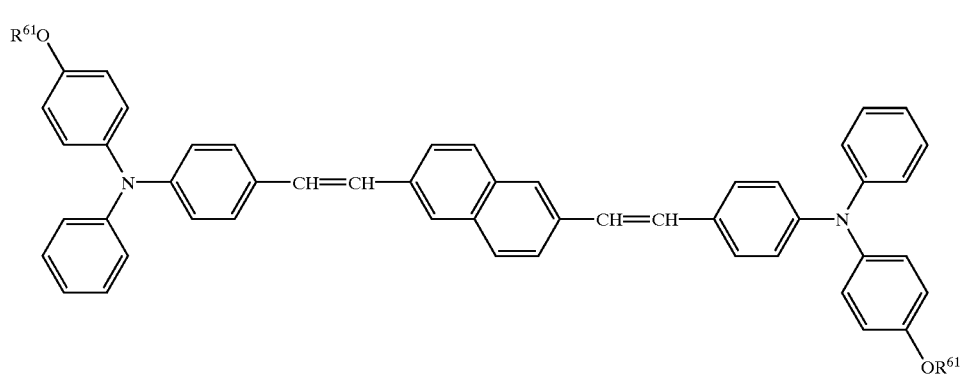

(where $R^{61}$ denotes a saturated or unsaturated hydrocarbon group having 1 to 6 carbon atoms.)

General formula (32)

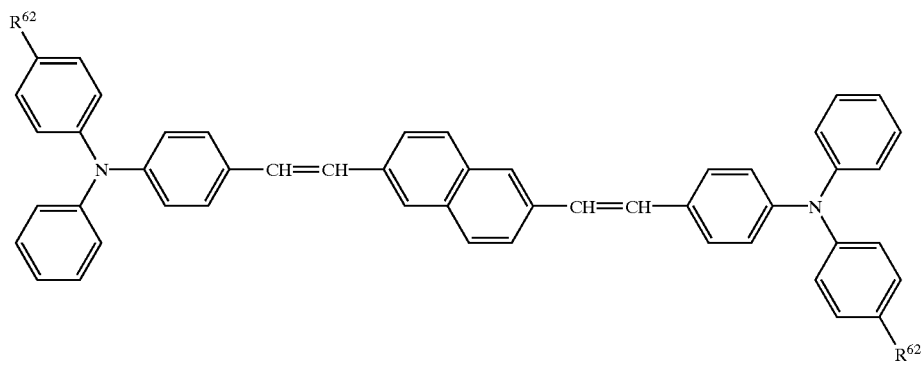

(where $R^{62}$ denotes a saturated or unsaturated hydrocarbon group having 1 to 6 carbon atoms.)

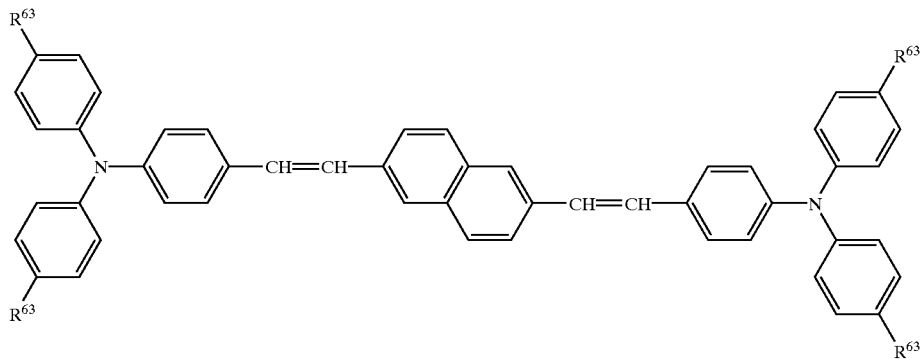
General formula (33)
(where R⁶³ denotes a saturated or unsaturated hydrocarbon group or hydrocarbon oxy group having 1 to 6 carbon atoms.)
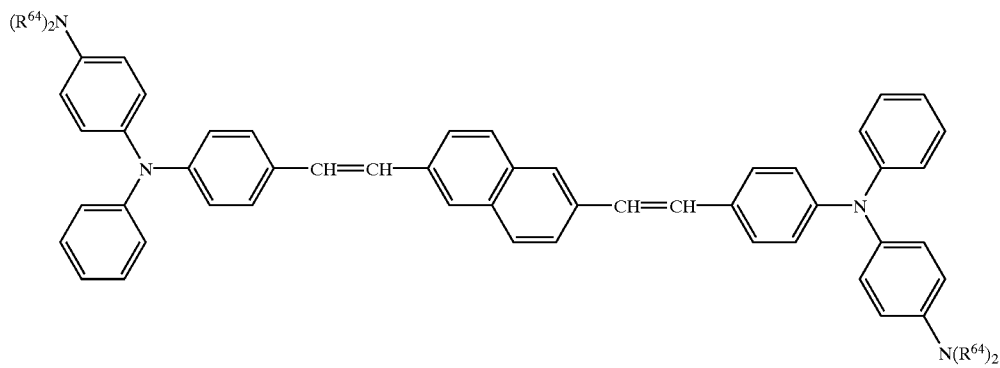
General formula (34)
(where R⁶⁴ denotes a saturated or unsaturated hydrocarbon group having 1 to 6 carbon atoms.)
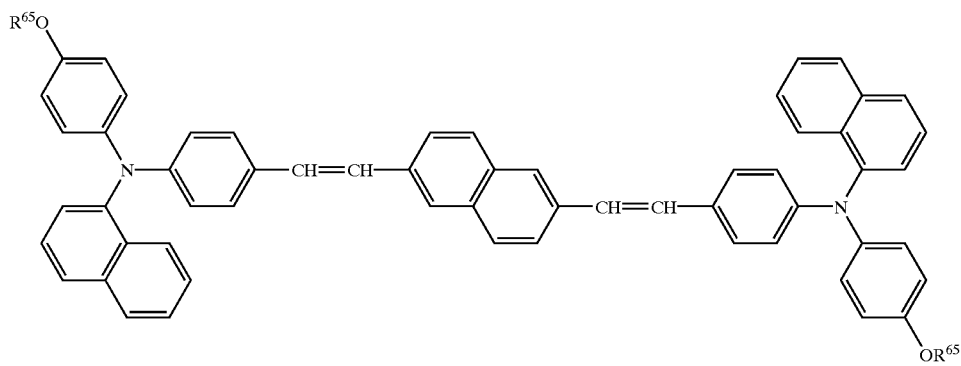
General formula (35)
(where R⁶⁵ denotes a saturated or unsaturated hydrocarbon group having 1 to 6 carbon atoms.)

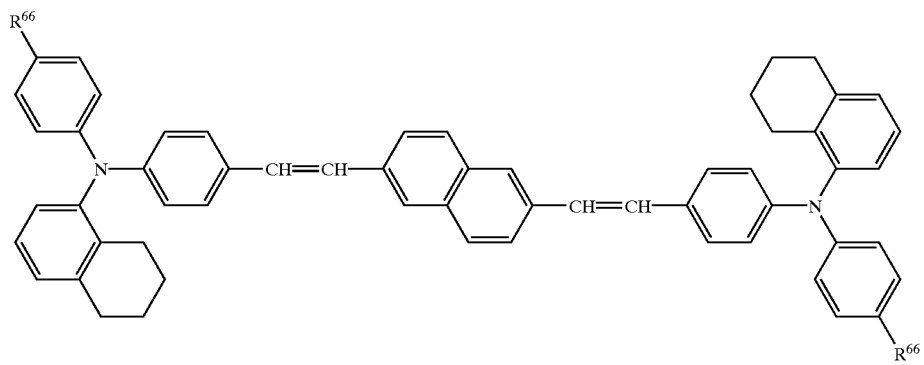

General formula (36)

(where $R^{66}$ denotes a saturated or unsaturated hydrocarbon group having 1 to 6 carbon atoms.)

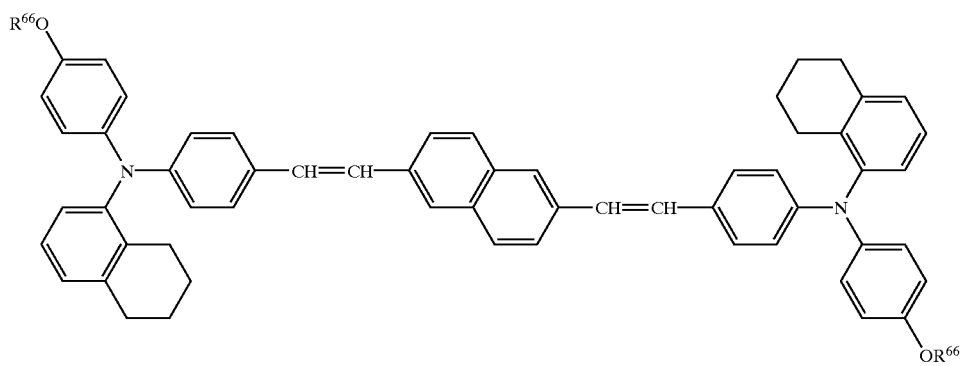

General formula (36')

(where $R^{66}$ denotes a saturated or unsaturated hydrocarbon group having 1 to 6 carbon atoms.)

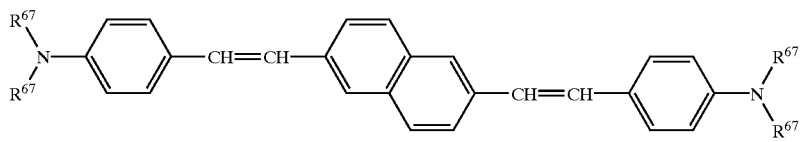

General formula (37)

(where $R^{67}$ denotes a saturated or unsaturated hydrocarbon group having 1 to 6 carbon atoms.)

The compound of the present invention is exemplified by those which are represented by the structural formula (38)-1, (38)-2, (38)-3, (38)-4, (38)-5, (38)-6, (38)-7, (38)-8, (38)-9, (38)-10, (38)-11, (38)-12, (38)-12', (38)-13, or (38)-14 below.

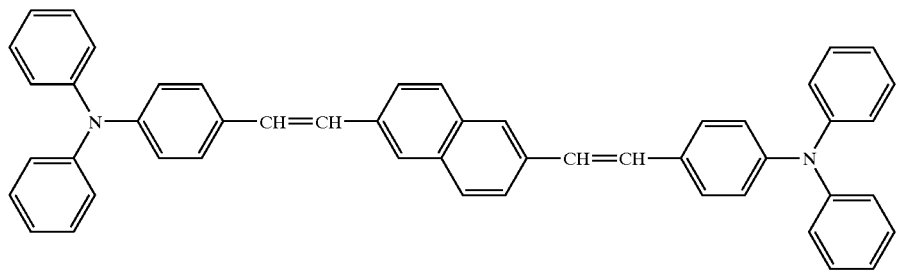

Structural formula (38)-1

-continued
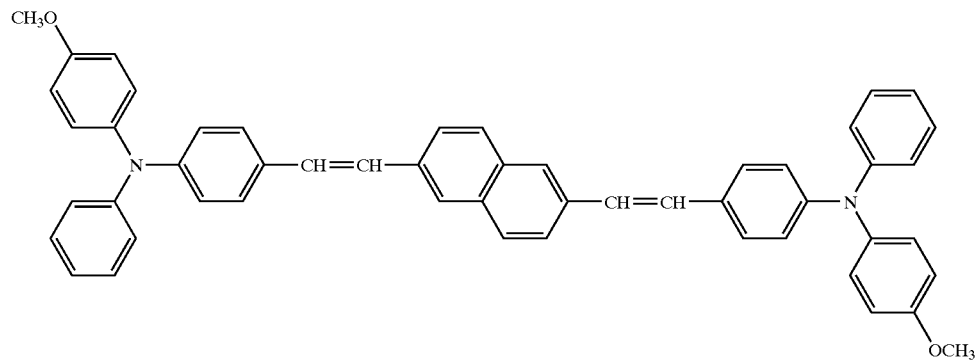
Structural formula (38)-2
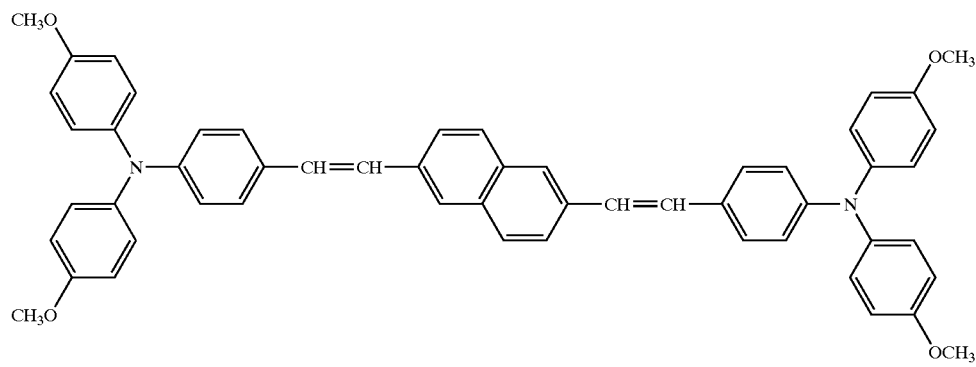
Structural formula (38)-3
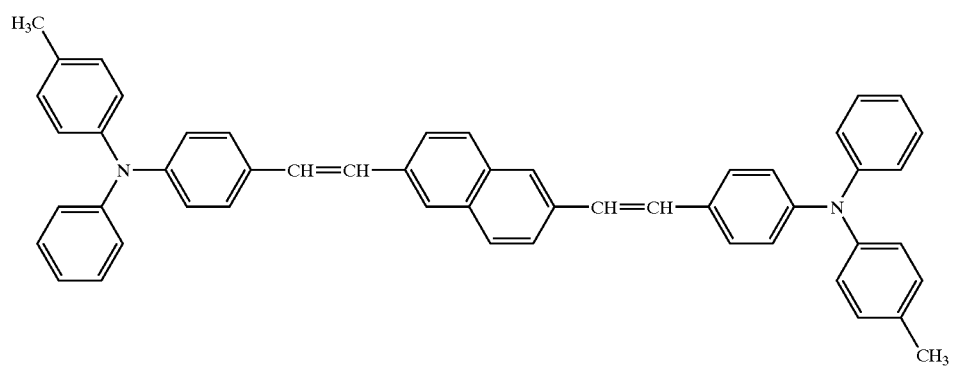
Structural formula (38)-4
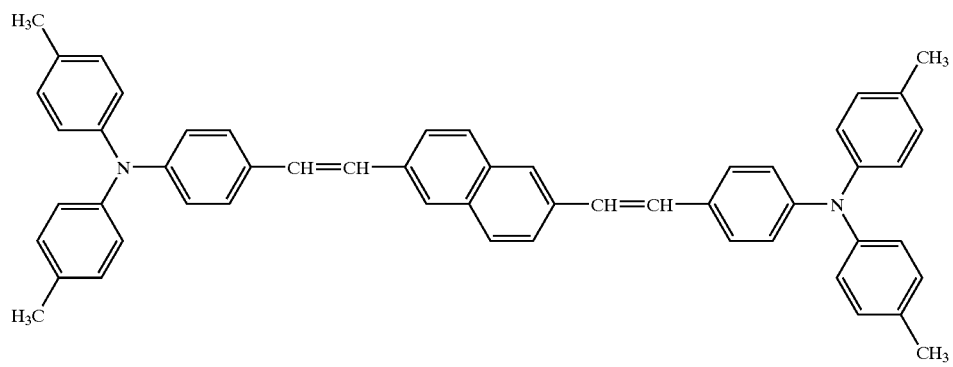
Structural formula (38)-5

Structural formula (38)-6
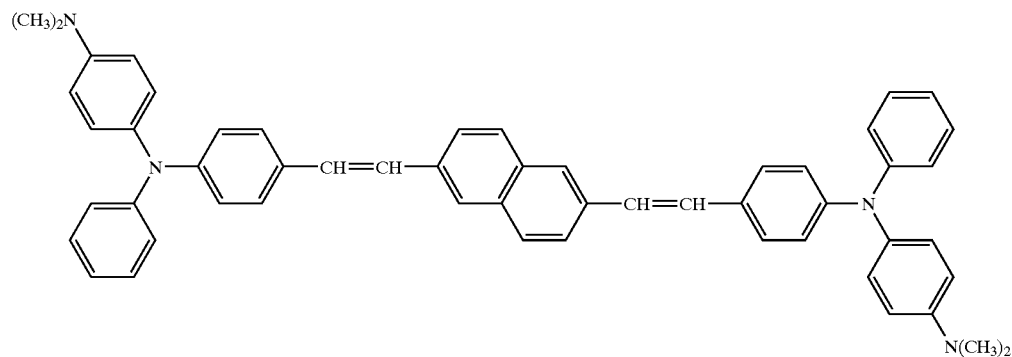
Structural formula (38)-7
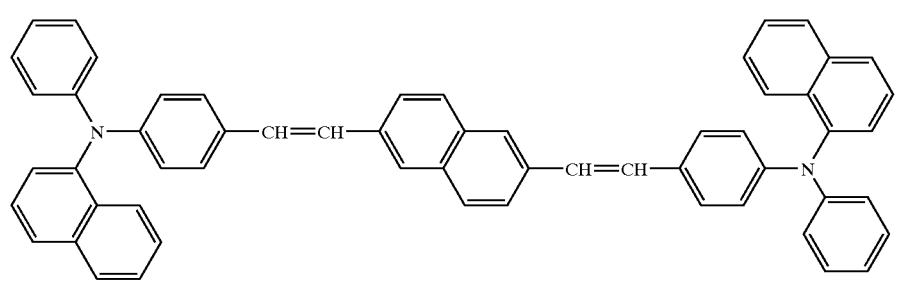
Structural formula (38)-8
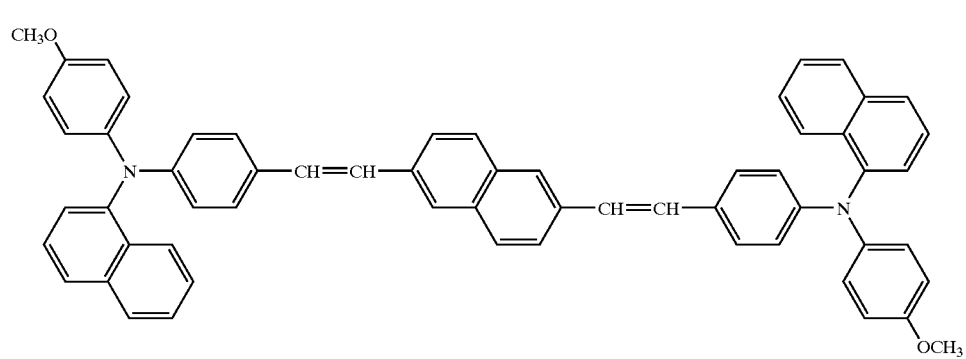
Structural formula (38)-9
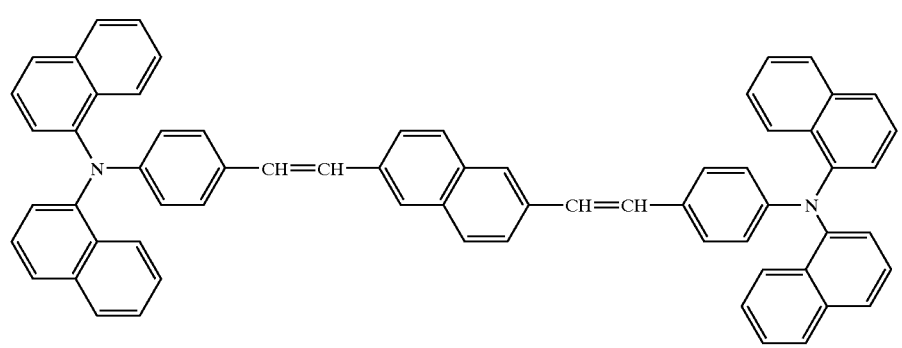

Structural formula (38)-10
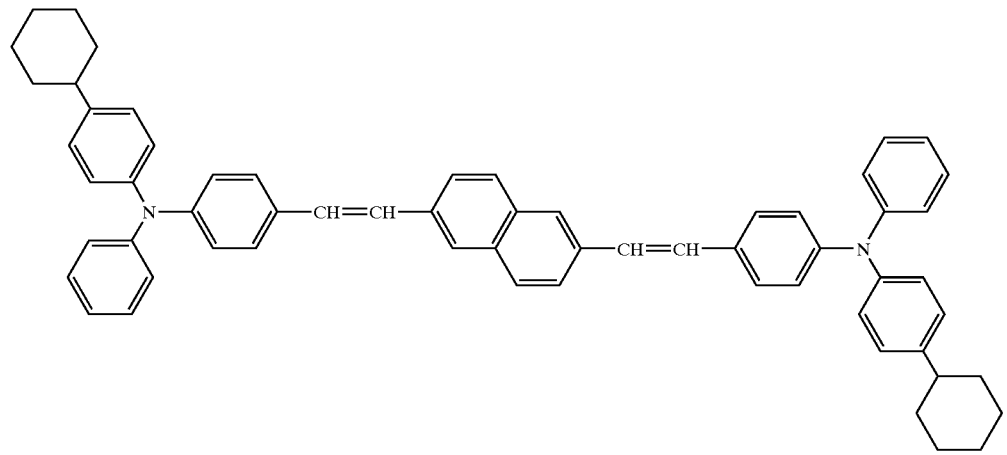
Structural formula (38)-11
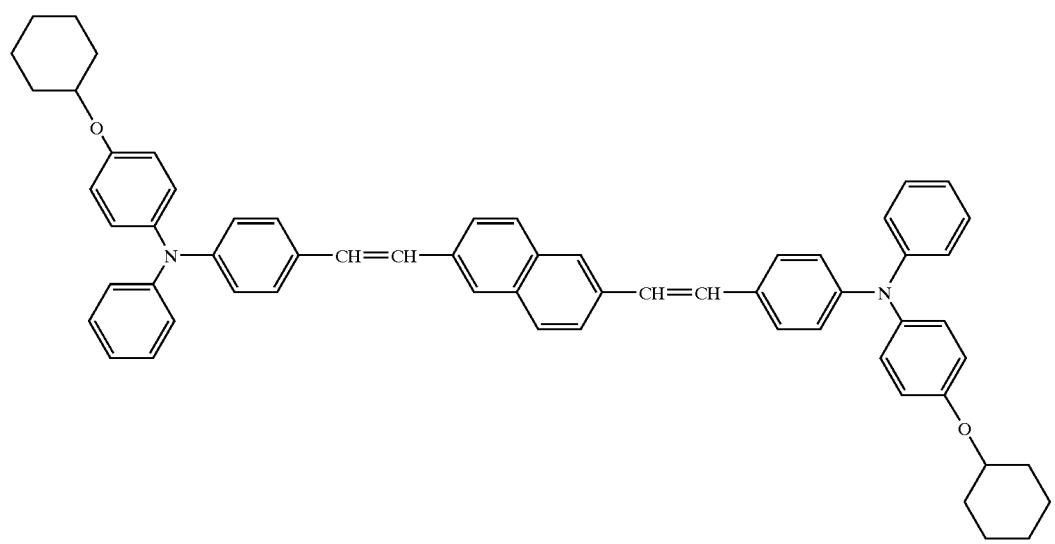
Structural formula (38)-12
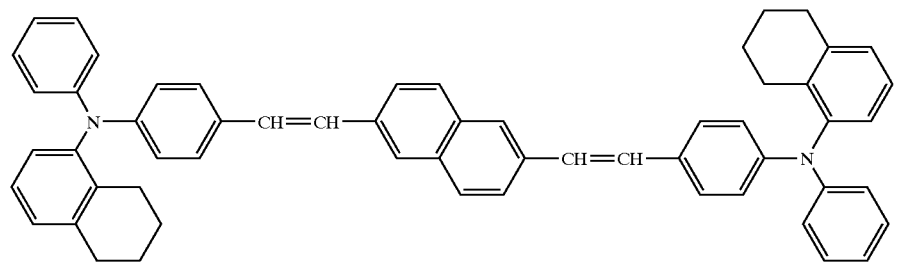
Structural formula (38)-12'
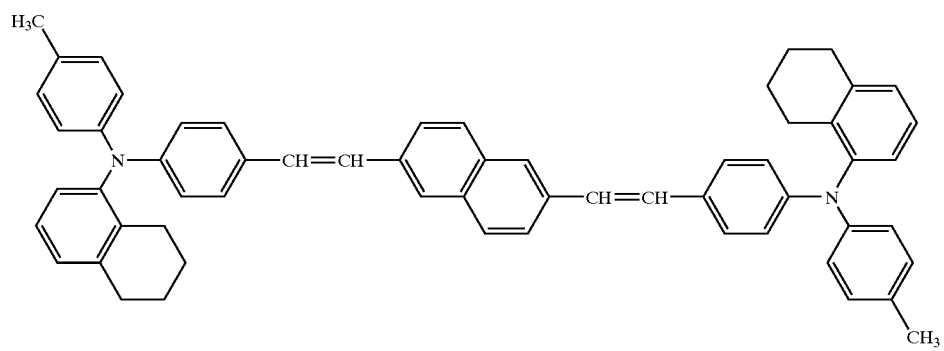

Structural formula (38)-13
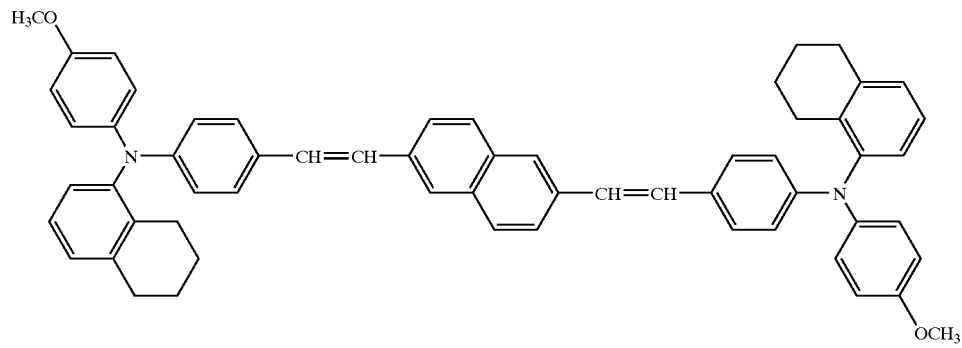
Structural formula (38)-14
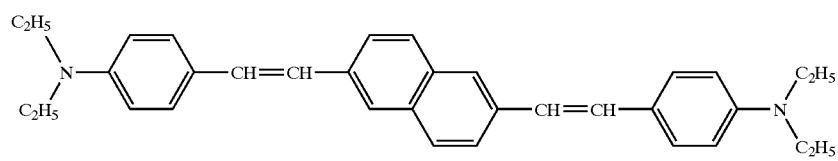
Other examples of the compound of the present invention are listed in the following.
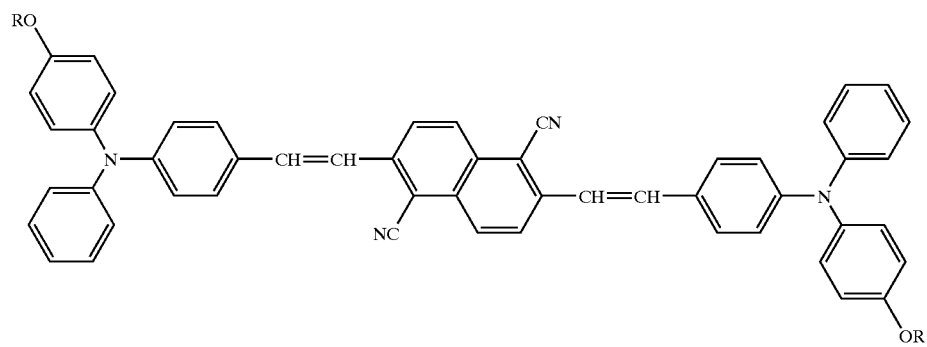
(R = $C_2H_5$, i-$C_3H_7$, i-$C_4H_9$, t-$C_4H_9$, cyclo-$C_6H_{10}$, $C_6H_5$)
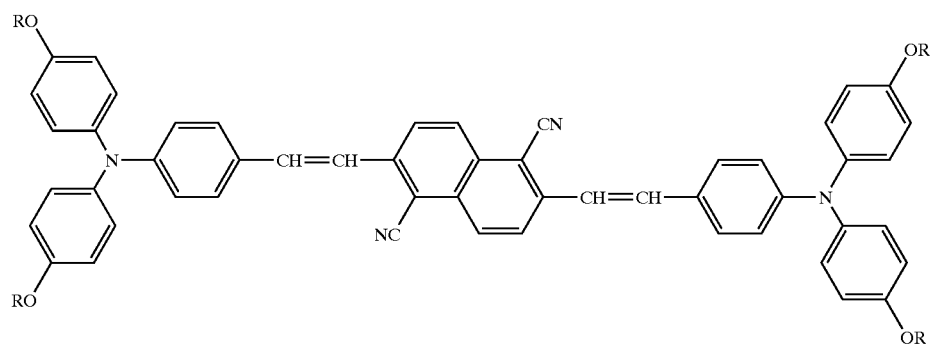
(R = $CH_3$, $C_2H_5$, i-$C_3H_7$, i-$C_4H_9$, t-$C_4H_9$, cyclo-$C_6H_{10}$, $C_6H_5$)

-continued
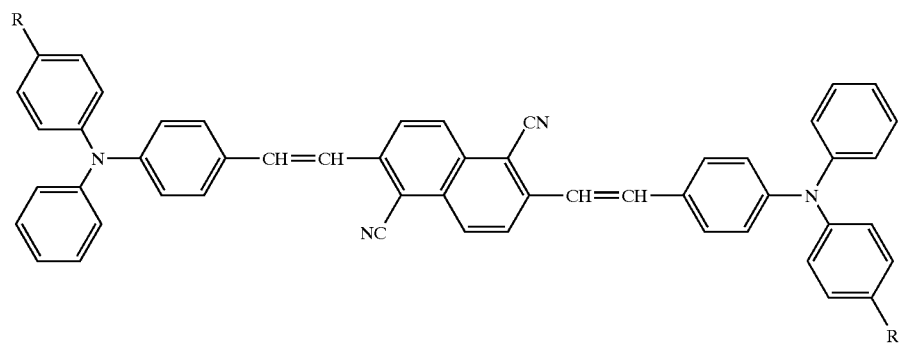
(R = C₂H₅, i-C₃H₇, i-C₄H₉, t-C₄H₉, cyclo-C₆H₁₀, C₆H₅)
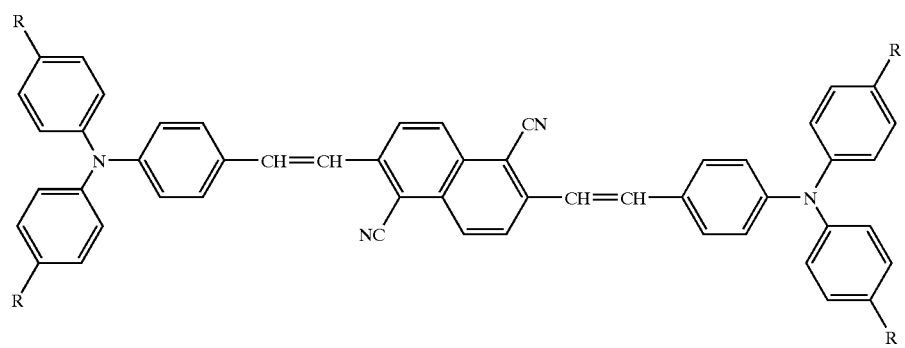
(R = C₂H₅, i-C₃H₇, i-C₄H₉, t-C₄H₉, cyclo-C₆H₁₀, C₆H₅)
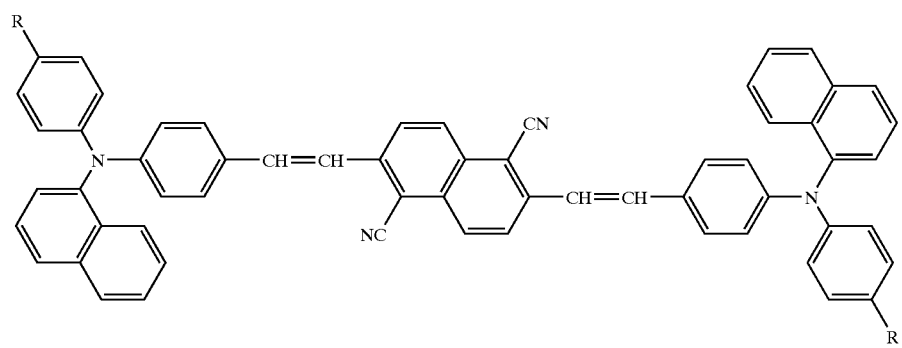
(R = C₂H₅, i-C₃H₇, i-C₄H₉, t-C₄H₉, cyclo-C₆H₁₀, C₆H₅)
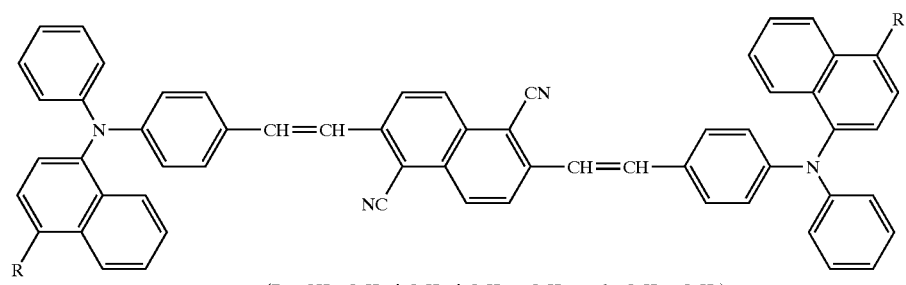
(R = CH₃, C₂H₅, i-C₃H₇, i-C₄H₉, t-C₄H₉, cyclo-C₆H₁₀, C₆H₅)

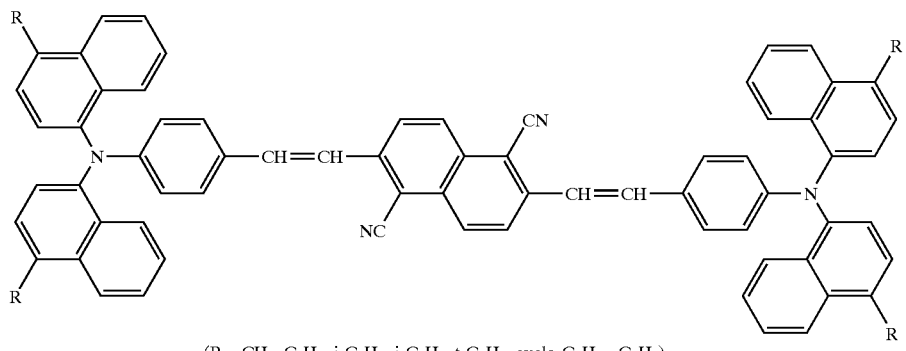
(R = CH₃, C₂H₅, i-C₃H₇, i-C₄H₉, t-C₄H₉, cyclo-C₆H₁₀, C₆H₅)
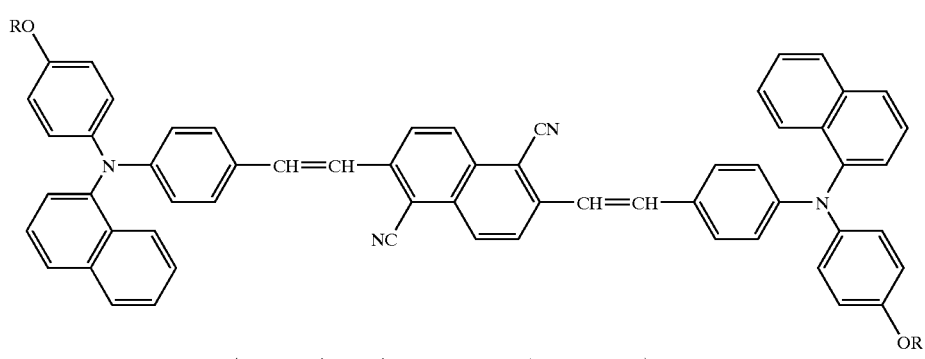
(R = C₂H₅, i-C₃H₇, i-C₄H₉, t-C₄H₉, cyclo-C₆H₁₀, C₆H₅)
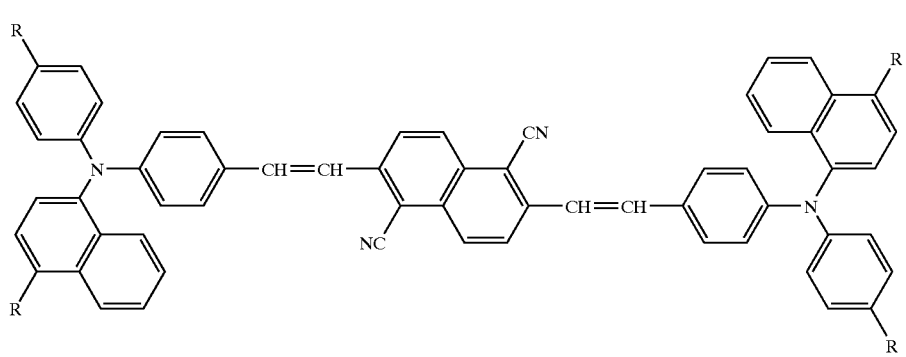
(R = CH₃, C₂H₅, i-C₃H₇, i-C₄H₉, t-C₄H₉, cyclo-C₆H₁₀, C₆H₅)
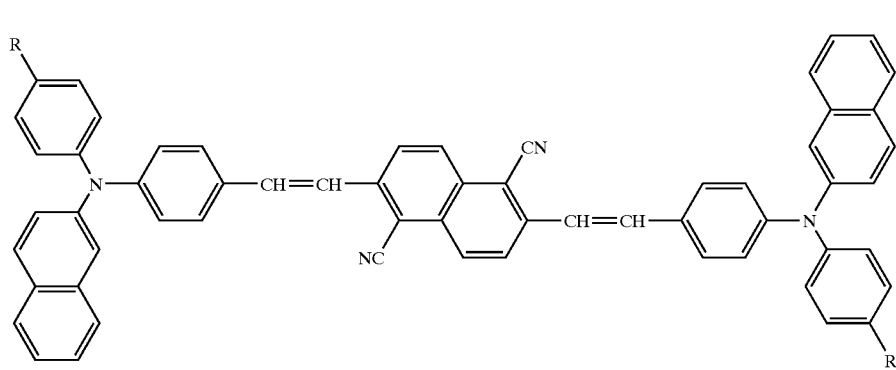
(R = H, CH₃, C₂H₅, i-C₃H₇, i-C₄H₉, t-C₄H₉, cyclo-C₆H₁₀, C₆H₅)

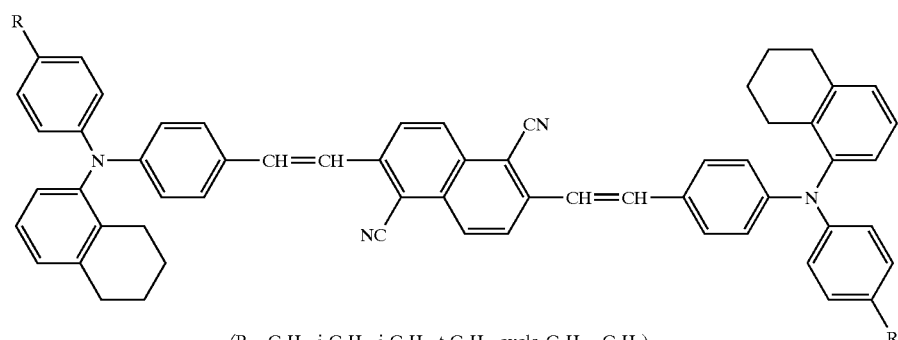
(R = C₂H₅, i-C₃H₇, i-C₄H₉, t-C₄H₉, cyclo-C₆H₁₀, C₆H₅)
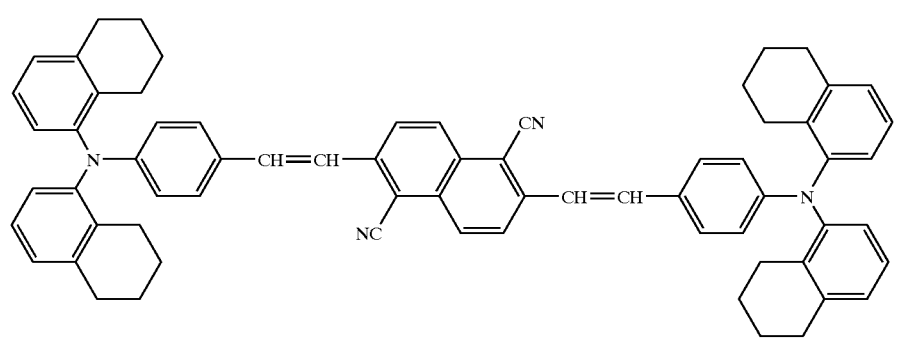
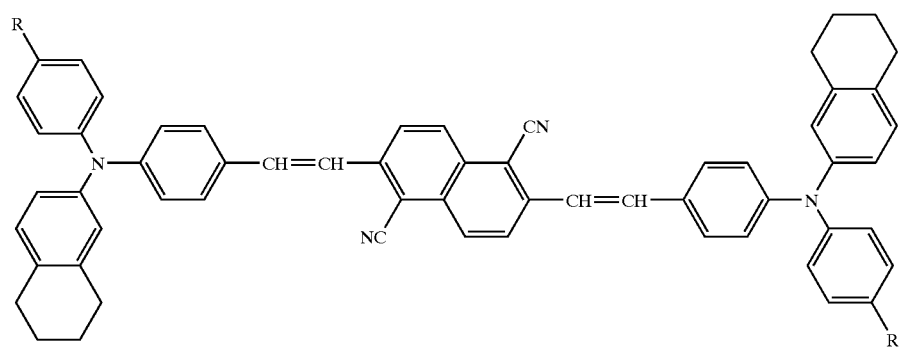
(R = CH₃, C₂H₅, i-C₃H₇, i-C₄H₉, t-C₄H₉, cyclo-C₆H₁₀, C₆H₅)
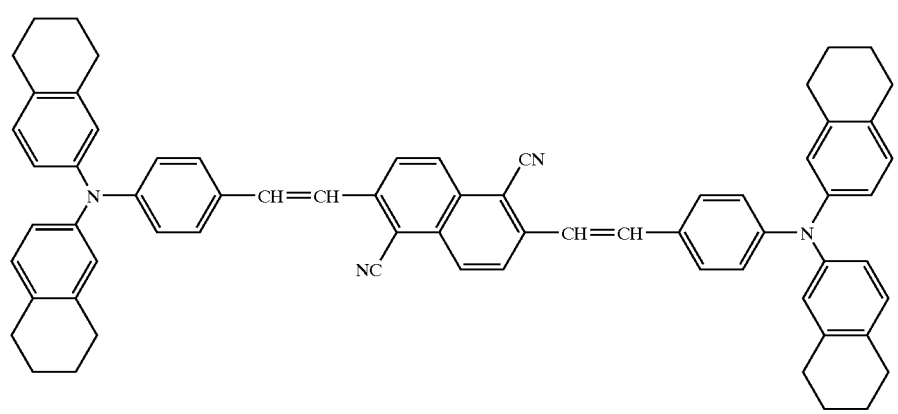

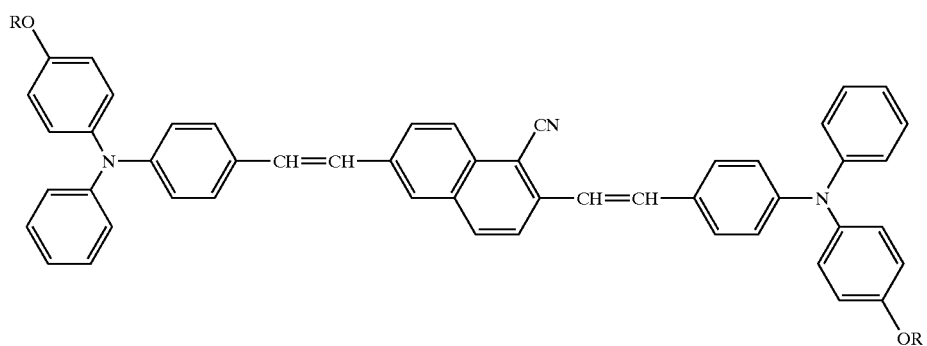
(R = C₂H₅, i-C₃H₇, i-C₄H₉, t-C₄H₉, cyclo-C₆H₁₀, C₆H₅)
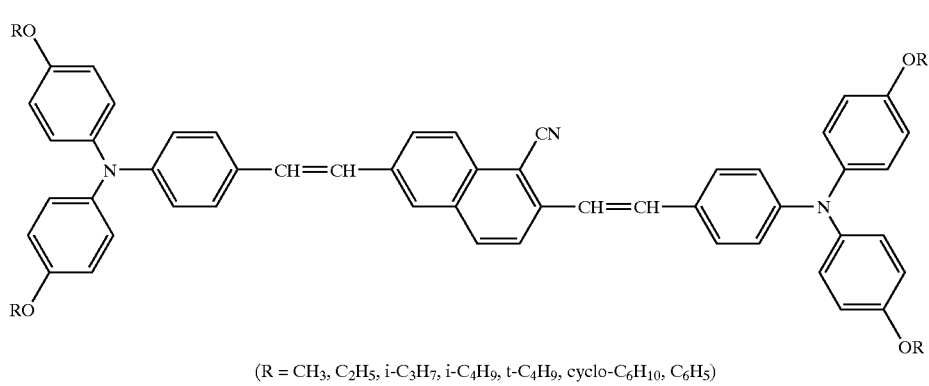
(R = CH₃, C₂H₅, i-C₃H₇, i-C₄H₉, t-C₄H₉, cyclo-C₆H₁₀, C₆H₅)
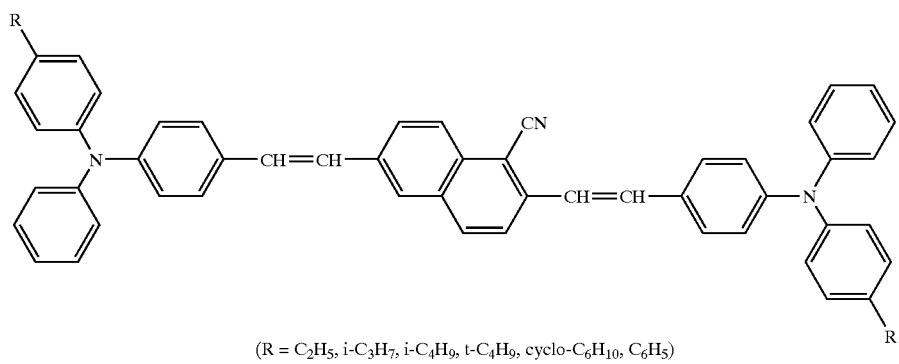
(R = C₂H₅, i-C₃H₇, i-C₄H₉, t-C₄H₉, cyclo-C₆H₁₀, C₆H₅)
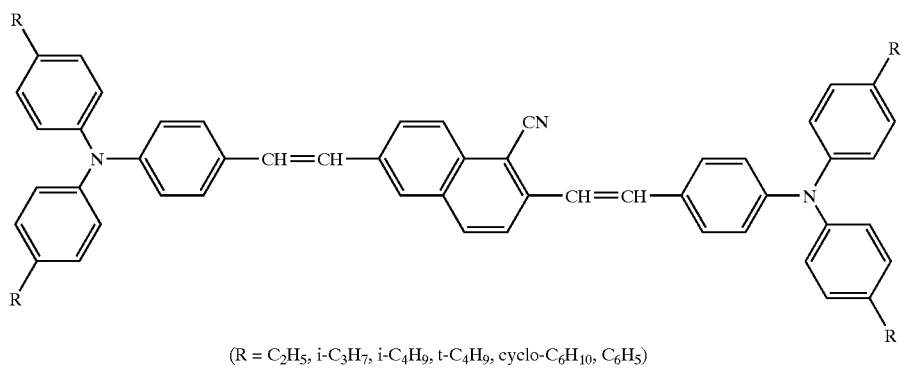
(R = C₂H₅, i-C₃H₇, i-C₄H₉, t-C₄H₉, cyclo-C₆H₁₀, C₆H₅)

-continued
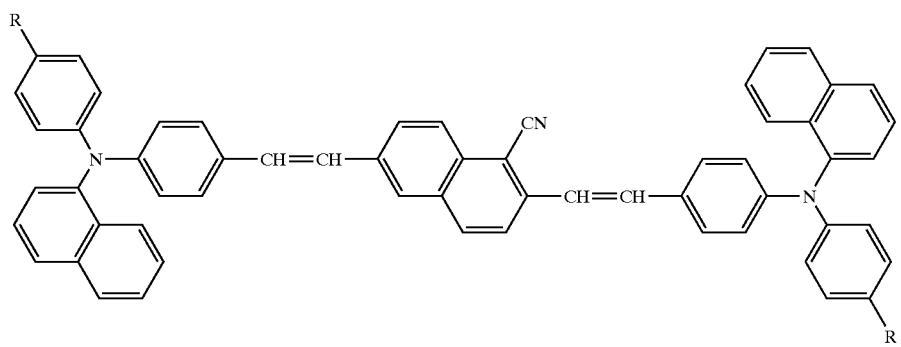
(R = C₂H₅, i-C₃H₇, i-C₄H₉, t-C₄H₉, cyclo-C₆H₁₀, C₆H₅)
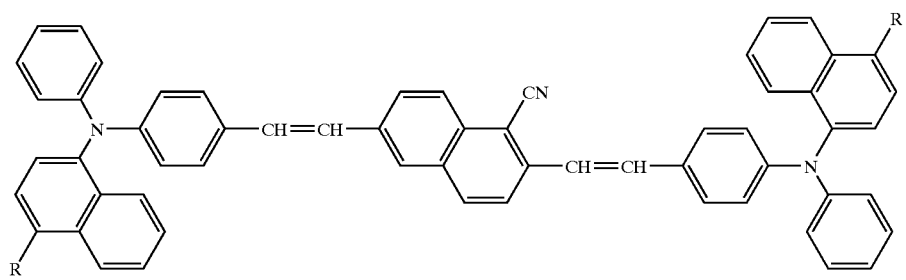
(R = CH₃, C₂H₅, i-C₃H₇, i-C₄H₉, t-C₄H₉, cyclo-C₆H₁₀, C₆H₅)
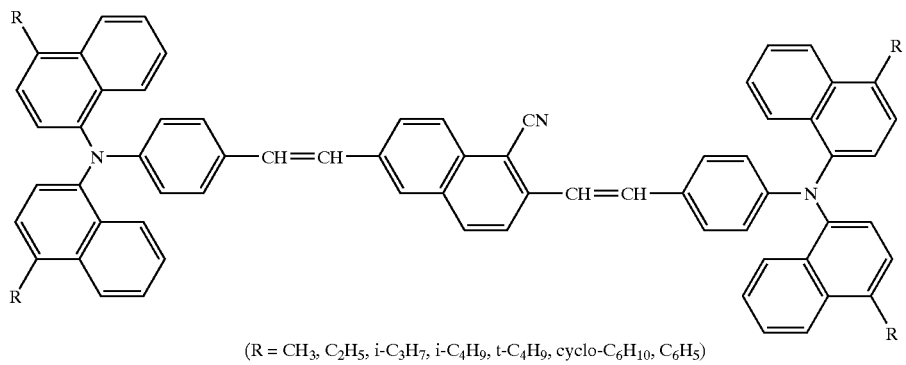
(R = CH₃, C₂H₅, i-C₃H₇, i-C₄H₉, t-C₄H₉, cyclo-C₆H₁₀, C₆H₅)
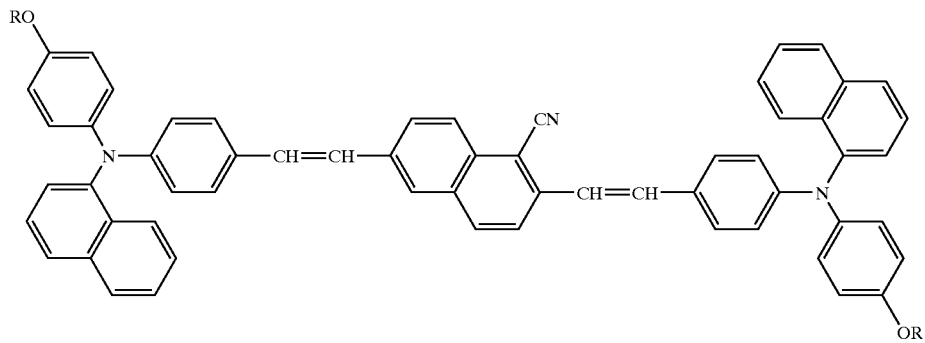

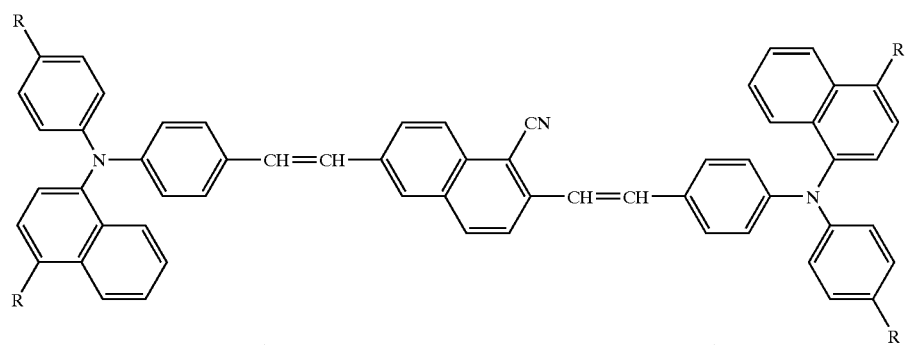
(R = CH₃, C₂H₅, i-C₃H₇, i-C₄H₉, t-C₄H₉, cyclo-C₆H₁₀, C₆H₅)
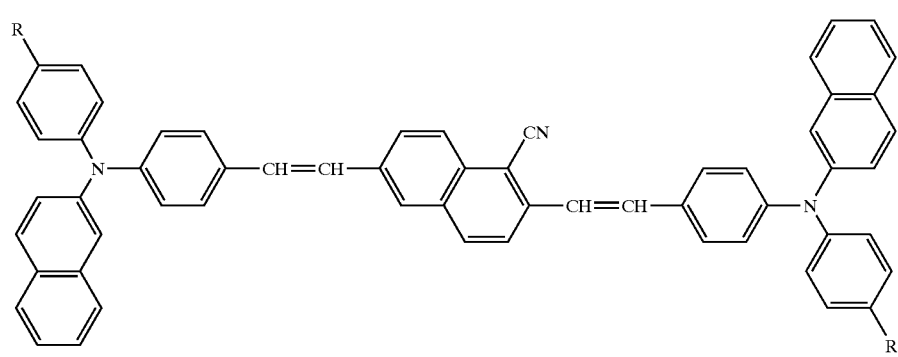
(R = H, CH₃, C₂H₅, i-C₃H₇, i-C₄H₉, t-C₄H₉, cyclo-C₆H₁₀, C₆H₅)
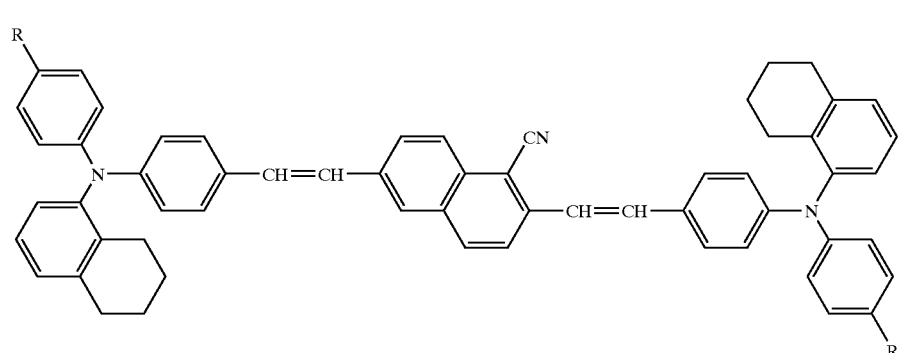
(R = C₂H₅, i-C₃H₇, i-C₄H₉, t-C₄H₉, cyclo-C₆H₁₀, C₆H₅)
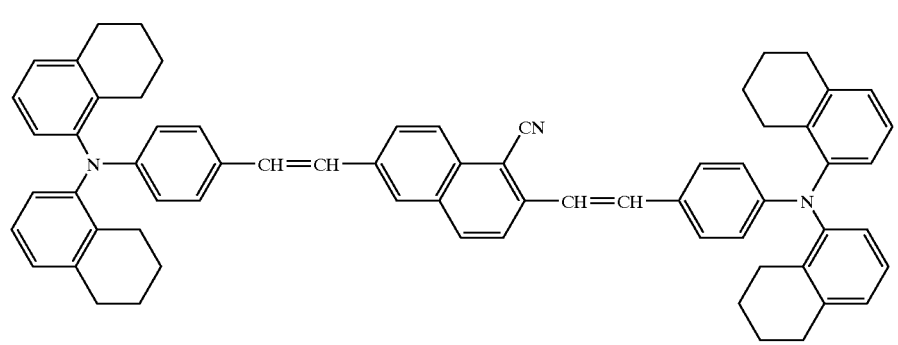

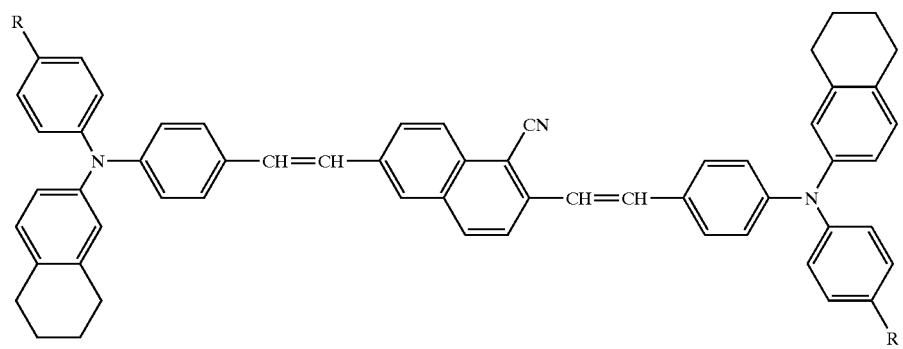
(R = H, CH₃, C₂H₅, i-C₃H₇, i-C₄H₉, t-C₄H₉, cyclo-C₆H₁₀, C₆H₅)
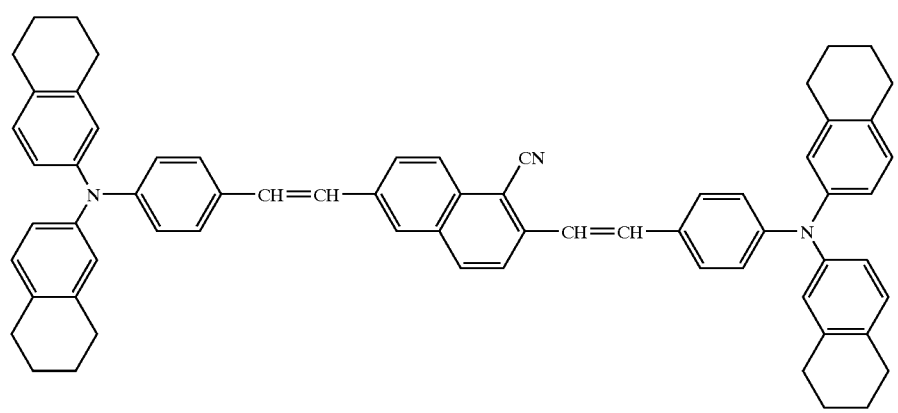
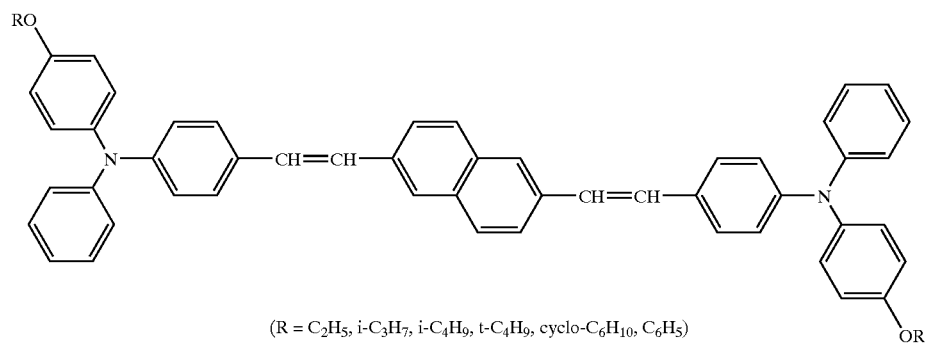
(R = C₂H₅, i-C₃H₇, i-C₄H₉, t-C₄H₉, cyclo-C₆H₁₀, C₆H₅)
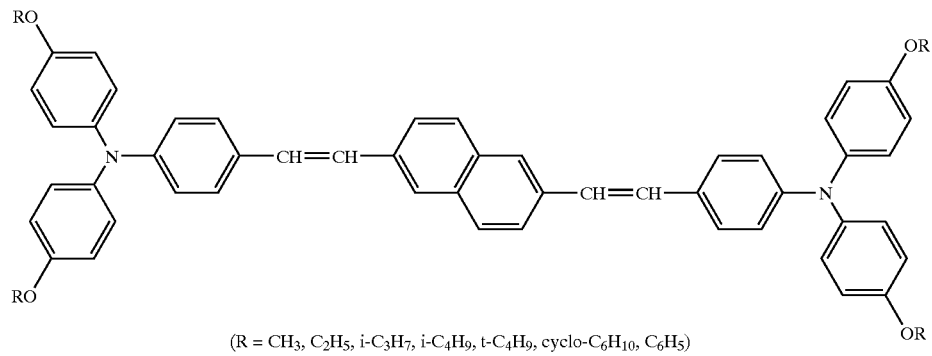
(R = CH₃, C₂H₅, i-C₃H₇, i-C₄H₉, t-C₄H₉, cyclo-C₆H₁₀, C₆H₅)

-continued
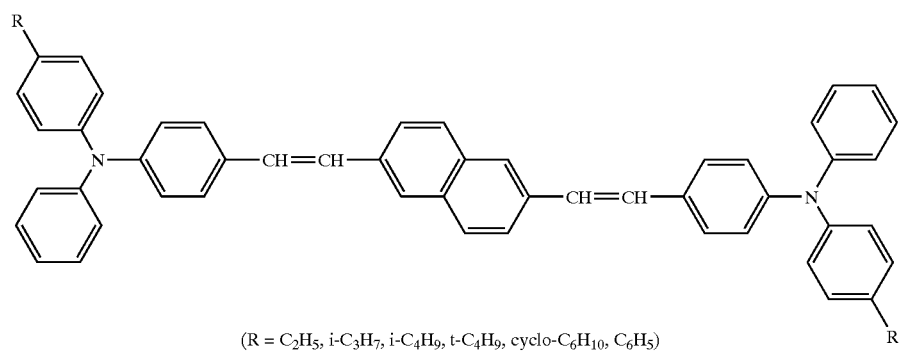
(R = C$_2$H$_5$, i-C$_3$H$_7$, i-C$_4$H$_9$, t-C$_4$H$_9$, cyclo-C$_6$H$_{10}$, C$_6$H$_5$)
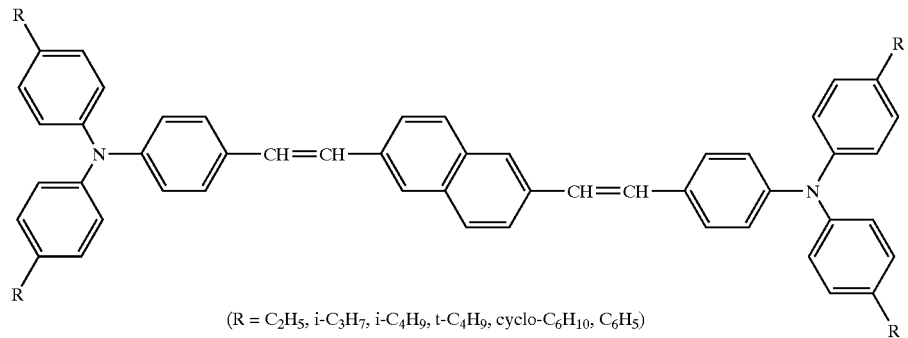
(R = C$_2$H$_5$, i-C$_3$H$_7$, i-C$_4$H$_9$, t-C$_4$H$_9$, cyclo-C$_6$H$_{10}$, C$_6$H$_5$)
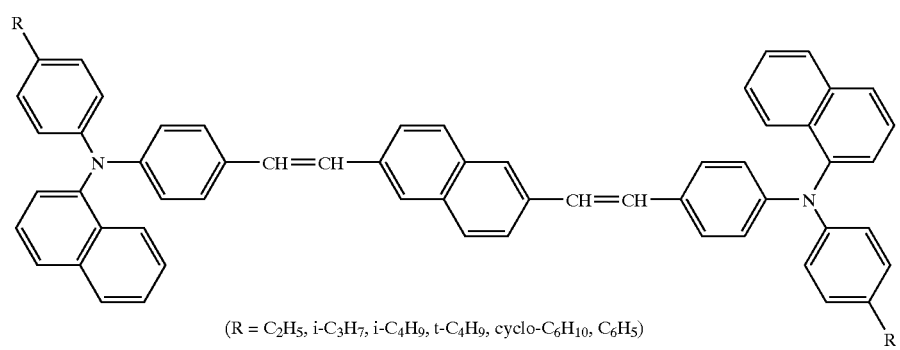
(R = C$_2$H$_5$, i-C$_3$H$_7$, i-C$_4$H$_9$, t-C$_4$H$_9$, cyclo-C$_6$H$_{10}$, C$_6$H$_5$)
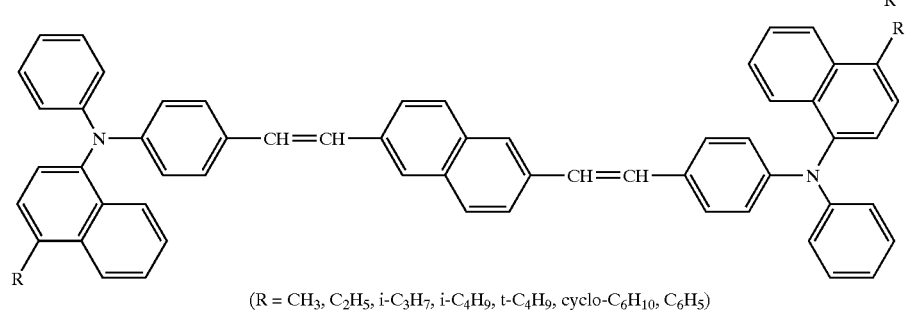
(R = CH$_3$, C$_2$H$_5$, i-C$_3$H$_7$, i-C$_4$H$_9$, t-C$_4$H$_9$, cyclo-C$_6$H$_{10}$, C$_6$H$_5$)
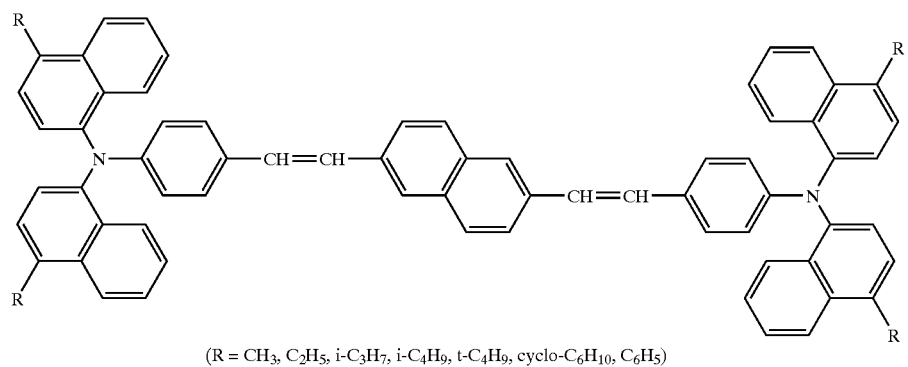
(R = CH$_3$, C$_2$H$_5$, i-C$_3$H$_7$, i-C$_4$H$_9$, t-C$_4$H$_9$, cyclo-C$_6$H$_{10}$, C$_6$H$_5$)

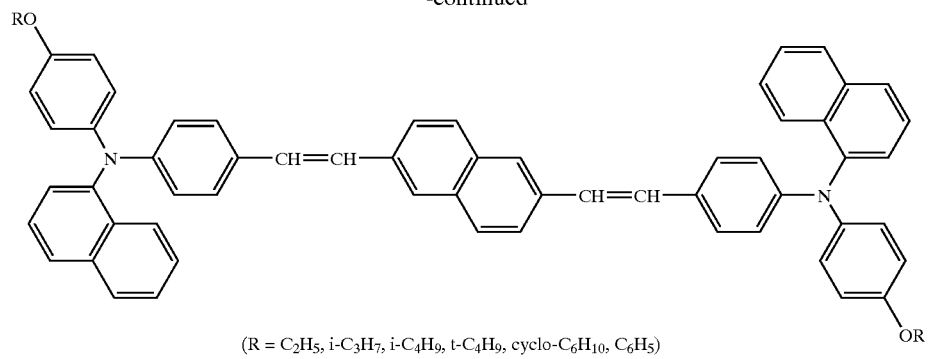
(R = C$_2$H$_5$, i-C$_3$H$_7$, i-C$_4$H$_9$, t-C$_4$H$_9$, cyclo-C$_6$H$_{10}$, C$_6$H$_5$)
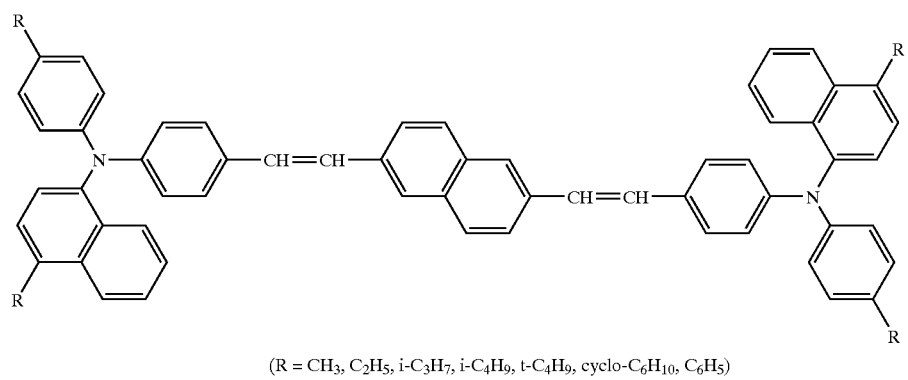
(R = CH$_3$, C$_2$H$_5$, i-C$_3$H$_7$, i-C$_4$H$_9$, t-C$_4$H$_9$, cyclo-C$_6$H$_{10}$, C$_6$H$_5$)
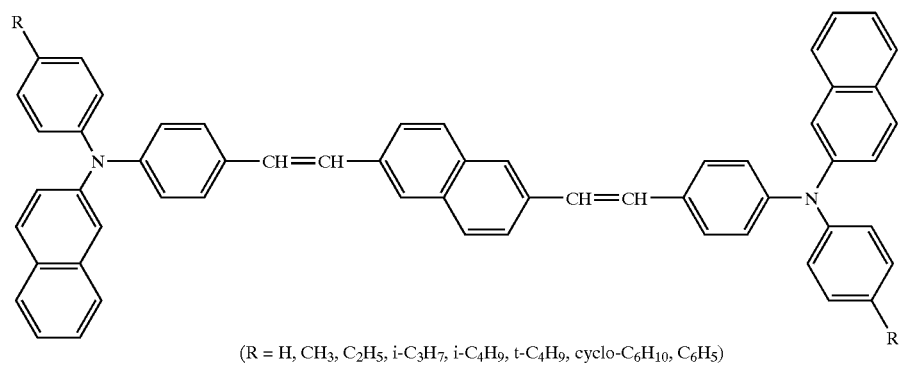
(R = H, CH$_3$, C$_2$H$_5$, i-C$_3$H$_7$, i-C$_4$H$_9$, t-C$_4$H$_9$, cyclo-C$_6$H$_{10}$, C$_6$H$_5$)
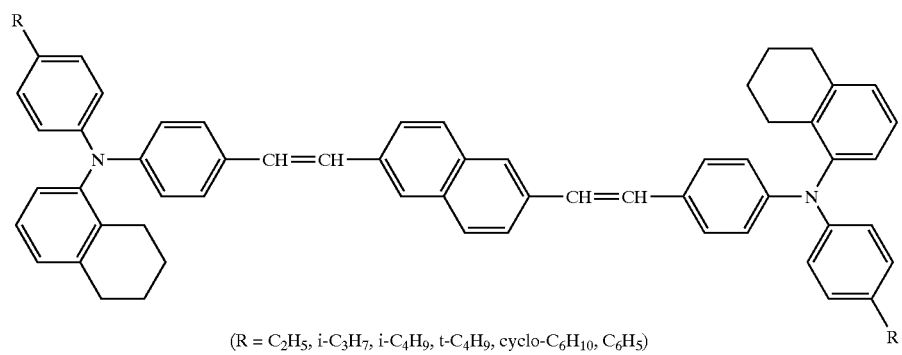
(R = C$_2$H$_5$, i-C$_3$H$_7$, i-C$_4$H$_9$, t-C$_4$H$_9$, cyclo-C$_6$H$_{10}$, C$_6$H$_5$)

-continued

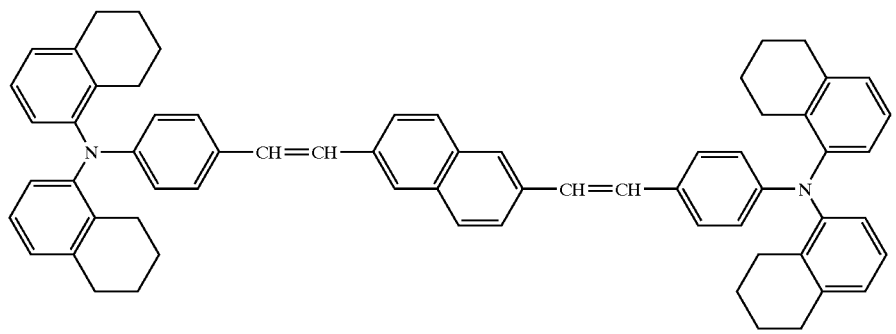

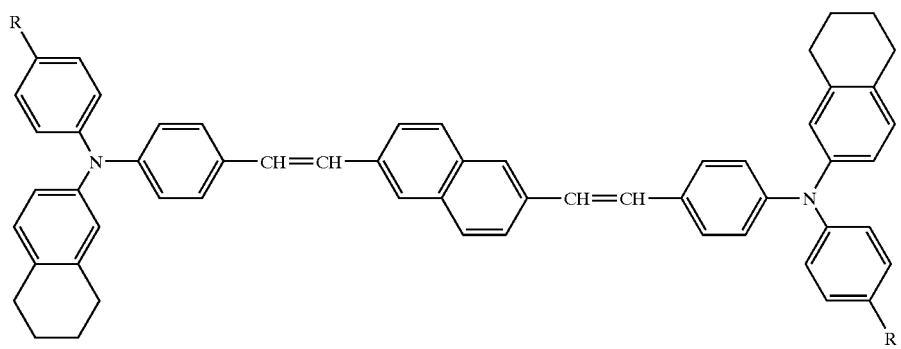

(R = $CH_3$, $C_2H_5$, $i\text{-}C_3H_7$, $i\text{-}C_4H_9$, $t\text{-}C_4H_9$, cyclo-$C_6H_{10}$, $C_6H_5$)

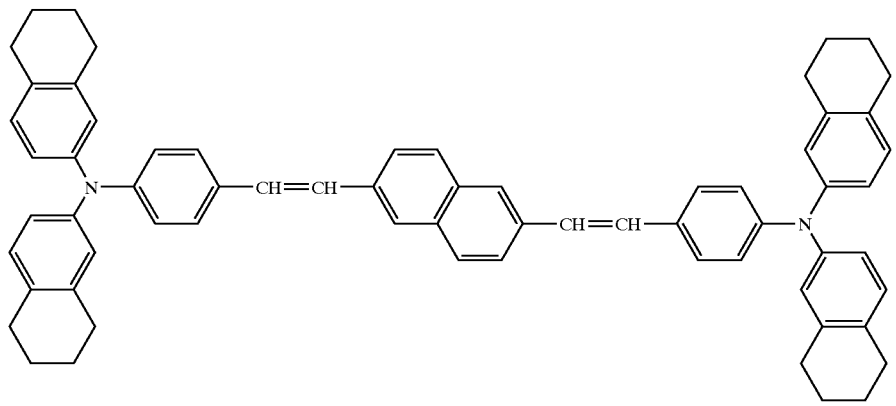

The present invention is directed also to a process for efficiently producing the compound of the present invention. This process yields a bis (aminostyryl)naphthalene compound represented by the general formula [I], [II], [III], or [IV] given above by condensation from at least one species of 4-(N,N-diarylamino)benzaldehyde represented by the general formula [V] or [VI] below and diphosphonic ester represented by the general formula [VII] below or diphosphonium represented by the general formula [VIII] below.

General formula [V]

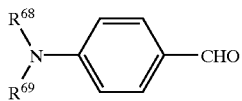

General formula [VI]

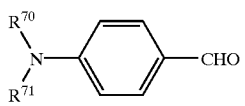

(where $R^{68}$ and $R^{69}$ each denotes an aryl group corresponding to $R^1$, $R^2$, $R^{12}$, $R^{13}$, $R^{23}$, $R^{24}$, $R^{34}$, or $R^{35}$ given above; and $R^{70}$ and $R^{71}$ each denotes an aryl group corresponding to $R^3$, $R^4$, $R^{14}$, $R^{15}$, $R^{25}$, $R^{26}$, $R^{36}$, or $R^{37}$ given above.)

General formula [VII]

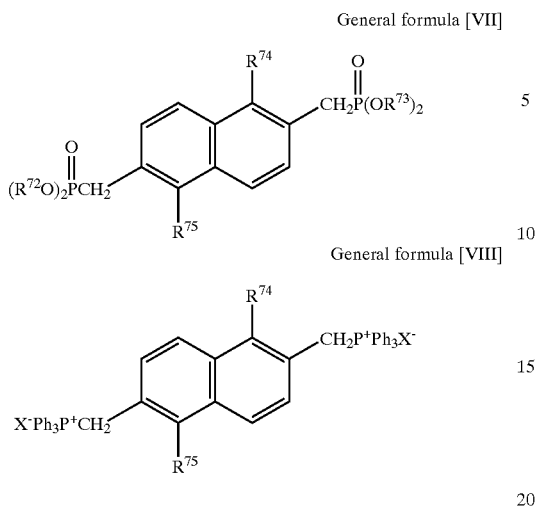

General formula [VIII]

General formula (39)

General formula (40)

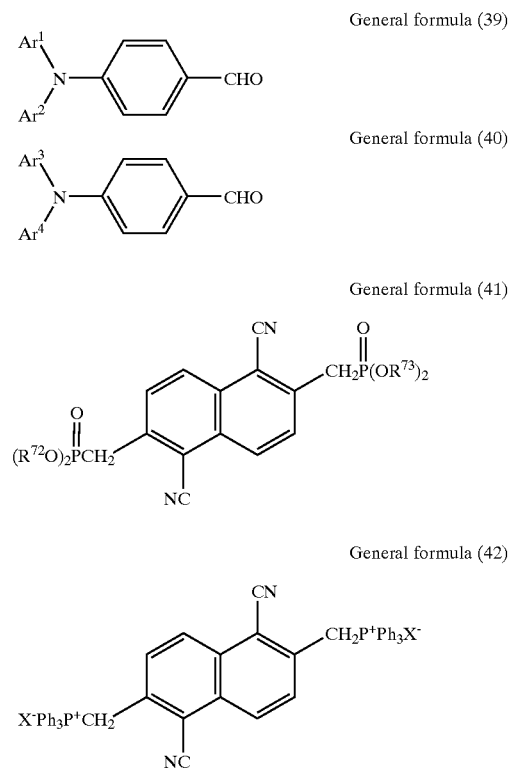

General formula (41)

General formula (42)

(where $R^{72}$ and $R^{73}$ are identical or different, each denoting a hydrocarbon group (preferably saturated hydrocarbon group having 1 to 6 carbon atoms, the same shall apply hereinafter); $R^{74}$ and $R^{75}$ each denotes a group corresponding to $R^5$, $R^6$, $R^{16}$, $R^{17}$, $R^{27}$, $R^{28}$, $R^{38}$, or $R^{39}$ given above; and X denotes a halogen atom.)

The process for producing the compound of the present invention consists of treating the diphosphonic ester and/or diphosphonium with a base in a solvent, thereby giving carboanion, and condensing this carboanion with the 4-(N,N-diarylamino)benzaldehyde by Wittig-Horner reaction or Wittig reaction.

For example, a bis(aminostyryl)naphthalene compound represented by the general formula (6) below (where $Ar^1$, $Ar^2$, $Ar^3$, $Ar^4$, $R^{72}$, $R^{73}$ and X are defined as above.)

General formula (6)

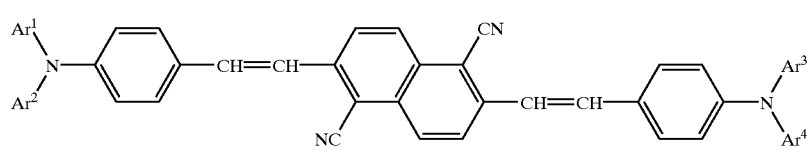

(where $Ar^1$, $Ar^2$, $Ar^3$, and $Ar^4$ are defined as above.) is produced by condensing at least one species of 4-(N,N-diarylamino)benzaldehyde represented by the general formula (39) or (40) below with diphosphonic ester represented by the general formula (41) below or diphosphonium represented by the general formula (42) below.

This reaction may be shown by the following reaction scheme 1.

Reaction scheme 1:

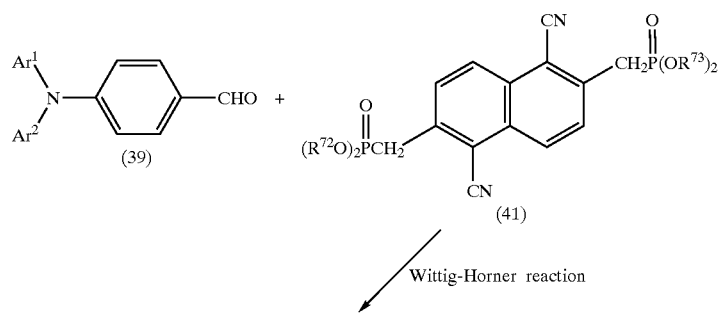

Wittig-Horner reaction

-continued

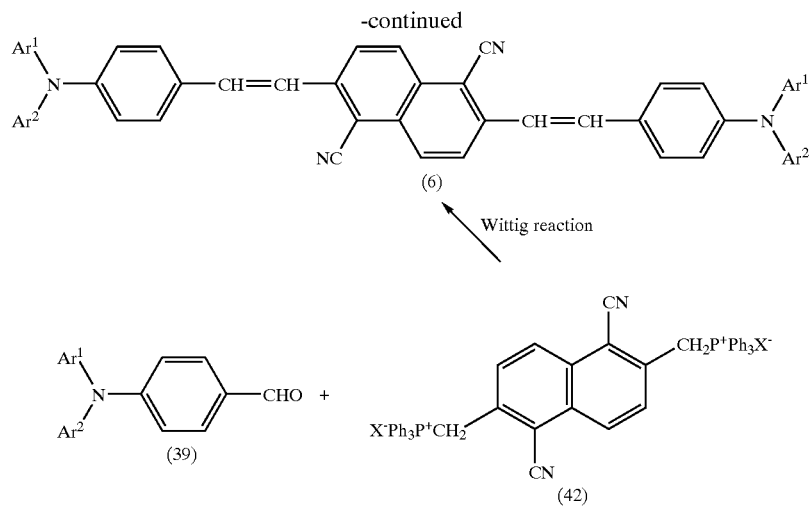

(6)

↖ Wittig reaction

(39) + (42)

This reaction is started by treating the compound of the general formula (41) or (42) with a base in a solvent, thereby giving carboanion, and is completed by condensing this carboanion with the aldehyde of the general formula (39). Possible combinations of a base and a solvent are as follows.

Sodium hydroxide/water, sodium carbonate/water, potassium carbonate/water, sodium ethoxide/ethanol or dimethylformamide, sodium methoxide/methanol-diethyl ether mixed solvent or dimethylformamide, triethylamine/ethanol or diglyme or chloroform or nitromethane, pyridine/methylene chloride or nitromethane, 1,5-diazabicyclo[4.3.0] non-5-ene/dimethylsulfoxide, potassium t-butoxide/dimethylsulfoxide or tetrahydrofuran or benzene or dimethylformamide, phenyl lithium/diethyl ether or tetrahydrofuran, t-butyl lithium/diethyl ether or tetrahydrofuran, sodium amide/ammonium, sodium hydride/dimethylformamide or tetrahydrofuran, trimethyl sodium/diethyl ether or tetrahydrofuran, etc.

This reaction proceeds at a comparatively low temperature (−30° C. to 30° C.) and proceeds selectively. Therefore, the desired product can be purified easily by chromatography. In addition, the compound of the present invention represented by the general formula (6) is highly crystalline and hence it can be purified easily by recrystallization. The method of recrystallization is not specifically restricted. A simple way is by dissolution in acetone and subsequent addition of hexane, or by dissolution in toluene with heating and subsequent concentration and cooling. This reaction may be carried out under normal pressure for 3–24 hours.

The process of the present invention yields a bis-(aminostyryl)naphthalene compound represented by the general formula (13), (13'), (14), (15), (16), (17), (18), (18'), (19), (21), (22), (23), (24), (25), (26), (27), (27'), (28), (30), (31), (32), (33), (34), (35), (36), (36'), or (37) given above. To be more specific, the process of the present invention yields a bis(amino-styryl)naphthalene compound represented by the structural formula (20)-1, (20)-2, (20)-3, (20)-4, (20)-5, (20)-6, (20)-7, (20)-8, (20)-9, (20)-10, (20)-11, (20)-12, (20)-12', (20)-13, (20)-14, (20)-15, (29)-1, (29)-2, (29)-3, (29)-4, (29)-5, (29)-6, (29)-7, (29)-8, (29)-9, (29)-10, (29)-11, (29)-12, (29)-12', (29)-13, (29)-14, (29)-15, (38)-1, (38)-2, (38)-3, (38)-4, (38)-5, (38)-6, (38)-7, (38)-8, (38)-9, (38)-10, (38)-11, (38)-12, (38)-12', (38)-13, or (38)-14 given above.

The present invention also provides a variety of compounds suitable as intermediates for synthesis of the compound of the present invention.

The intermediate is diphosphonic ester represented by the general formula [VII] above or diphosphonium represented by the general formula [VIII] above. It is used for synthesis of a bis(aminostyryl)naphthalene compound represented by the general formula [II], [II], [III], or [IV] above.

To be concrete, this synthesis intermediate (referred to as the synthesis intermediate 1 of the present invention) is represented by the general formula (41), (42), (43), (44), (45), or (46) below.

General formula (41)

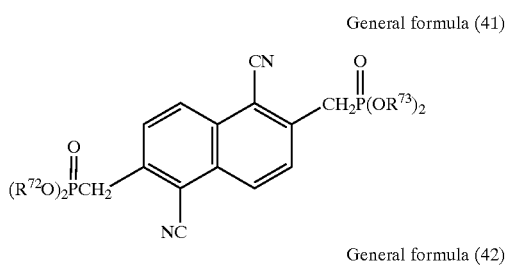

General formula (42)

General formula (43)

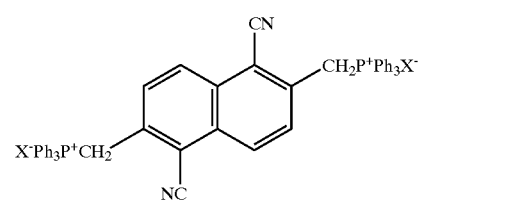

General formula (44)

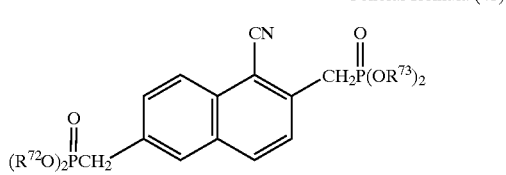

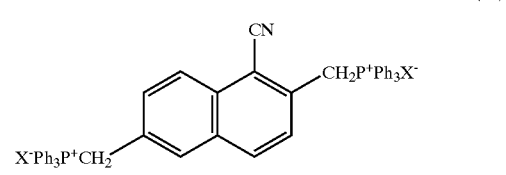

General formula (45)

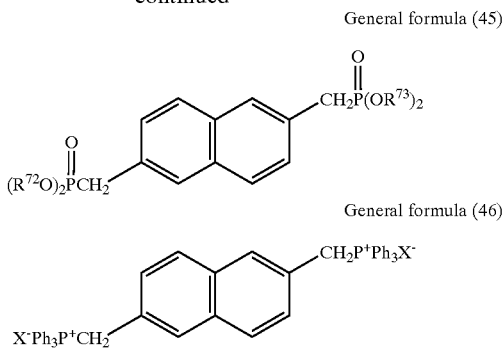

General formula (46)

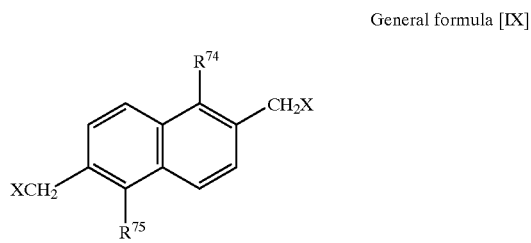

(where $R^{72}$, $R^{73}$, and X are defined as above.)

The synthesis intermediate 1 of the present invention may be derived from its precursor as follows.

That is, reaction between an aryl halide compound represented by the general formula [IX] and a trialkyl phosphite represented by the general formula [X] or triphenyl phosphine (PPh₃) yields diphosphonic ester represented by the general formula [VII] above or diphosphonium represented by the general formula [VIII] above as the synthesis intermediate. This reaction may be carried out without solvent or in a solvent (such as xylene) having a boiling point higher than 120° C. This reaction may also be carried out in a large excess of trialkyl phosphite under normal pressure at 120–160° C. for 30 minutes to 24 hours.

General formula [IX]

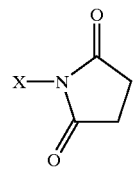

(where $R^{74}$ and $R^{75}$ are identical or different, at least one of them denoting a hydrogen atom, cyano group, nitro group, trifluoromethyl group, or halogen atom, and X denotes a halogen atom.)

General Formula [X]

$P(OR^{76})_3$ or $P(OR^{77})_3$ (where $R^{76}$ and $R^{77}$ are identical or different, each denoting a hydrocarbon group, particularly a saturated or unsaturated hydrocarbon group having 1 to 4 carbon atoms.)

The present invention also provides an aryl halide compound (referred to as the synthesis intermediate 2 of the present invention) represented by the general formula [IX] above, which is used as a synthesis intermediate to give the synthesis intermediate 1 of the present invention.

The synthesis intermediate 2 of the present invention can be obtained by reaction with irradiation between a dimethylnaphthalene compound represented by the general formula [XI] below and an N-halogenated succinimide represented by the general formula [XII] below. This reaction is carried out in a solvent such as carbon tetrachloride, chloroform, benzene, and chlorobenzene. The light source for irradiation includes a high-pressure mercury lamp, low-pressure mercury lamp, xenon lamp, halogen lamp, sun light, and fluorescent lamp. The reaction may be carried out under normal pressure at 20–120° C. for 30 minutes to 48 hours.

General formula [XI]

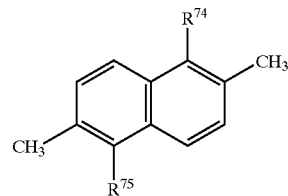

(where $R^{74}$ and $R^{75}$ are identical or different, at least one of them denoting a hydrogen atom, cyano group, nitro group, trifluoromethyl group, or halogen atom.)

General formula [XII]

(where X denotes a halogen atom.]

The above-mentioned reaction to give the synthesis intermediates 1 and 2 may be represented by the reaction scheme 2 as follows.

Reaction scheme 2:

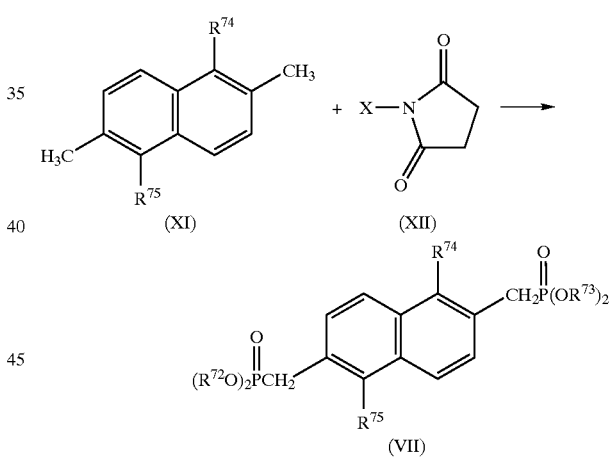

FIGS. 6 to 9 show some examples of the organic electroluminescent element (EL element) which employs the compound of the present invention as an organic luminescent material.

Figure 6:
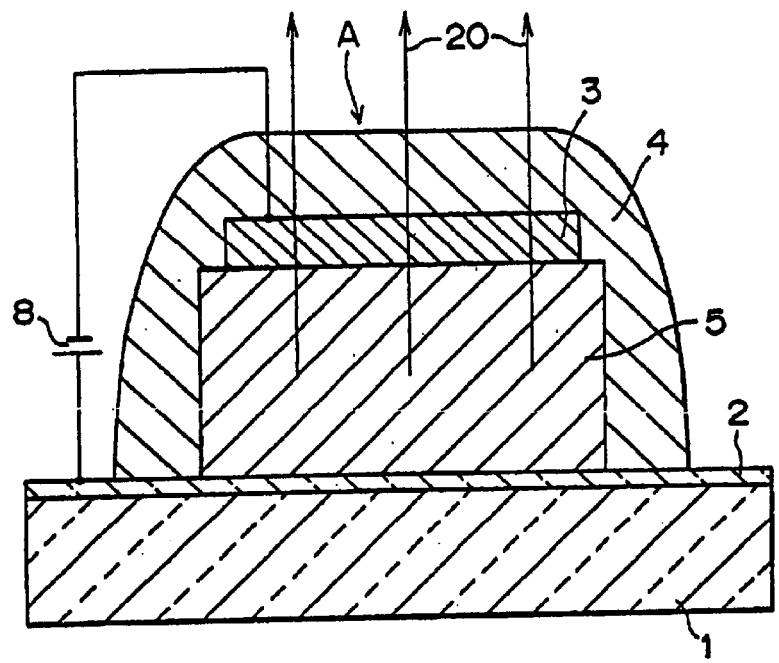
FIG. 6 is a schematic sectional view showing an important part of an organic electroluminescent element according to the present invention.
Figure 7:
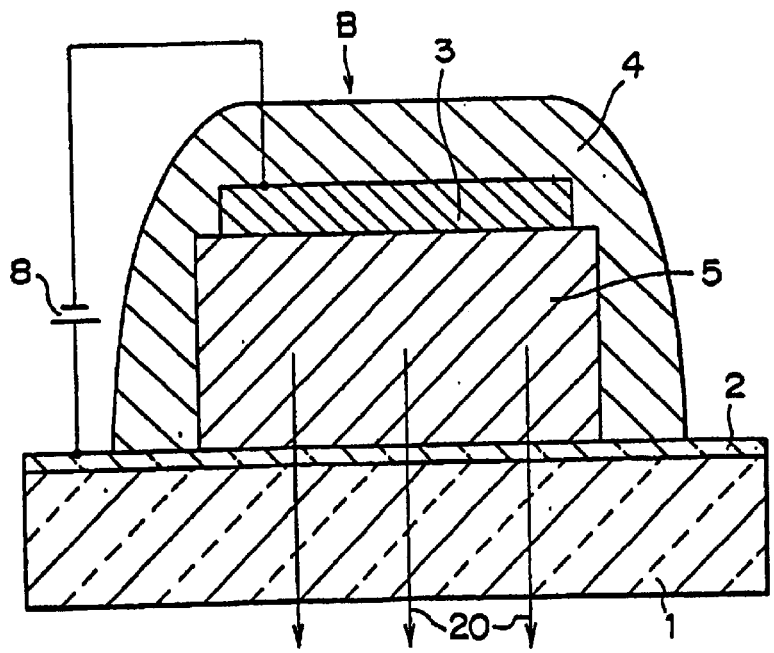
FIG. 7 is a schematic sectional view showing an important part of another organic electroluminescent element according to the present invention.

FIG. 6 shows an organic electroluminescent element A of transmission type which is designed such that the cathode 3 transmits the emitted light 20 or the emitted light 20 is visible through the protective film 4. FIG. 7 shows an organic electroluminescent element B which is designed such that the cathode 3 reflects the emitted light 20.

In FIGS. 6 and 7, the reference number 1 indicates a substrate on which is formed the organic electroluminescent element. The substrate may be formed from glass, plastics, and any other adequate material. In the case where the organic electroluminescent element is used in combination with other display element, a single substrate may be used in common for both of them. The reference number 2 denotes a transparent electrode (anode), which is made from ITO (indium tin oxide) or $SnO_2$.

The reference number 5 denotes an organic luminescent layer which contains the compound of the present invention as the luminescent material. The luminescent layer may have any known layer structure for obtaining the emitted light 20. For example, it may be formed from thin films of hole transfer layer and electron transfer layer. One or both of these layers may be combined with other thin films or mixed with other materials so as to improve the charge transfer performance. In addition, in order to improve the light-emitting performance, a thin film made of one or more fluorescent materials may be interposed between the hole transfer layer and the electron transfer layer. Alternatively, one or more fluorescent materials may be incorporated into the hole transfer layer or the electron transfer layer or both. In this case, the layer structure may include a thin film to control the hole transfer or electron transfer so as to improve the light-emitting efficiency.

If the compound of the present invention has both functions of electron transfer and hole transfer, then it may be used as the light-emitting layer which also functions as the electron transfer layer or it may be used as the light emitting-layer which also functions as the hole transfer layer. Another possible structure is such that the compound of the present invention constitutes the light-emitting layer which is interposed between the electron transfer layer and the hole transfer layer.

Incidentally, the reference number 3 in FIGS. 6 and 7 indicates a cathode, which is made of an active metal (such as Li, Mg, and Ca) and a metal (such as Ag, Al, and In) in the form of alloy or laminate. In the case of an organic electroluminescent element of transmission type, the cathode thickness may be properly adjusted so that the cathode has an adequate light transmittance suitable for individual applications. The reference number 4 in FIGS. 6 and 7 indicates a sealing/protective layer which entirely covers the organic electroluminescent element for the maximal effect. An adequate material may be used to ensure hermitic sealing. The reference number 8 denotes a power supply to drive the element.

The organic luminescent element mentioned above has an organic layer in which the hole transfer layer and the electron transfer layer are laminated on top of the other. In other words, it has the single-hetero structure. The hole transfer layer or the electron transfer layer may be formed from the compound of the present invention. Alternatively, the organic layer may have the double-hetero structure in which the hole transfer layer, the luminescent layer, and the electron transfer layer are laminated sequentially. In this case, the luminescent layer may be formed from the compound of the present invention.

Figure 8:
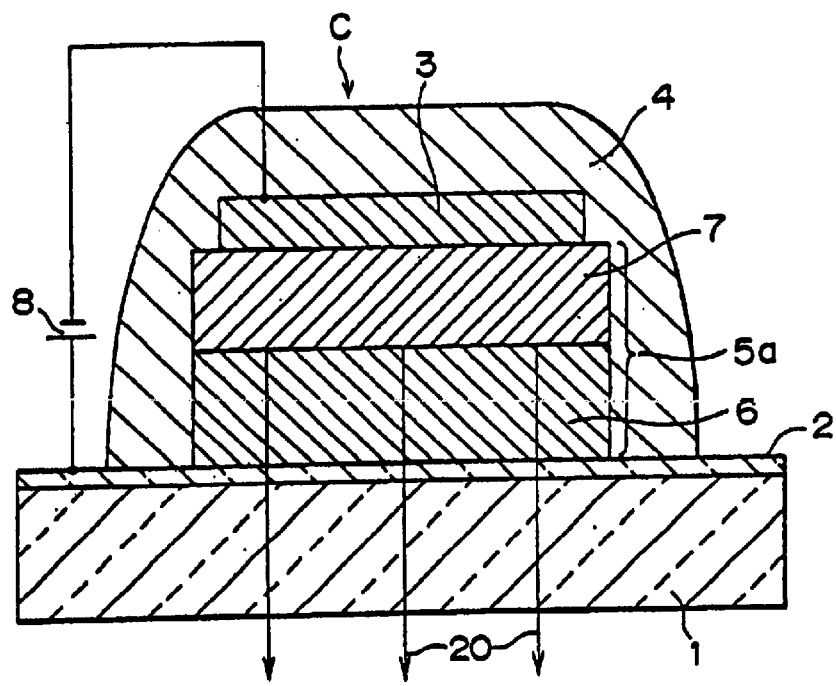
FIG. 8 is a schematic sectional view showing an important part of another organic electroluminescent element according to the present invention.

FIG. 8 shows an organic electroluminescent element C of single-hetero structure (organic laminate structure). This organic electroluminescent element is composed of a transparent substrate 1, a transparent anode 2, an organic layer 5a (consisting of a hole transfer layer 6 and an electron transfer layer 7), and a cathode 3, which are sequentially laminated one over another. The layer structure is sealed with a protective film 4.

The layer structure shown in FIG. 8 has no luminescent element. In this case, light 20 of desired wavelength is emitted from the interface between the hole transfer layer 6 and the electron transfer layer 7. The emitted light is visible through the substrate 1.

Figure 9:
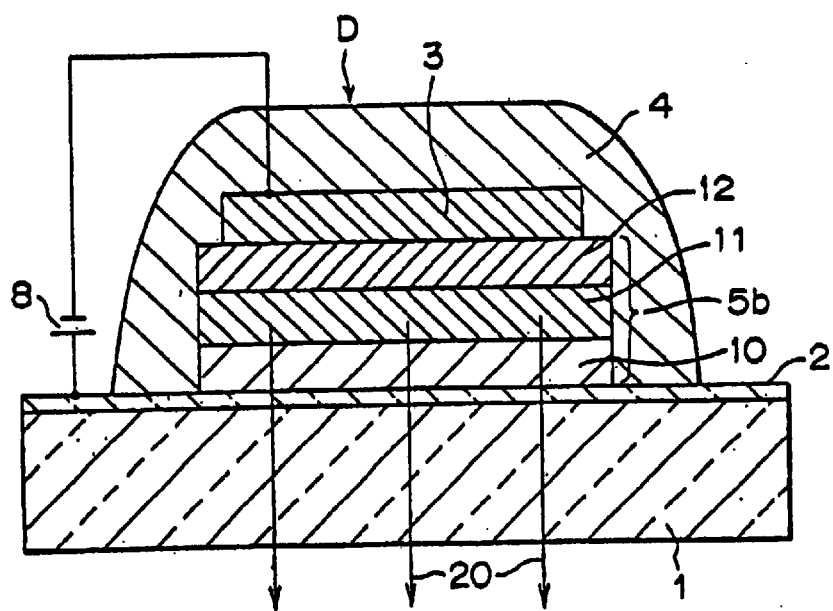
FIG. 9 is a schematic sectional view showing an important part of another organic electroluminescent element according to the present invention.

FIG. 9 shows an organic electroluminescent element D of double-hetero structure. This organic electroluminescent element is composed of a transparent substrate 1, a transparent anode 2, an organic layer 5b (consisting of a hole transfer layer 10, a luminescent layer 11, and an electron transfer layer 12), and a cathode 3, which are sequentially laminated one over another. The layer structure is sealed with a protective film 4.

The organic electroluminescent element shown in FIG. 9 is given dc current applied across the anode 2 and the cathode 3. This dc current causes anode 2 to inject holes and the cathode 3 to inject electrons. The injected holes reach the luminescent layer 11 through the hole transfer layer 10 and the injected electrons reach the luminescent layer 11 through the electron transfer layer 12. The electron/hole recombination takes place in the luminescent layer 11, thereby giving rise to singlet excitons which emit the light of desired wavelength.

In the above-mentioned organic electroluminescent elements C and D, the substrate 1 may be formed from any transparent material such as glass and plastics. This substrate may serve for another display element combined with the electroluminescent element. This substrate may also serve for the electroluminescent elements of laminate structure (as shown in FIGS. 8 and 9) which are arranged in array. The elements C and D may be of transmission type or reflection type.

The anode 2 is a transparent electrode made of ITO (indium tin oxide) or $SnO_2$. Adjoining the anode 2 is the hole transfer layer 6 (or 10). There may be interposed between them a thin film of organic compound or organo-metallic compound for improvement in charge injection efficiency. In the case where the protective film 4 is made of electrically-conductive material (such as metal), the anode 2 may have an insulating layer on its sides.

The organic electroluminescent element C has an organic layer 5a of laminate structure which is composed of a hole transfer layer 6 and an electron transfer layer 7. Either or both of these layers contain the compound of the present invention mentioned above so that they emit light. The organic electroluminescent element D has an organic layer 5b of laminate structure which is composed of a hole transfer layer 10, a light-emitting layer 11 (containing the compound of the present invention), and an electron transfer layer 12. The laminate structure may be modified variously. For example, either or both of the hole transfer layer and the electron transfer layer may possess the light-emitting layer.

It is desirable that the hole transfer layer 6 or the electron transfer layer 7 or the light-emitting layer 11 is made entirely of the compound of the present invention. Alternatively, they may be formed from the compound of the present invention and a hole or electron transfer material (such as aromatic amine and pyrazoline) which undergo vapor deposition simultaneously. The hole transfer layer may be composed of several hole transfer layers of different kind so that it has improved hole transfer performance.

The organic electroluminescent element C permits the electron transfer layer 7 to emit light; however, it may also permit the hole transfer layer 6 (or its interface) to emit light depending on the voltage applied by the power supply 8.

Likewise, the organic electroluminescent element D permits the electron transfer layer 12 or the hole transfer layer 10 as well as the light-emitting layer 11 to emit light. For their improved light-emitting performance, these electroluminescent elements should preferably be of such structure that the light-emitting layer 11 (which contains at least one kind of fluorescent material) is interposed between the hole transfer layer 10 and the electron transfer layer 12. Alternatively, they may be of such structure that the fluorescent material is contained in the hole transfer layer or the electron transfer layer or both. For improved light-emitting efficiency in these cases, the electroluminescent element may have a thin layer (hole blocking layer or exciton generating layer) to control the transfer of holes or electrons.

The cathode 3 may be formed from an alloy of active metal (such as Li, Mg, and Ca) and metal (such as Ag, Al, and In). Alternatively, it may be a laminate of these metals in the form of thin film. The cathode may vary in thickness and material according to the intended use of the electroluminescent element.

The protective layer 4 functions as a sealing film. It should entirely cover the organic electroluminescent element for improvement in electron injection efficiency and light-emitting efficiency. It may be formed from any material (such as aluminum, gold, and chromium in the form of metal or alloy) so long as it provides hermetic seal.

The above-mentioned organic electroluminescent elements are usually given direct current. However, they may also be given pulsating current or alternating current. The magnitude of current and voltage is not specifically restricted so long as it is not large enough to destroy the element. Efficient light emission with minimal electric energy is desirable in view of the power consumption and life of the organic electroluminescent elements.

Figure 10:
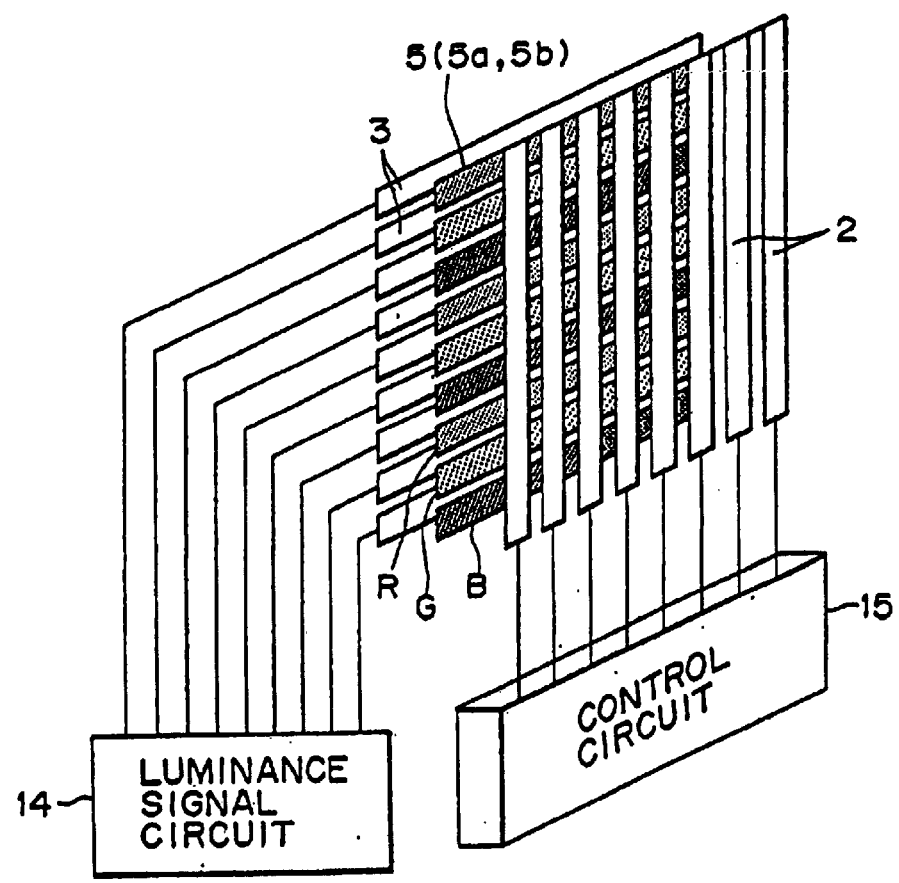
FIG. 10 is a diagram showing a flat display of multicolor or full color type which employs the organic electroluminescent element according to the present invention.

FIG. 10 is a schematic diagram showing the structure of a flat display composed of the organic electroluminescent elements. In the case of full-color display, there is interposed between the cathode 3 and the anode 2 an organic layer 5 (5a, 5b) which emits thee primary colors—red (R), green (G), and blue (B). The cathodes 3 and the anodes 2 are arranged at right angles each other. They are connected to the luminance signal circuit 14 and the control circuit 15 containing shift registers, so that they select a specific pixel at the intersection of the cathode 3 and the anode 2 and apply a signal voltage to it to make the organic layer to emit light.

The display shown in FIG. 10 is that of simple matrix type (8×3 RGB). It has a laminate 5 interposed between the cathode 3 and the anode 2. This laminate is composed of at least one of the hole transfer layer, light-emitting layer, and electron transfer layer. (See FIGS. 8 and 9.) The cathodes and anodes are patterned in strips and crossed each other at right angles so that they form a matrix. They are given signal voltage sequentially by the control circuits 15 and 14 containing shift registers so that they emit light at their intersection. EL elements constructed in this way can be used as a display for characters and codes. They can also be used as an image-reproducing unit. In addition, they may form a solid-state multicolor or full-color flat panel display if each pattern consisting of cathodes and anodes is arranged individually for red, green, and blue colors.

The invention will be described in more detail with reference to the following examples, which are not intended to restrict the scope thereof.

EXAMPLE 1

(Synthesis of bis(aminostyryl)naphthalene Compound Represented by the Structural Formula (20)-2)

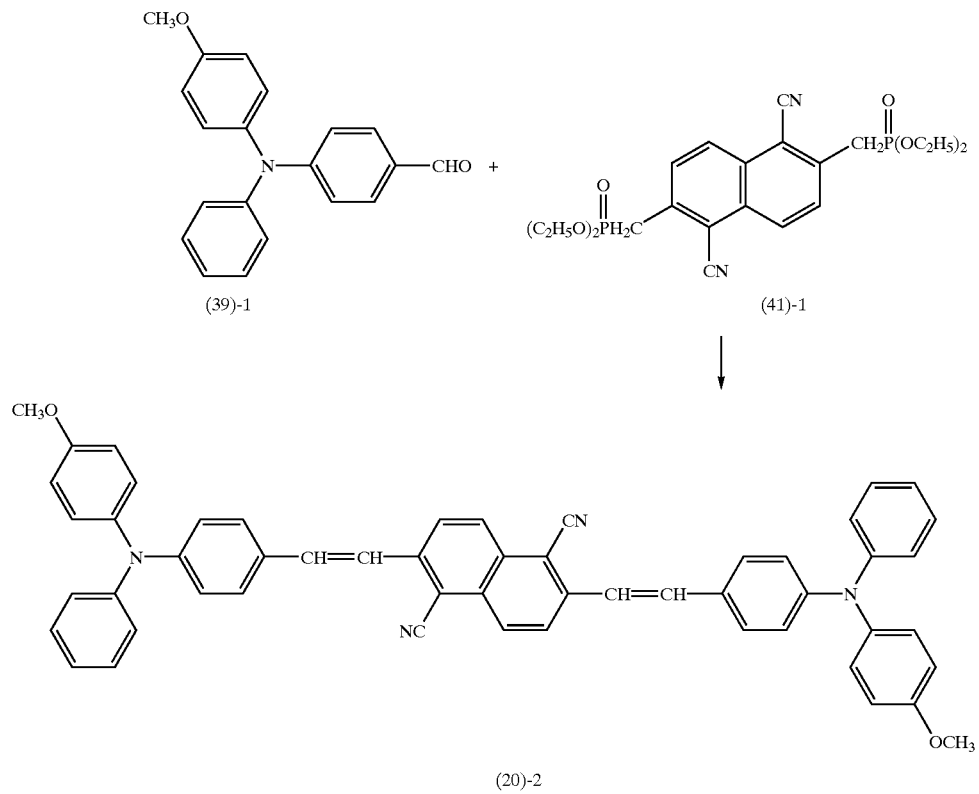

(20)-2

In a reactor was placed 10.2 mmol of sodium hydride (in mineral oil). It was suspended in 10 mL of anhydrous tetrahydrofuran (THF) under a nitrogen atmosphere. With stirring at room temperature, the reactor was given dropwise 80 mL of solution containing 1.72 mmol of diphosphonic ester (represented by the structural formula (41)-1) in 1:1 mixed solvent of anhydrous tetrahydrofuran and anhydrous dimethylformamide (DMF). The reactor was further given 30 mL of solution containing 1.27 g (4.19 mmol) of 4-[N-phenyl-N-(4-methoxyphenyl)amino]benzaldehyde (represented by the structural formula (39)-1) in anhydrous tetrahydrofuran. The reactants were stirred for 10 hours. The reaction solution was quenched with a small amount of ice, washed with saturated aqueous solution of sodium chloride, and dried with anhydrous sodium sulfate.

The reaction product was purified by silica gel chromatography (WAKO-gel C-300, tetrahydrofuran:hexane=1:8) and then recrystallized from acetone-hexane mixed solvent. Thus there was obtained the desired bis(aminostyryl) naphthalene compound (represented by the structural formula (20)-2) in the form of red crystals (0.273 g).

This compound was identified by $^1$HNMR and FAB-MS. (20% yields)

$^1$HNMR (CDCl$_3$) δ (ppm) 3.83(6H,s), 6.87(4H,d), 6.89–7.14(12H,m), 7.25–7.53 (14H,m), 8.03(2H,d), 8.31 (2H,d)

This compound gave a $^1$HNMR spectrum as shown in FIG. 1. This compound has a glass transition point of 120° C. and a melting point of 272° C.

This compound gives a toluene solution which has the maximum visible absorption at 493 nm and the fluorescence maximum wavelength at 545 nm.

EXAMPLE 2

(Synthesis of bis(aminostyryl)naphthalene Compound Represented by the Structural Formula (20)-3)

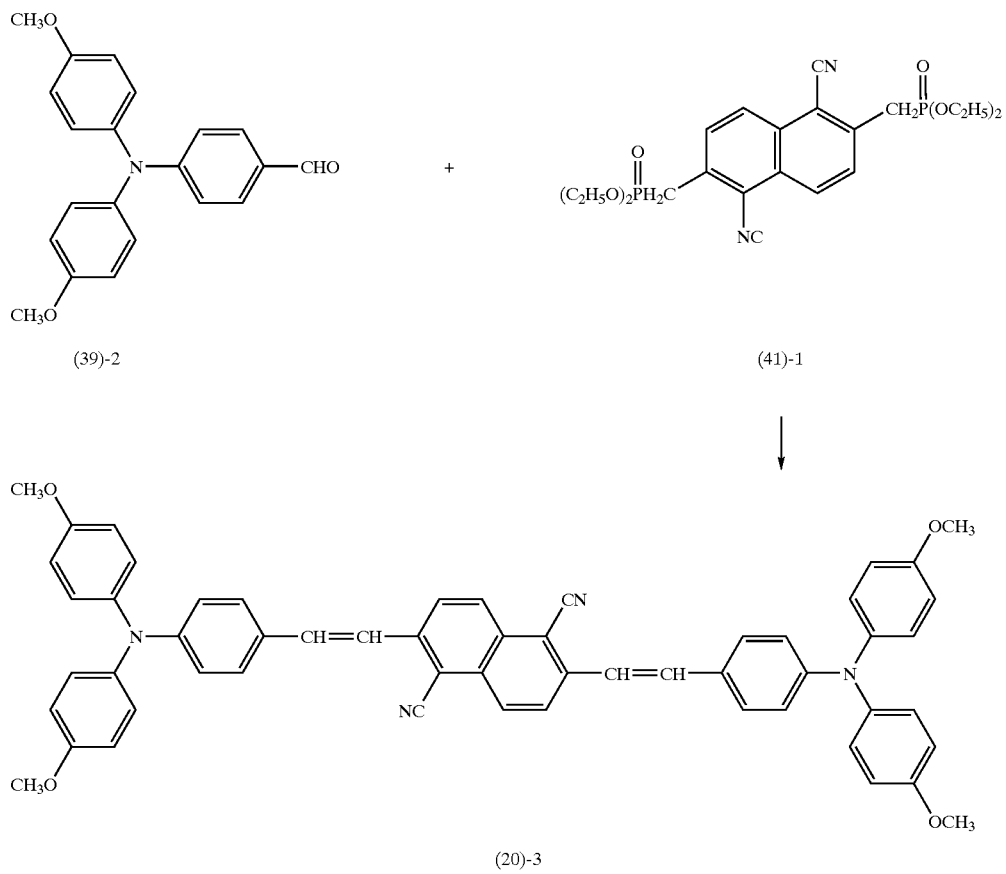

In a reactor was placed 7.50 mmol of sodium hydride (in mineral oil). It was washed twice with hexane. It was suspended in 20 mL of 1:1 mixed solvent of anhydrous THF and dimethylformamide (DMF). The suspension, placed on an ice bath, was given dropwise over 15 minutes under nitrogen atmosphere 100 mL of solution containing 0.720 g (1.51 mmol) of phosphonic ester (represented by the structural formula (41)-1) and 1.16 g (3.61 mmol) of 4-[N,N-di (4-methoxyphenyl)amino]benzaldehyde (represented by the structural formula (39)-2) in a 1:1 mixed solution of anhydrous THF and DMF. The reactants were stirred on an ice bath for 6 hours and then stirred at room temperature for 6 hours. The reaction solution was quenched with a small amount of ice, extracted with toluene, washed with saturated aqueous solution of sodium chloride, and dried with Na$_2$SO$_4$. The supernatant liquid was concentrated and the resulting precipitates were filtered off and washed repeatedly with ethanol (EtOH).

The thus obtained solids were purified by silica gel chromatography (WAKO-gel C-300, toluene:THF=10:1) and then recrystallized from toluene. Thus there was obtained the desired bis(aminostyryl)naphthalene compound (represented by the structural formula (20)-3) in the form of red crystals (0.731 g).

This compound was identified by $^1$HNMR and FAB-MS. (58% yields)

$^1$HNMR (CDCl$_3$) δ (ppm) 3.82(12H,s), 6.86(12H,m), 7.10(8H,d), 7.43(8H,m), 8.01(2H,d), 8.29(2H,d)

Figure 2:
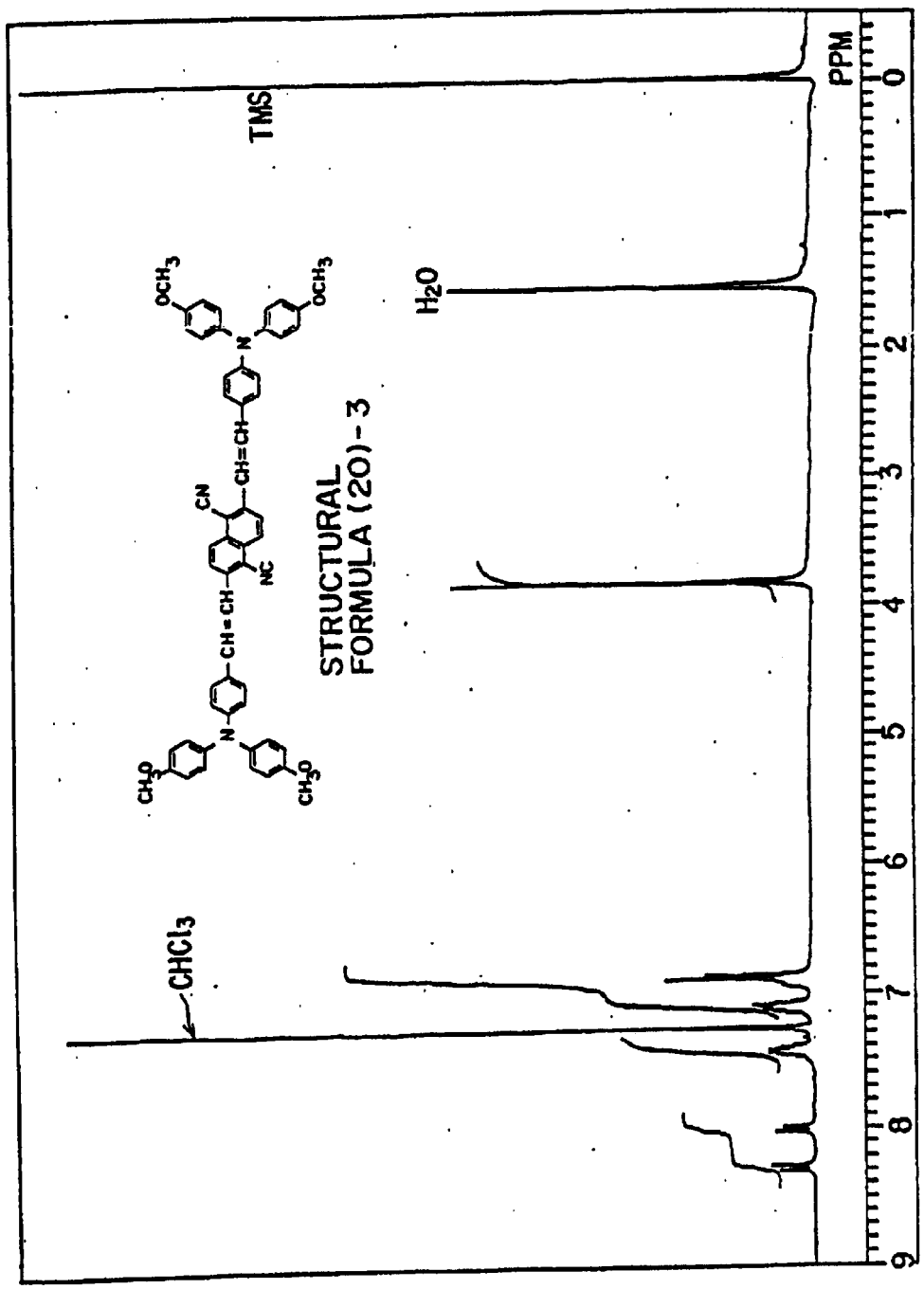
FIG. 2 is a $^1$HNMR spectral atlas of bis(aminostyryl) naphthalene compound (represented by the structural formula (20)-3) according to the present invention.

This compound gave a $^1$HNMR spectrum as shown in FIG. 2. This compound has a glass transition point of 140° C. and a melting point of 227° C.

This compound gives a toluene solution which has the maximum visible absorption at 502 nm and the fluorescence maximum wavelength at 565 nm.

EXAMPLE 3
(Synthesis of bis(aminostyryl)naphthalene Compound Represented by the Structural Formula (20)-13)

This compound was identified by $^1$HNMR and FAB-MS. (61% yields)

$^1$HNMR (CDCl$_3$) δ (ppm) 1.72(8H,s), 2.42(4H,s), 2.83 (4H,s), 3.80(6H,m), 6.79–6.85(8H,m), 6.86–7.23(10H,m), 7.34–7.50(6H,m), 8.00(2H,d), 8.29(2H,d)

Figure 3:
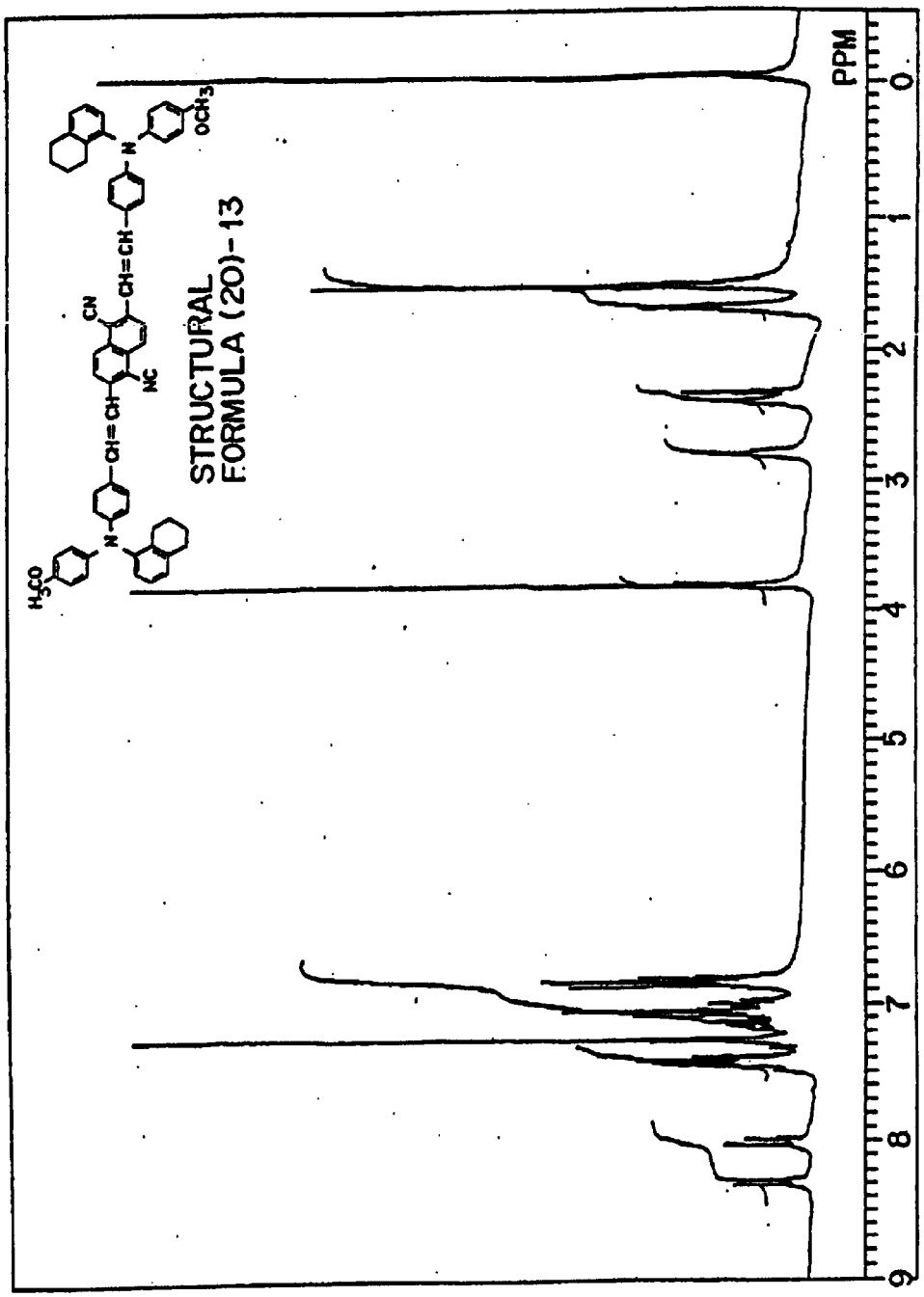
FIG. 3 is a $^1$HNMR spectral atlas of bis(aminostyryl) naphthalene compound (represented by the structural formula (20)-13) according to the present invention.

This compound gave a $^1$HNMR spectrum as shown in FIG. 3. This compound has a glass transition point of 135° C. and a melting point of 245° C.

This compound gives a toluene solution which has the maximum visible absorption at 496 nm and the fluorescence maximum wavelength at 540 nm.

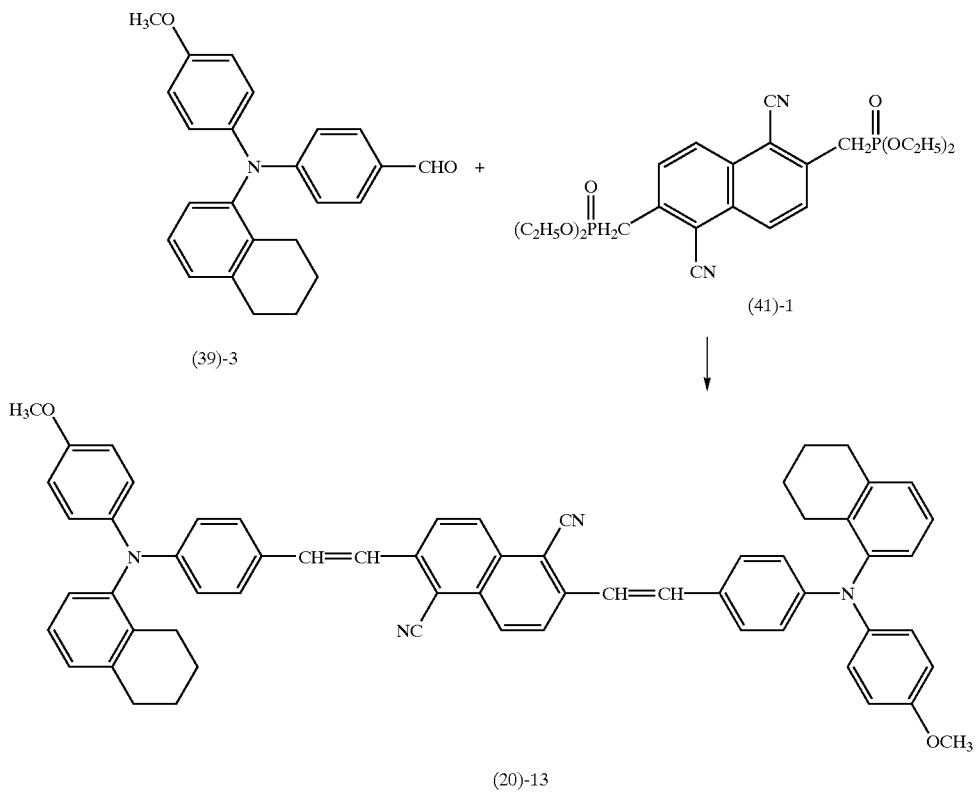

In a reactor was placed 5.15 mmol of sodium hydride (in mineral oil). It was washed twice with hexane. It was suspended in 5 mL of 3:1 mixes solvent of anhydrous THF and DMF. The suspension, placed on an ice bath, was given dropwise over 15 minutes under nitrogen atmosphere 50 mL of solution containing 0.410 g (0.858 mmol) of phosphonic ester (represented by the structural formula (41)-1) and 0.700 g (2.06 mmol) of 4-[N,N-(4-methoxyphenyl)-1-(2,3,4,5-tetrahydronaphthylamino)]benzaldehyde (represented by the structural formula (39)-3) in a 3:1 mixed solution of anhydrous THF and DMF. The reactants were stirred on an ice bath for 6 hours and then stirred at room temperature for 12 hours. The reaction solution was quenched with a small amount of ice, extracted with toluene, washed with saturated aqueous solution of sodium chloride, and dried with Na$_2$SO$_4$.

The reaction product was purified by silica gel chromatography (WAKO-gel C-300, toluene) and then recrystallized from toluene. Thus there was obtained the desired bis(aminostyryl)naphthalene compound (represented by the structural formula (20)-13) in the form of red crystals (0.465 g).

EXAMPLE 4
(Synthesis of Diphosphonic Ester Represented by the Structural Formula (41)-1)

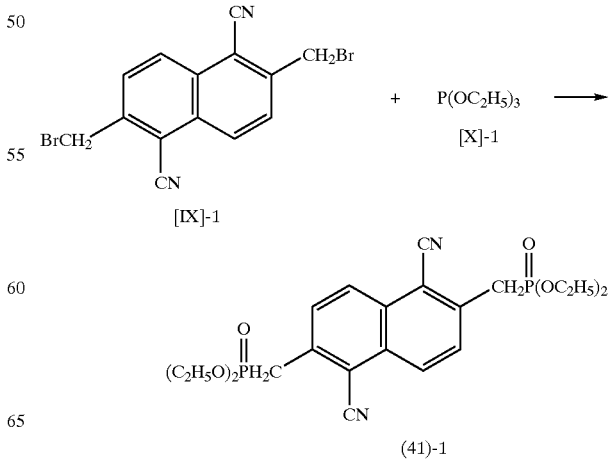

In 40 mL of xylene was dispersed 0.625 g (1.72 mmol) of 2,6-di(bromomethyl)naphthalene-1,5-dicarbonitrile (represented by the structural formula [IX]-1). This suspension was given dropwise 1.80 g (10.8 mmol) of triethyl phosphite (represented by the structural formula [x]-1). The reactants were stirred at 125° C. for 4 hours. The reaction solution was cooled to room temperature. With 100 mL of toluene added, the reaction solution was allowed to stand for precipitation. The resulting precipitates were filtered off and washed repeatedly with hexane. Thus there was obtained the desired diphosphonic ester (represented by the structural formula (41)-1).

Figure 4:
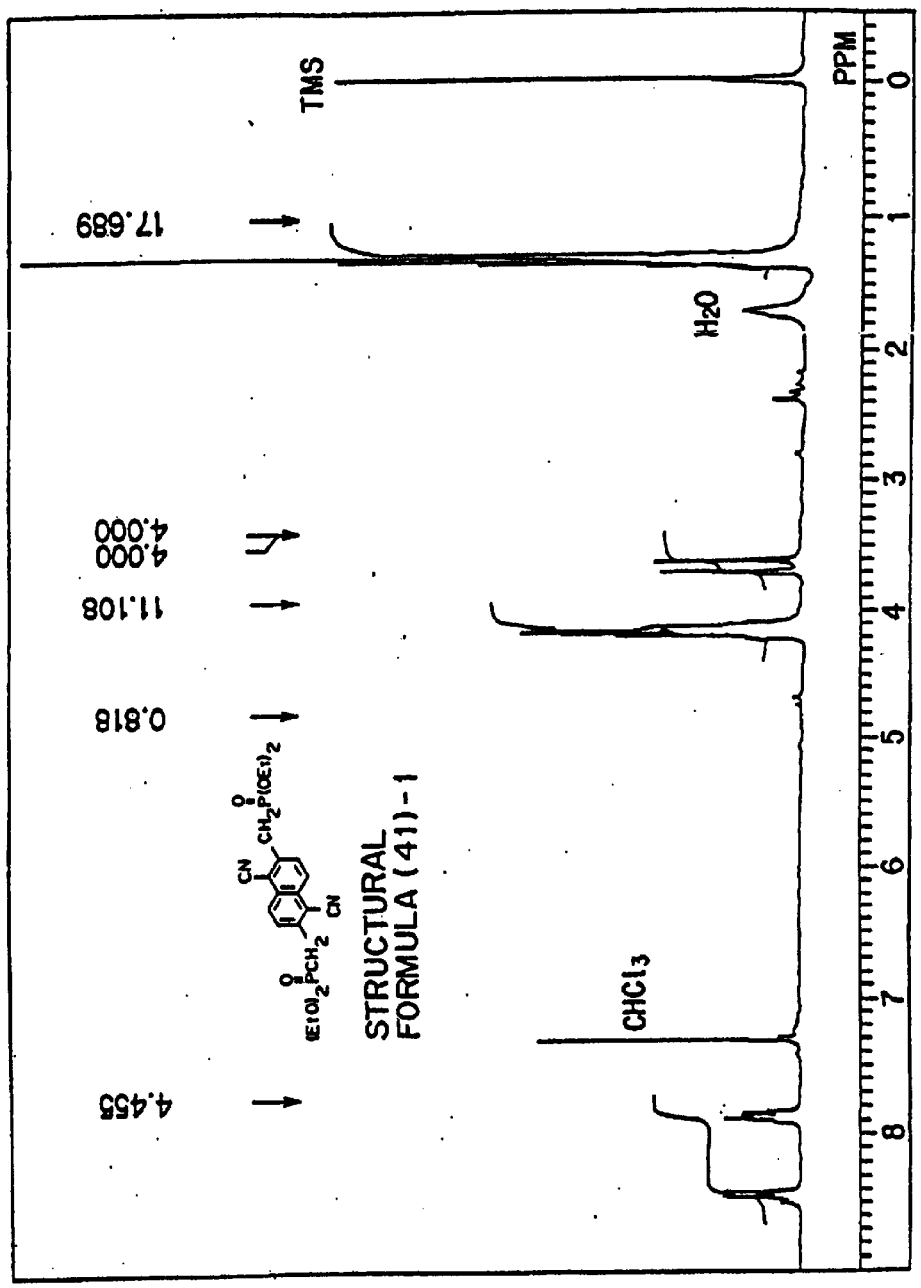
FIG. 4 is a $^1$HNMR spectral atlas of diphosphonic ester (represented by the structural formula (41)-1) as the synthesis intermediate according to the present invention.

This compound was identified by $^1$HNMR and FAB-MS.
$^1$HNMR (CDCl$_3$) δ (ppm): 1.33(12H,t), 3.63(4H,d), 4.14 (8H,q), 7.84(2H,d), 8.42(2H.d)
This compound gave a $^1$HNMR spectrum as shown in FIG. 4.

EXAMPLE 5
(Synthesis of 2,6-di(bromomethyl)naphthalene-1,5-dicarbonitrile Represented by the Structural Formula (IX)-1)

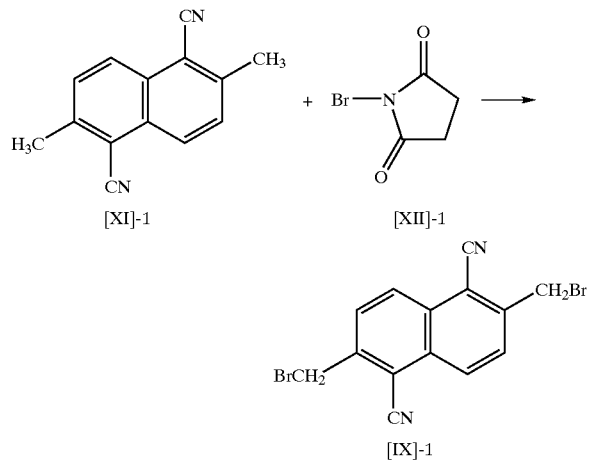

In 250 mL of chloroform was dissolved 2.00 g (9.70 mmol) of 2,6-dimethylnaphthalene-1,5-dicarbonitrile (represented by the structural formula [XI]-1). To this solution was added 13.6 g (76.6 mmol) of N-bromosuccinimide (represented by the structural formula [XII]-1) by portions (6 times at intervals of 12 hours) with reflux under nitrogen atmosphere.

The reaction solution was concentrated and the concentrate was purified by alumina chromatography (activated alumina, 300 mesh, chloroform). The precipitates were filtered off and washed repeatedly with hexane and recrystallized from toluene. Thus there was obtained the desired 2,6-di(bromomethyl)naphthalene-1,5-dicarbonitrile represented by the structural formula (IX)-1 in the form of yellow crystals (1.32 g).

Figure 5:
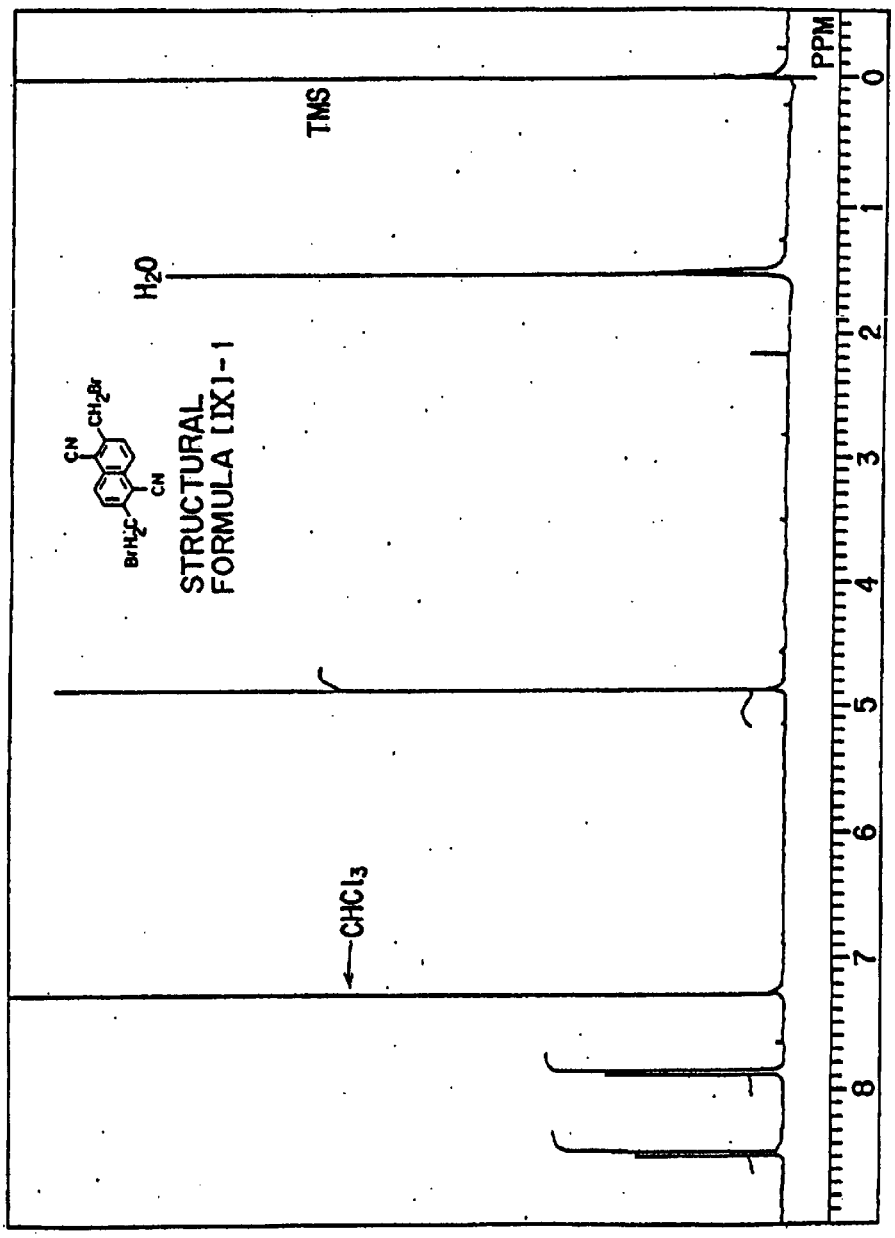
FIG. 5 is a $^1$HNMR spectral atlas of 2,6-di(bromo-methyl) naphthalene-1,5-dicarbonitrile (represented by the structural formula [IX]-1) as the synthesis intermediate according to the present invention.

This compound was identified by $^1$HNMR and FAB-MS. (38% yields)
$^1$HNMR (CDCl$_3$) δ (ppm): 4.83(4H,s), 7.86(2H,d), 8.47 (4H,d)
This compound gave a $^1$HNMR spectrum as shown in FIG. 5.

The compound of the present invention emits intense yellow to red light depending on the substituent groups introduced therein. Therefore, it is useful as an organic light-emitting material. It has a high glass transition point and a high melting point, so that it is superior in heat resistance and in electrical, thermal, and chemical stability. It can be readily made into an amorphous glass state. It is sublimable and hence can be formed into a uniform amorphous film by vacuum deposition. It can be produced efficiently by common process via the synthesis intermediate of the present invention.

What is claimed is:

1. A process for producing a diphosphonic ester of formula [VII] which comprises reacting an aryl halide compound of formula [IX] and a trialkyl phosphite of formula [X]

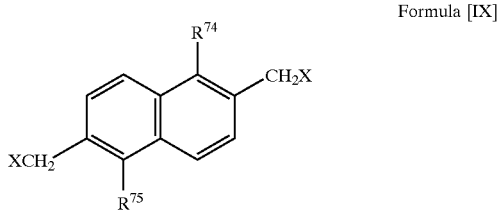

Formula [X]
P(OR$^{72}$)$_3$ or P(OR$^{73}$)$_3$

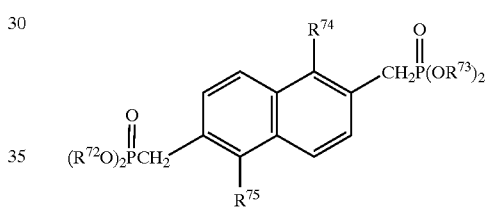

wherein
R$^{72}$ and R$^{73}$ are hydrocarbon moieties
R$^{74}$ is selected from the group consisting of —CN, —CCF$_3$, and —NO$_2$
R$^{75}$ is selected from the group consisting of —H, —CN, —CCF$_3$, —NO, —F, Cl, Br, and —I and X is a halogen atom.

2. A process for producing a diphosphonic ester as defined in claim 1, wherein R$^{72}$ and R$^{73}$ each denotes a saturated hydrocarbon group having 1 to 4 carbon atoms.

3. A process for producing a diphosphonic ester as defined in claim 1,
wherein
R$^{72}$ and R$^{73}$ are hydrocarbon moieties, and
R$^{74}$ and R$^{75}$ are cyano groups.

4. A process for producing a diphosphonic ester as defined in claim 1,
wherein
R$^{72}$ and R$^{73}$ are hydrocarbon moieties, and
R$^{74}$ is a hydrogen atom, and
R$^{76}$ is a cyano group.

* * * * *